US012788338B2

(12) United States Patent
Helm et al.

(10) Patent No.: US 12,788,338 B2
(45) **Date of Patent: *Nov. 10, 2026**

(54) SYSTEM AND METHOD FOR IMAGING

(71) Applicant: Medtronic Navigation, Inc., Lafayette, CO (US)

(72) Inventors: Patrick A. Helm, Canton, MA (US); Shuanghe Shi, Southborough, MA (US)

(73) Assignee: Medtronic Navigation, Inc., Lafayette, CO (US)

( * ) Notice: Subject to any disclaimer, the term of this patent is extended or adjusted under 35 U.S.C. 154(b) by 140 days.

This patent is subject to a terminal disclaimer.

(21) Appl. No.: 18/819,224

(22) Filed: Aug. 29, 2024

(65) Prior Publication Data

US 2024/0423563 A1 Dec. 26, 2024

Related U.S. Application Data

(63) Continuation of application No. 17/473,728, filed on Sep. 13, 2021, now Pat. No. 12,076,172.

(60) Provisional application No. 63/078,048, filed on Sep. 14, 2020, provisional application No. 63/078,065, filed on Sep. 14, 2020, provisional application No. 63/078,060, filed on Sep. 14, 2020.

(51) Int. Cl.

| | |
|---|---|
| ***A61B 6/00*** | (2024.01) |
| ***A61B 6/03*** | (2006.01) |
| ***A61B 6/40*** | (2024.01) |
| ***A61B 90/00*** | (2016.01) |
| *A61B 34/20* | (2016.01) |

(52) U.S. Cl.
CPC ............ *A61B 6/4007* (2013.01); *A61B 6/032* (2013.01); *A61B 6/4085* (2013.01); *A61B 6/4405* (2013.01); *A61B 6/4452* (2013.01); *A61B 6/487* (2013.01); *A61B 90/37* (2016.02); *A61B 34/20* (2016.02); *A61B 2090/3762* (2016.02)

(58) Field of Classification Search
CPC ...... A61B 6/4452; A61B 6/4007; A61B 6/487
See application file for complete search history.

(56) References Cited

U.S. PATENT DOCUMENTS

| | | | |
|---|---|---|---|
| 5,592,939 | A | 1/1997 | Martinelli |
| 5,913,820 | A | 6/1999 | Bladen et al. |
| 5,983,126 | A | 11/1999 | Wittkampf |
| 6,474,341 | B1 | 11/2002 | Hunter et al. |
| 6,940,941 | B2 | 9/2005 | Gregerson et al. |

(Continued)

FOREIGN PATENT DOCUMENTS

| | | | |
|---|---|---|---|
| CN | 1780585 | A | 5/2006 |
| CN | 1853570 | A | 11/2006 |

(Continued)

OTHER PUBLICATIONS

U.S. Appl. No. 17/473,728, filed Sep. 13, 2021, Patrick A. Helm.

(Continued)

*Primary Examiner* — Dani Fox
(74) *Attorney, Agent, or Firm* — Harrity & Harrity, LLP

(57) ABSTRACT

Disclosed is a system for imaging a system. The system may be operated to acquire image data of a subject in one or more manners. The image data acquired may be used to various purposes, such as generating an image for display, navigating a procedure, or other appropriate procedures.

20 Claims, 24 Drawing Sheets

(56) References Cited

U.S. PATENT DOCUMENTS

| | | | |
|---|---|---|---|
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,227,923 B2 | 6/2007 | Edic et al. | |
| 7,639,775 B2 | 12/2009 | DeMan et al. | |
| 7,684,538 B2 | 3/2010 | Morton et al. | |
| 7,751,865 B2 | 7/2010 | Jascob et al. | |
| 8,150,494 B2 | 4/2012 | Simon et al. | |
| 8,175,681 B2 | 5/2012 | Hartmann et al. | |
| 8,503,745 B2 | 8/2013 | Simon et al. | |
| 8,562,211 B2 | 10/2013 | Helm et al. | |
| 8,737,708 B2 | 5/2014 | Hartmann et al. | |
| 9,737,235 B2 | 8/2017 | Hartmann | |
| 11,813,094 B2 | 11/2023 | Helm et al. | |
| 12,023,187 B2 | 7/2024 | Helm et al. | |
| 12,076,172 B2 | 9/2024 | Helm et al. | |
| 2003/0108146 A1 | 6/2003 | Malamud | |
| 2004/0013225 A1 | 1/2004 | Gregerson et al. | |
| 2008/0101533 A1 | 5/2008 | Ein-Gal | |
| 2009/0161816 A1* | 6/2009 | De Man | A61B 6/4028 378/92 |
| 2011/0280379 A1 | 11/2011 | Maschke | |
| 2011/0280380 A1 | 11/2011 | Maschke | |
| 2013/0343509 A1 | 12/2013 | Gregerson et al. | |
| 2018/0353145 A1 | 12/2018 | Simon et al. | |
| 2020/0205763 A1 | 7/2020 | Helm et al. | |
| 2021/0212644 A1 | 7/2021 | Glatz et al. | |

FOREIGN PATENT DOCUMENTS

| | | | |
|---|---|---|---|
| CN | 101512379 | A | 8/2009 |
| CN | 103648389 | A | 3/2014 |
| CN | 109069095 | A | 12/2018 |
| WO | 2009115982 | A1 | 9/2009 |
| WO | 2017156118 | A2 | 9/2017 |
| WO | PCT/US2021/050198 | | 9/2021 |
| WO | PCT/US2021/050209 | | 9/2021 |
| WO | PCT/US2021/050223 | | 9/2021 |

OTHER PUBLICATIONS

U.S. Appl. No. 63/078,048, filed Sep. 14, 2020, Patrick A. Helm.

U.S. Appl. No. 63/078,060, filed Sep. 14, 2020, Patrick A. Helm.

U.S. Appl. No. 63/078,065, filed Sep. 14, 2020, Patrick A. Helm.

U.S. Appl. No. 17/473,695, filed Sep. 13, 2021, Patrick A. Helm.

U.S. Appl. No. 17/473,646, filed Sep. 13, 2021, Patrick A. Helm.

U.S. Appl. No. 18/759,994, filed Jun. 30, 2024, Patrick A. Helm.

International Preliminary Report on Patentability regarding Application No. PCT/US2021/050198, dated Mar. 23, 2023.

International Preliminary Report on Patentability regarding Application No. PCT/US2021/050209, dated Mar. 23, 2023.

International Preliminary Report on Patentability regarding Application No. PCT/US2021/050223, dated Mar. 23, 2023.

International Search Report and Written Opinion regarding International Application No. PCT/US2021/050198, dated Jan. 31, 2022.

International Search Report and Written Opinion regarding International Application No. PCT/US2021/050209, dated Dec. 9, 2021.

International Search Report and Written Opinion regarding International Application No. PCT/US2021/050223, dated Dec. 9, 2021.

Invitation to Pay Additional Fees mailed Dec. 9, 2021, in corresponding/related International Application No. PCT/US2021/050198.

* cited by examiner

SYSTEM AND METHOD FOR IMAGING

CROSS-REFERENCE TO RELATED APPLICATIONS

This application is a continuation of U.S. patent application Ser. No. 17/473,728 filed Sep. 13, 2021 which claims the benefit of all of U.S. Provisional Application No. 63/078,048, filed Sep. 14, 2020; U.S. Provisional Application No. 63/078,060, filed Sep. 14, 2020; and U.S. Provisional Application No. 63/078,065, filed Sep. 14, 2020 all of which and the entire disclosure of the above applications are incorporated herein by reference.

FIELD

The subject disclosure is related to imaging, and particularly imaging with a multiple source imaging system and methods related thereto.

BACKGROUND

This section provides background information related to the present disclosure which is not necessarily prior art.

An imaging system generally includes a source portion and a detector portion. The source portion generates a signal that is detected by the detector portion. An object may be positioned relative to the imaging system to attenuate the signal between the source and the detector in a manner to allow for acquisition of image data and/or a related image or for reconstruction of an image. The imaging system, however, is generally limited to a single source and single detector. Therefore a volume to be imaged is generally proportional to a size of the source and related detector and, therefore, a larger source and detector is required for a larger object.

SUMMARY

This section provides a general summary of the disclosure, and is not a comprehensive disclosure of its full scope or all of its features.

A navigation system may be used to track and determine a pose (also referred to as a position), which can include at least some coordinates of location and/or orientation, of an instrument over time. In various embodiments, pose of the instrument is understood to include at least some tracked or navigated location coordinates (e.g. x, y, z) and/or orientation coordinates (e.g. roll, pitch, yaw). The navigation system may, therefore, track a pose of an object, including at least one degree of freedom and further including at least six degrees of freedom of motion (e.g. a three-dimensional location and a plurality, e.g. pitch, roll, and yaw, of orientation). The pose of the tracked instrument may be determined at an instant in time and/or over time. In various embodiments, a visual representation of the instrument may be illustrated with a display device relative to an image, such as an image of at least a portion of a subject.

In various embodiments, the pose of the tracked instrument may be determined relative to a subject. The subject may be any appropriate subject such as a living or non-living subject. In various embodiments, a non-living subject may include a hollow or enclosed casing, or other appropriate inanimate object. The inanimate object may have an outer covering that is opaque. Accordingly, a navigation or tracking system may be used to track an instrument during use relative to the inanimate object.

In various embodiments, the subject may include a living subject, such as a human subject. A procedure may include a surgical procedure where an instrument is positioned within a subject for a selected period of time to perform a procedure, such as a stent placement, deep brain stimulation probe placement, or placing or implanting other implantable member. Further, selected procedures may include a bone resection, bore formation, or the like relative to the subject. Regardless, the pose of the instrument may be determined with the navigation system.

An imaging system may include a plurality of sources that are spaced apart from one another. The plurality of sources may be individually powered to emit a signal, such as x-rays, from each of the individual sources. The x-rays from each of the sources may be detected by a detector at a selected time.

Generally, the sources may be spaced apart from one another to allow for collection of image data at different positions relative to the subject from each of the sources. The sources may be spaced apart relative to one another along a Z axis, (e.g. an axis of movement of the imaging system) that may be a longitudinal axis of the subject. The sources may also be spaced apart along an annular radius such that the sources are angularly spaced apart from one another. The spaced apart sources may also be moved relative to a subject, such as in a circular pattern, helical pattern, spiral pattern, portions thereof, or combinations thereof. The plurality of sources, therefore, may be positioned relative to one another and a detector to acquire image data of a subject in a selected manner.

The plurality of sources, also referred to as multiple sources, may be individually operated in a selected manner to acquire image data of the subject. For example, the multiple sources may include two or more sources, five or more sources, ten or more sources, and/or fifteen or more sources. For example, if five sources are included the imaging system may operate to sequentially emit x-rays from each of the sources separated by a period of time. In various embodiments, each of the five sources may be powered to emit x-rays for a selected period of time (e.g. one millisecond) and a pause between each of the powering of the sources for a selected period of time (e.g. one millisecond). Further, the sources may be powered in a non-sequential manner in any appropriate or selected pattern, such as the first source and the third source simultaneously or sequentially, followed by the third source and the fifth source, also simultaneously and/or sequentially. Thus, the multiple source imaging system may operate to emit x-rays in any appropriate manner by selectively powering and operating the multiple sources simultaneously, sequentially, serially, or in any appropriate manner.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Disclosed herein are exemplary embodiments, as discussed further herein. Generally, various embodiments may be disclosed relative to a human subject. It is understood, however, that various disclosed systems, such as navigation or tracking systems, may be used relative to any subject or system that may have an outer hull or shell that may encompass internal components or operations. For example, an air frame or automobile frame may obscure internal components, which may be selected to be operated on in a selected procedure. The selected procedure may include removal, replacement, or the like of various components of any non-animate or inanimate system. Accordingly, it is understood that a discussion herein relative to a subject, such as a human subject, is merely exemplary.

Further, as discussed herein, a navigation system may include tracking various components, such as an instrument, relative to a reference frame within a coordinate system or space. In various embodiments, the coordinate space may include a subject coordinate space or a real space defined by real space relative to the subject. Additional coordinate spaces may include image space that has an image coordinate space defined by an image of the subject. A pose of an instrument, as discussed above, may be illustrated relative to, for example superimposed on, an image with a graphical representation for viewing by a user. Such illustrations may require or use registration between a subject space or subject coordinate space and an image coordinate space or image space. An imaging system, as discussed herein may be configured and/or operated to acquire image data for generation of selected images of a subject.

One or more methods to register a subject space defined by a subject to an image space may include those disclosed in U.S. Pat. Nos. 8,737,708; 9,737,235; 8,503,745; and 8,175,681; all incorporated herein by reference.

Figure 1:
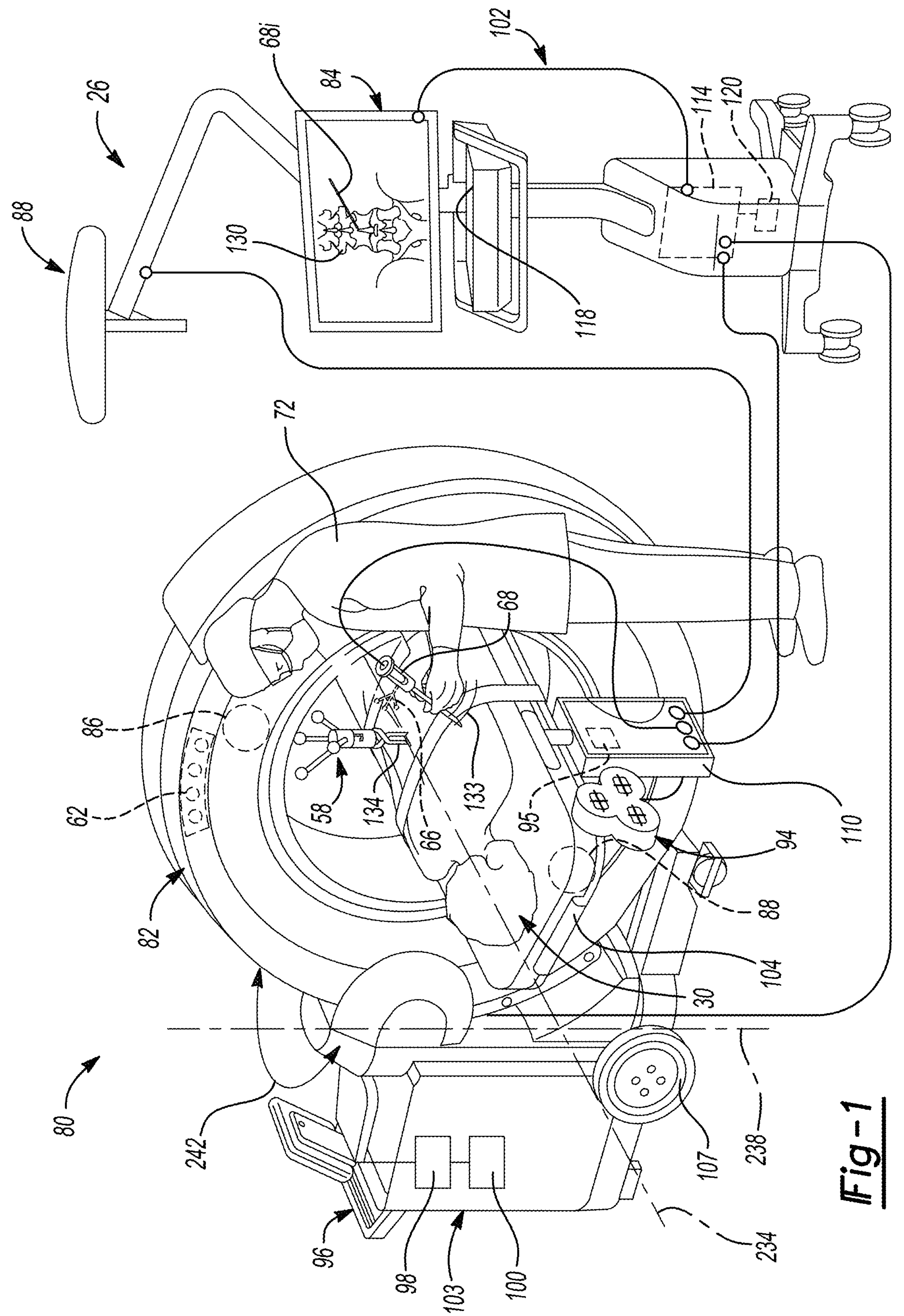
FIG. 1 is diagrammatic view illustrating an overview of a procedure room including an imaging system, according to various embodiments.

FIG. 1, according to various embodiments, is a diagrammatic view illustrating an overview of a procedure room or area. In various embodiments, the procedure room may include a surgical suite. The surgical suite may include a navigation system 26 that can be used for various procedures, such as those relative to a subject 30.

The navigation system 26 can be used to track the pose of one or more tracking devices. The tracking devices may include tracking devices that are operable to be tracked by one or more tracking systems, such as an optical or electromagnetic (EM) tracking system. For example, tracking devices may include a subject tracking device or dynamic reference frame (DRF) 58 (that may be referred to separately as EM 58' and/or optical 58"), an imaging system tracking device 62 (that may be referred to separately as EM 62' and/or optical 62"), and/or a tool tracking device 66 (that may be referred to separately as EM 66' and/or optical 66"). Other tracking devices may also be included, such as a user or clinician tracking device alone or in combination with other systems (e.g. augmented reality systems).

A tool 68 may be operated or handled by a user 72. The tool 68 may also be referred to as an object or item that is operable to be tracked. Thus, the tool 68 may be associated with the tool tracking device 66. The tool 68 may be any appropriate tool such as a drill, forceps, or other tool operated by the user 72. The tool 68 may also include an implant, such as a spinal implant or orthopedic implant. It should further be noted that the navigation system 26 may be used to navigate any type of instrument, implant, or delivery system, including: guide wires, arthroscopic systems, orthopedic implants, spinal implants, deep brain stimulation (DBS) probes, etc. Moreover, the instruments may be used to navigate or map any region of the body. The navigation system 26 and the various instruments may be used in any appropriate procedure, such as one that is generally minimally invasive or an open procedure.

An imaging system 80 may include any one or more devices that may be used to acquire pre-, intra-, or post-operative or real-time image data of a subject, such as the subject 30. It will be understood, however, that any appropriate subject can be imaged and any appropriate procedure may be performed relative to the subject. In the example shown, the imaging device 80 comprises an O-arm® imaging device sold by Medtronic Navigation, Inc. having a place of business in Louisville, Colorado, USA. The imaging device 80 may have a generally annular gantry housing 82 in which an image capturing portion is moveably placed. The image capturing portion may include an x-ray source or emission portion 86 and an x-ray detector 88 (also referred to as a receiving or image receiving portion). As discussed herein, the source 86 may include one or more emission points or portions that each may be operated to emit x-rays to the detector 88. Both the source 86 (including one or more emission portions) and the detector 88 may be operated to move as the image capturing portion.

In various embodiments, the source 86 and the detector 88 are located generally or as practically possible 180 degrees from each other. As discussed above, the source may include a plurality of emission portions, nevertheless, the source and the detector may be mounted on a rotor relative to a track or rail (not illustrated). The image capturing portion can be operable to rotate at least or any selected portion of 360 degrees during image acquisition. The image capturing portion may rotate around a central point or axis, allowing image data of the subject 30 to be acquired from multiple directions or in multiple planes. The imaging device 80 can include at least selected portions including portions (e.g. a gantry, a mobile cart, etc.) disclosed in U.S. Pat. Nos. 7,188,998; 7,108,421; 7,106,825; 7,001,045; and 6,940,941; all of which are incorporated herein by reference, or any appropriate portions thereof. In various embodiments, the imaging device 80 can utilize flat plate or panel detector 88 technology having a selected pixel viewing area.

The position of the imaging device 80, and/or portions therein such as the image capturing portion, can be precisely known relative to any other portion of the imaging device 80. The imaging device 80, according to various embodiments, can know and recall precise coordinates relative to a fixed or selected coordinate system. This can allow the imaging system 80 to know its position relative to the patient 30 or other references. In addition, as discussed herein, the precise knowledge of the position of the image capturing portion can be used in conjunction with a tracking system to determine the position of the image capturing portion and the image data relative to the tracked subject, such as the patient 30.

The imaging device 80 can also be tracked with the image tracking device 62. The image data defining an image space acquired of the patient 30 can, according to various embodiments, be inherently or automatically registered relative to an object space. The object space can be the space defined by a patient 30 in the navigation system 26. The automatic registration can be achieved by including the tracking device 62 on the imaging device 80 and/or the determinable precise pose of the image capturing portion. According to various embodiments, as discussed herein, imageable portions, virtual fiducial points and other features can also be used to allow for registration, automatic or otherwise. It will be understood, however, that image data can be acquired of any subject which will define subject space. Patient space is an exemplary subject space. Registration allows for a map between patient space and image space. In various embodiments, as discussed herein, registration to pre-acquired image data may also be performed with the imaging system 80 and may allow for automatic registration to the pre-acquired image data and, also, to the subject 30.

The patient 30 can also be tracked as the patient moves with the patient tracking device, DRF, or tracker 58. Alternatively, or in addition thereto, the patient 30 may be fixed within navigation space defined by the navigation system 26 to allow for registration. As discussed further herein, registration of the image space to the patient space or subject space allows for navigation of the instrument 68 with the image data. When navigating the instrument 68, a pose of the instrument 68 can be illustrated relative to image data acquired of the patient 30 on a display device 84.

Various tracking systems, including one or more of an optical localizer 88 or an electro-magnetic (EM) localizer 94, can be used to track the instrument 68. As discussed herein, in various embodiments, the localizer 94 may transmit a signal that is received by the tracking device 66, or other appropriate tracking device. In addition, an appropriate antenna, e.g. a coil, may also be provided as a receiver. For example, a calibration receiver 95 (e.g. a coil) may be provided to receive a signal form the localizer 94. The calibration receiver 95 may be included in any appropriate portion of the navigation system 26, such as a controller 110, as discussed further herein. It is understood by one skilled in the art that the calibration receiver 95 need not be incorporated into the navigation system 26 during a use, but may be provided or used during an initial (e.g. factory) production or calibration of the navigation system 26. In various embodiments, the calibration receiver 95 may receive the signal from the localizer 94 in a manner similar to the tracking device 66 and be used for various purposes, as discussed herein.

More than one tracking system can be used to track the instrument 68 in the navigation system 26. According to various embodiments, tracking systems can include the electromagnetic tracking (EM) system having the EM localizer 94 and/or the optical tracking system having the optical localizer 88. Either or both of the tracking systems can be used to tracked selected tracking devices, as discussed herein. It will be understood, unless discussed otherwise, that a tracking device can be a portion trackable with a selected tracking system. A tracking device need not refer to the entire member or structure to which the tracking device is affixed or associated.

It is further appreciated that the imaging device 80 may be an imaging device other than the O-arm® imaging device and may include in addition or alternatively a fluoroscopic C-arm. Other exemplary imaging devices may include fluoroscopes such as bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, etc. In various embodiments, an imaging system in addition to or alternatively to the imaging system 80 may also be used to acquired image data (such as pre-acquired image data) of the subject 30. Other appropriate imaging devices can include MRI, CT, ultrasound, etc.

In various embodiments, an imaging device controller 96 may control the imaging device 80 and can receive the image data generated at the image capturing portion and store the images for later use. The controller 96 can also control the rotation of the image capturing portion of the imaging device 80. It will be understood that the controller 96 need not be integral with the gantry housing 82, but may be separate therefrom. For example, the controller may be a portion of the navigation system 26 that may include a processing module or system 98 and/or a memory module or system 100. The controller 96, however, may be integral or connected with the gantry 82 and may include a second and separate processor, such as that in a portable computer.

The patient 30 can be positioned, including fixed, on an operating table 104. According to one example, the table 104 can be an Axis Jackson® operating table sold by OSI, a subsidiary of Mizuho Ikakogyo Co., Ltd., having a place of business in Tokyo, Japan or Mizuho Orthopedic Systems, Inc. having a place of business in California, USA. Patient positioning devices can be used with the table, and include a Mayfield® clamp or those set forth in U.S. Pat. App. Pub. No. 2004/0199072, published Oct. 7, 2004 (U.S. patent application Ser. No. 10/405,068) entitled "An Integrated Electromagnetic Navigation And Patient Positioning Device", which is hereby incorporated by reference.

The position of the patient 30 relative to the imaging device 80 can be determined by the navigation system 26. The tracking device 62 can be used to track and determine a pose of at least a portion of the imaging device 80, for example the gantry or housing 82. The patient 30 can be tracked with the dynamic reference frame 58, as discussed further herein. Accordingly, the position of the patient 30 relative to the imaging device 80 can be determined by tracking the patient tracking device 58 and the imaging tracking device 62. As discussed herein, however, the imaging system 80 may be operated to determine the position of the subject 30 relative to selected portions of the imaging system 80. In various embodiment, the pose of the imaging portion can be determined relative to the housing 82 due to its precise position on the rail within the housing 82, substantially inflexible rotor, etc. The imaging device 80 can include an accuracy of within 10 microns, for example, if the imaging device 80 is an O-Arm® imaging device sold by Medtronic Navigation, Inc. having a place of business in Louisville, Colorado. Precise positioning of the imaging portion is further described in U.S. Pat. Nos. 7,188,998; 7,108,421; 7,106,825; 7,001,045; and 6,940,941; all of which are incorporated herein by reference, According to various embodiments, the imaging device 80 can generate and/or emit x-rays from the x-ray source 86 that propagate through the patient 30 and are received by the x-ray detector 88 that may be include with an image capturing portion. The x-ray detector 88 generates image data representing the intensities of the received or detected x-rays. In various embodiments, the image capturing portion can include an image intensifier that first converts the x-rays to visible light and a camera (e.g. a charge-coupled device) that converts the visible light into digital image data. The image capturing portion may also be a digital device that converts x-rays directly to digital image data for forming images, thus potentially avoiding distortion introduced by first converting to visible light.

Two dimensional and/or three dimensional fluoroscopic image data that may be taken by the imaging device 80 can be captured and stored in the imaging device controller 96. Multiple image data taken by the imaging device 80 may also be captured and assembled to provide a larger view or image of a whole region of a patient 30, as opposed to being directed to only a portion of a region of the patient 30. For example, multiple image data of the patient's 30 spine may be appended together to provide a full view or complete set of image data of the spine.

The image data can then be forwarded from the image device controller 96 to a selected workstation of computer system 110. The workstation 110 may include or be a portion of the navigation system 26. The workstation 110 may include a processor system or module that may be a navigation computer and/or processor system 114. The workstation 110 may further include the display 84 and a user interface 118 and/or a memory module or system 120. It will also be understood that the image data is not necessarily first retained in the controller 96, but may also be directly transmitted to the work station 102. The work station 102 can provide facilities for displaying the image data as an image 130 on the display 84, saving, digitally manipulating, or printing a hard copy image of the received image data. The user interface 118, which may be a keyboard, mouse, touch pen, touch screen or other suitable device, allows the user 72 to provide inputs to control the imaging device 80, via the image device controller 96, or adjust the display settings of the display 84. The work station 102 may also direct the image device controller 96 to adjust the image capturing portion of the imaging device 80 to obtain various two-dimensional images along different planes in order to generate representative two-dimensional and three-dimensional image data.

The navigation system 26 can include the tracking systems including either or both of the electromagnetic (EM) localizer 94 and/or the optical localizer 88. The tracking systems may include the controller and interface portion 110. The controller 110 can be connected to the processor portion 114, which can include a processor included within a computer. The EM tracking system may include the STEALTHSTATION® AXIEM™ Navigation System, sold by Medtronic Navigation, Inc. having a place of business in Louisville, Colorado; or can be the EM tracking system described in U.S. Pat. No. 7,751,865, issued Jul. 6, 2010, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997; all of which are herein incorporated by reference. It will be understood that the navigation system 26 may also be or include any appropriate tracking system, including a STEALTHSTATION® TREON®, STEALTHSTATION® S7™, and/or STEALTHSTATION® S8™ tracking systems having an optical localizer and/or EM localizer, that may be used as the optical localizer 88, and sold by Medtronic Navigation, Inc. of Louisville, Colorado. Additional representative or alternative localization and tracking system is set forth in U.S. Pat. No. 5,983,126, entitled "Catheter Location System and Method," issued Nov. 9, 1999, which is hereby incorporated by reference. The navigation system 26 may be a hybrid system that includes components from various tracking systems.

Other tracking systems include an acoustic, radiation, radar, etc. The tracking systems can be used according to generally known or described techniques in the above incorporated references. Details will not be included herein except when to clarify selected operation of the subject disclosure.

Wired or physical connections can interconnect the tracking systems, imaging device 80, etc. Alternatively, various portions, such as the instrument 68 may employ a wireless communications channel, such as that disclosed in U.S. Pat. No. 6,474,341, entitled "Surgical Communication Power System," issued Nov. 5, 2002, herein incorporated by reference, as opposed to being coupled directly to the controller

110. Also, the tracking devices 58, 62, 66, can generate a field and/or signal that is sensed by the localizer(s) 88, 94. In various embodiments, the instrument tracking device 66, and/or other appropriate tracking devices, may communicate via a wired communication or a wireless signal 134, as discussed herein, with the controller 110 and/or the array 94. Further, any of the various components, including the imaging system 80 and/or tracking systems may transmit signals via wired, wireless, or combinations thereof communication systems. In various embodiments, the array 94 may operate with a spread spectrum signal to communicate with the tracking device 66.

Various portions of the navigation system 26, such as the instrument 68, and others as will be described in detail below, can be equipped with at least one, and generally multiple, of the tracking devices 66. The instrument can also include more than one type or modality of tracking device 66, such as an EM tracking device and/or an optical tracking device. The instrument 68 can include a portion that is capable of being grasped and/or manipulated (i.e. manipulable portion) at a proximal end and the tracking devices may be fixed near the manipulable portion of the instrument 68. It is understood, however, that the tracking device may also be placed at a distal or intervention end of the instrument 68.

According to various embodiments, the navigation system 26 can be used to track the instrument 68 relative to the patient 30. The instrument 68 can be tracked with the tracking system, as discussed herein, such as by tracking and determining a pose of the tracking device 66. Image data of the patient 30, or an appropriate subject, can be used to assist the user 72 in guiding the instrument 68. The image data, however, is registered to the patient 30. The image data defines an image space that is registered to the patient space defined by the patient 30. The registration can be performed as discussed herein, automatically, manually, or combinations thereof.

Generally, registration allows a map, also referred to as a registration map, to be generated of the physical pose of the instrument 68 relative to the image space of the image data. The map allows the tracked pose of the instrument 68 to be displayed on the display device 84 relative to the image 130. It is understood that the display device 84 may be any appropriate display device, or include more than a single display device, such as including augmented reality viewers, head mounted displays, etc. A graphical representation **68*i*, also referred to as an icon, can be used to illustrate the pose (e.g. three-dimensional coordinate location and one or more degree of freedom orientation) of the instrument 68 relative to the image 130**.

A subject registration system or method can use the subject tracking device 58. The tracking device 58 may include portions or members that may be trackable, but may also act as or be operable as a fiducial assembly. The fiducial assembly can include a clamp or other fixation portion 134 and the imageable fiducial body. It is understood, however, that the members may be separate from the tracking device 58. The fixation portion 134 can be provided to fix any appropriate portion, such as a portion of the anatomy. As illustrated in FIG. 1, the fiducial assembly 120 can be interconnected with a portion of a spine such as a spinous process of the subject 30.

The fixation portion 134 can be interconnected with the spinous process in any appropriate manner. For example, a pin or a screw can be driven into the spinous process. Alternatively, or in addition thereto, a clamp portion can be provided as the connection portion 134 to interconnect the spinous process. The fiducial portions may be imaged with the imaging device 80. It is understood, however, that various portions of the subject (such as a spinous process) may also be used as a fiducial portion.

In various embodiments, when the fiducial portions are imaged with the imaging device 80, image data is generated that includes or identifies the fiducial portions. The fiducial portions can be identified in image data automatically (e.g. with a processor executing a program), manually (e.g. by selection an identification by the user 72), or combinations thereof (e.g. by selection an identification by the user 72 of a seed point and segmentation by a processor executing a program). Methods of automatic imageable portion identification include those disclosed in U.S. Pat. No. 8,150,494 issued on Apr. 3, 2012, incorporated herein by reference. Manual identification can include selecting an element (e.g. pixel) or region in the image data wherein the imageable portion has been imaged. Regardless, the fiducial portions identified in the image data can be used as fiducial points or positions that can be used to register the image data or the image space of the image data with patient space.

In various embodiments, to register an image space or coordinate system to another space or coordinate system, such as a navigation space, the fiducial portions that are identified in the image 130 may then be identified in the subject space defined by the subject 30, in an appropriate manner. For example, the user 72 may move the instrument 68 relative to the subject 30 to touch the fiducial portions, if the fiducial portions are attached to the subject 30 in the same position during the acquisition of the image data to generate the image 130. It is understood that the fiducial portions, as discussed above in various embodiments, may be attached to the subject 30 and/or may include anatomical portions of the subject 30. Additionally, a tracking device may be incorporated into the fiducial portions and they may be maintained with the subject 30 after the image is acquired. In this case, the registration or the identification of the fiducial portions in a subject space may be made. Nevertheless, according to various embodiments, the user 72 may move the instrument 68 to touch the fiducial portions.

The tracking system, according to various embodiments, may track the pose of the instrument 68 due to the tracking device 66 attached thereto. This allows the user 72 to identify in the navigation space (which may include or be a portion of the subject space) the poses (including, for example, six degree of freedom information including locating and orientation) of the fiducial portions that are identified in the image 130. After identifying the positions of the fiducial portions in the navigation space, the map may be made between the subject space defined by the subject 30 in a navigation space and the image space defined by the image 130. Accordingly, identical or known locations allow for registration as discussed further herein.

During registration, the map is determined between the image data coordinate system of the image data such as the image 130 and the patient space defined by the patient 30. Once the registration occurs, the instrument 68 can be tracked with the tracking system that is registered to the image data to allow an identification and illustration of a pose of the tracked instrument 68 as an icon superimposed on the image data. Registration of the image 130 (or any selected image data) to the subject 30 may occur at any appropriate time.

In various embodiments, the image space 130 and the subject space defined by the subject 30 may be registered according to any appropriate method. As discussed above, the image to patient registration may include acquiring and/or accessing (e.g. from a memory system having the image data stored thereon) image data of a subject, such as the subject 30, with fiducials. The image data of the subject 30 may be any appropriate image data, such as image data acquired with the imaging system 80. Further, the fiducials may include the fiducial portions, as discussed above, and/or appropriate anatomical portions of the subject 30. For example the fiducial portions may include portions of the anatomy such as the spinous process of the subject 30. Nevertheless, the acquired image data may include the fiducials therein. Once the image data is acquired of the subject with the fiducials, identification of the fiducials in the image space may occur.

The identification of the fiducials in the image space may occur, as also discussed above. For example, an automatic identification of the fiducials may be made in the image data that defines the image space, such as through automatic segmentation of the fiducial portions within the image. Also manual identification and/or combination manual-and-automatic identification may be used to determine the fiducials in the image space. The combination may include the user 72 identifying one or more pixels as seed pixels and a processor executing a segmentation program based on the seed pixels.

The identification of the fiducials in a subject space and/or navigation space occurs according to generally known techniques, as discussed above. The subject space may be coextensive with the navigation space and/or may overlap. Generally, the navigation space is the volume that may be tracked with the tracking system, such as the localizer 94 and may encompass all or a portion of the subject or patient 30. The identification of the fiducials in the navigation space may occur in various manners such as moving a trackable instrument, such as the instrument 68, relative to the fiducial portions (which may also be a tracking device) and/or the spinous process. The tracking system of the navigation system 26 may track the instrument 68 and the navigation system 26 may include an input to input the portions that are the fiducial portions in the navigation space. The determination or identification of the pose (e.g. including at selected degree of freedom information including three dimensional location and orientation) of the fiducials in the navigation space may then be used to form the map, between two or more coordinate systems.

Determination of the map may be a correlation or registration of the coordinate system of the image space to the coordinate system of the navigation space relative to and/or including the subject 30. The map allows for a determined pose of a tracked portion in the navigation space to be mapped to an equivalent or identical pose in the image. Once the mapped pose is determined, the pose may be illustrated or displayed with the display relative to the image 130, such as by the superimposing of the icon **68*i* on or relative to the image 130**.

After the registration of the image space to the patient space, the instrument 68 can be tracked relative to the image 130. As illustrated in FIG. 1, the icon **68*i* may represent a pose (which may include a six-degree of freedom pose (including three-dimensional location and three-degree of freedom orientation)) of the instrument 68 can be displayed relative to the image 130 on the display 84. Due to the registration of the image space to the patient space, the pose of the icon 68*i* relative to the image 130 can substantially identify or mimic the pose of the instrument 68 relative to the patient 30** in the patient space. As discussed above, this can allow a navigated procedure to occur.

As discussed above, the imaging system 80 may include various portions such as the source 86 and the detector 88. In various embodiments, the source 86 may include one or more individual sources, such as a first source 200, a second source 204, and a third source 208. Each of the three source elements or portions 200-208, may be positioned within the source assembly 86. Accordingly, the source 86 may be understood be a source assembly including a plurality of individual source portions that may emit x-rays or energy from the source assembly 86 from each of the individual source portions 200-208 to the detector 88.

The detector 88 may be any appropriate detector and may be provided as a single detector or a single detector unit. The detector 88 may have a selected dimension 212 such as about 300 square centimeters ($cm^2$) to about 1600 $cm^2$ including about 450 $cm^2$ to about 900 $cm^2$, and further including about 625 $cm^2$ or any appropriate dimension. Generally, the detector 88 may have a dimension that is less than a subject dimension 216 of the subject 30. The subject 30, however, may be imaged by directing cones of energy, such as x-rays, from each of the plurality of source portions 200-208 to the detector 88.

Figure 2:
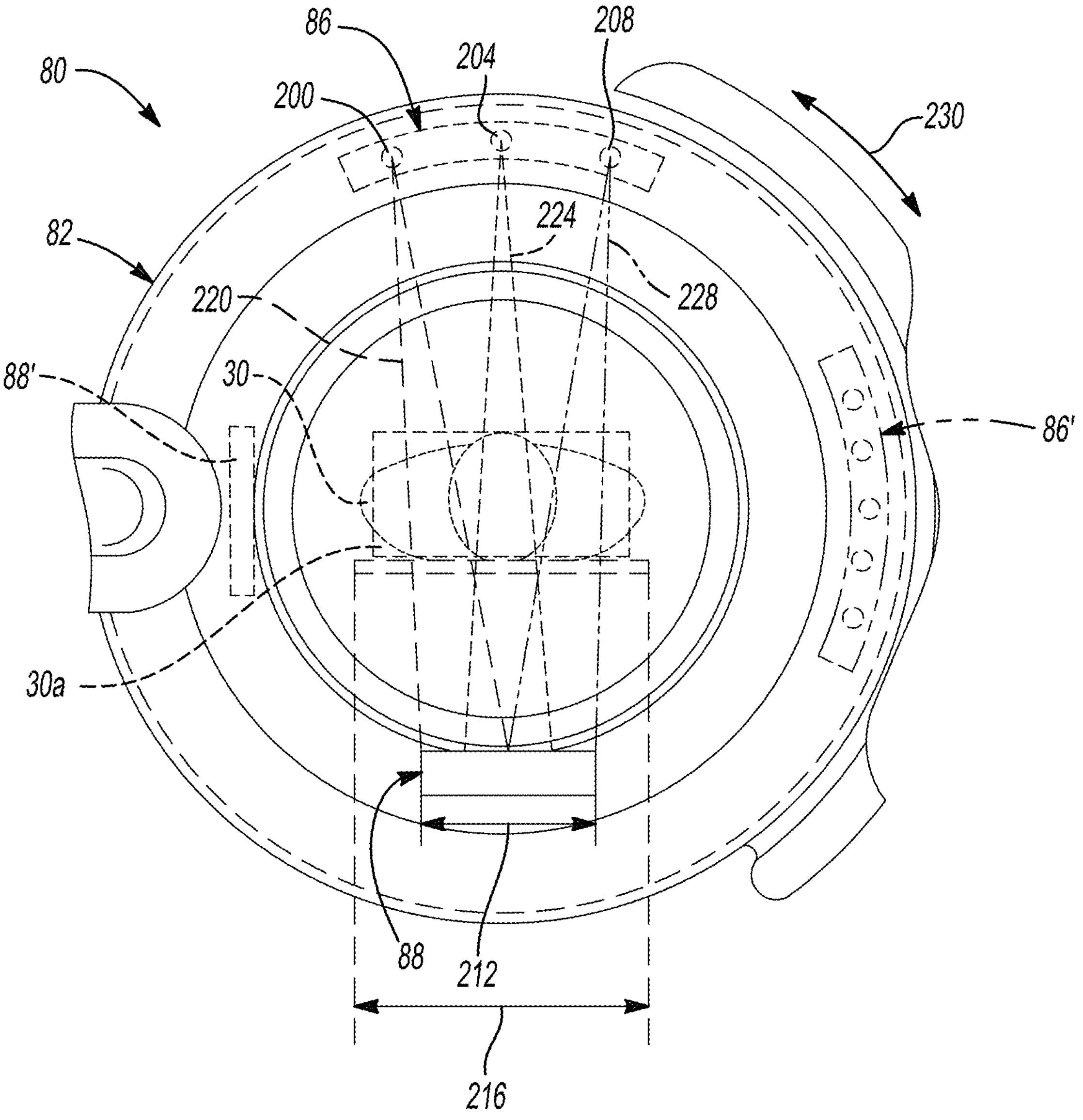
FIG. 2 is a schematic illustration of a detail of an imaging system with a source assembly having a plurality of source portions, according to various embodiments.

For example, as illustrated in FIG. 2, the first source 200 may generate or emit, for example, x-rays in a first cone 220 to impinge on the detector 88. The second source 204 may emit, for example, x-rays in a second cone 224 to impinge upon the detector 88. The third source 208 may emit, for example, x-rays in a third cone 228 to impinge upon the detector 88. Each of the cones 220-228 may pass through a different portion of the subject 30 and reach the detector 88. As illustrated in FIG. 2, each of the cones may pass through different portions of the subject 30 and allow for overlap of at least a portion of the subject through the cones 220-228 to allow for reconstruction of an entire or substantially entire image of the subject 30 and/or at least a region of interest **30*a* of the subject 30**.

The source assembly 86 and the detector 88 may move relative to the subject 30, such as generally within the gantry 82, or with other appropriate movement mechanisms, such as an area or volume around the subject 30. As illustrated in FIG. 2, for example, the image acquisition portion including the source assembly 86 and the detector 88 may move generally to a position substantially orthogonal to or 90 degrees from the first or a first position of the source assembly 86. It is further understood, however, that the source and detector assemblies 86, 88 may generally move in the direction of the double-headed arrow 230 around the subject 30. Further, the imaging system 80 may move the gantry 82 relative to the subject generally along a long axis 234 of the subject 30 and generally along an axis or parallel to an axis 238 substantially orthogonal to the long axis 234 of the subject 30. It is understood that the imaging system may also be moved parallel to both of the axes 234, 238. Further, the gantry 82 may be moved generally around the axis 238 such as in the direction of the double-headed arrow 242 and are an appropriate location relative to the subject 30. Thus the source assembly 86 may be moved in a plurality of positions and/or motions relative to the subject 30 acquire image data of the subject 30.

In various embodiments, the image sources 200-208 may be formed of "hot" emission sources such as a hot emission filament sources including rotating or non-rotating anodes. Hot emission filament sources include those such as the RAD-99B sold by, Varex Imaging Corporation, having a place of business in Salt Lake City, UT. The sources 200-208 may also be formed as substantially small or point sources such as cold emission sources including those used in various imaging platforms sold by, Micro-X Ltd, having a place of business in Adelaide, Australia. Accordingly, it is understood that the sources, including the individual sources 200-208, may be assembled into the source assembly 86 in an appropriate manner. The source assembly 86 may then be moved relative to the subject 30 to acquire image data of the subject 30. For example, the individual sources may be operated to emit an x-ray cone that passes through and/or is attenuated by the subject 30. The detector 88 then detects the x-rays that pass through and/or are attenuated by the subject 30 to generate the image data. Attenuation of x-rays may include absorption, deflection, reflection, or the like. Accordingly, attenuation may include altering and/or blocking x-rays from passing through the subject 30 and being detector 88.

Figure 3:
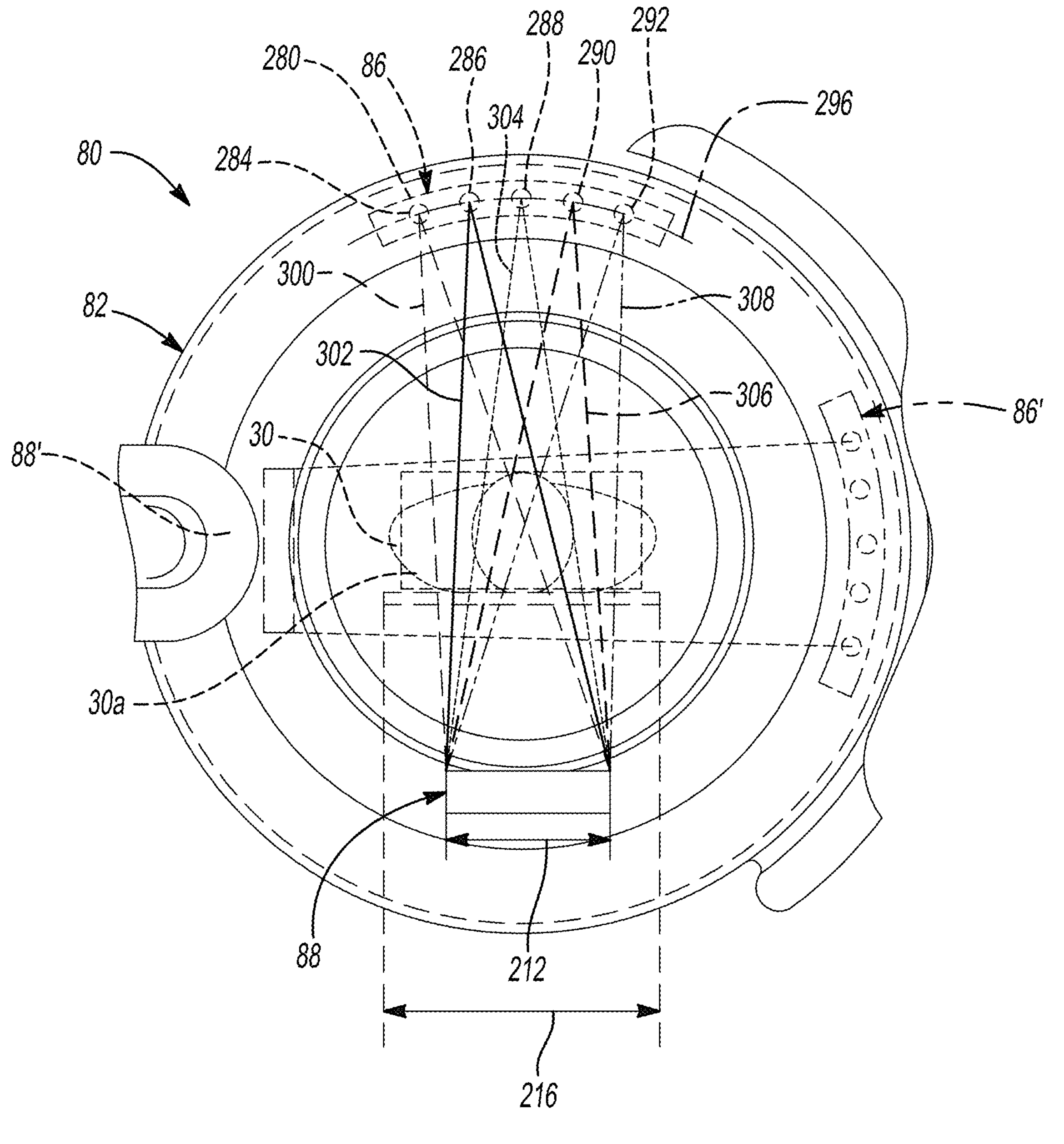
FIG. 3 is a schematic illustration of a detail of an imaging system with a source assembly having a plurality of source portions, according to various embodiments.

In various embodiments, as illustrated in FIG. 3, the source assembly 86 may include a source housing or configuration 280 that may house or encompass a plurality of individual sources or source points, such as five sources including a first source 284, a second source 286, a third source 288, a fourth source 290, and a fifth source 292. Each of the sources 284-292 may be positioned within the housing 280.

Further, the sources may be positioned within the housing 280 in a selected configuration, such as generally along an arc 296. The arc 296 may generally be around the subject 30, and may, for example, be centered on the long axis 234 of the subject. It is understood, however, that the arc 296 may be formed of any appropriate geometry relative to the subject 30, as discussed further herein.

Each of the sources 284-292 may generate a beam or emission of x-rays from the respective sources 284-292 to the detector 88. For example, the first source 284 may emit a first beam 300, the second source 286 may emit a second beam 302, the third source 288 may emit a third beam 304, the fourth source 290 may emit a fourth beam 306, and the fifth source 292 may emit a fifth beam 308. Each of the beams 300-308 may pass through the subject 30 and/or at least the region of interest 30*a* of the subject and reach the detector 88.

It is understood in various embodiments, however, that only a portion of the respective beams 300-308 may impinge or reach the detector 88, such as due to beam shaping, position of the detector 88 relative to the source assembly 86, or other configurations. Again, the detector 88 may include the dimension 212 that may be a dimension smaller than the dimension 216 of the subject and/or the region of interest 30*a*. However, due to positioning of the various sources 284-292 the respective cones 300-308 may pass through all or substantially all of the volume of the region of interest 30*a* and the single position and/or during movement of the source assembly 86. For example, as illustrated in FIG. 3, the source assembly 86 may move to a second or alternative position 86' as may the detector 88'. As discussed above, it is understood that the imaging portion, including the source assembly 86 and the detector 88 may move relative to the subject 30 in one or a plurality of motions, as discussed above.

In various embodiments, as discussed further herein, the imaging system 80 may include a plurality or multiple sources in a selected number. As discussed further herein, various numbers of sources may be included in the source assembly 86 for generating a plurality of x-ray beams or emission portions (e.g. fan, cone, or other appropriate shapes). Each of the emissions may pass through or relative to the subject 30 and/or the region of interest 30*a* and be detected at the detector 88 for generating image data. The image data may be used to generate the image 130 that may be displayed with the display device 84 and/or any other appropriate display device.

Figure 4A:
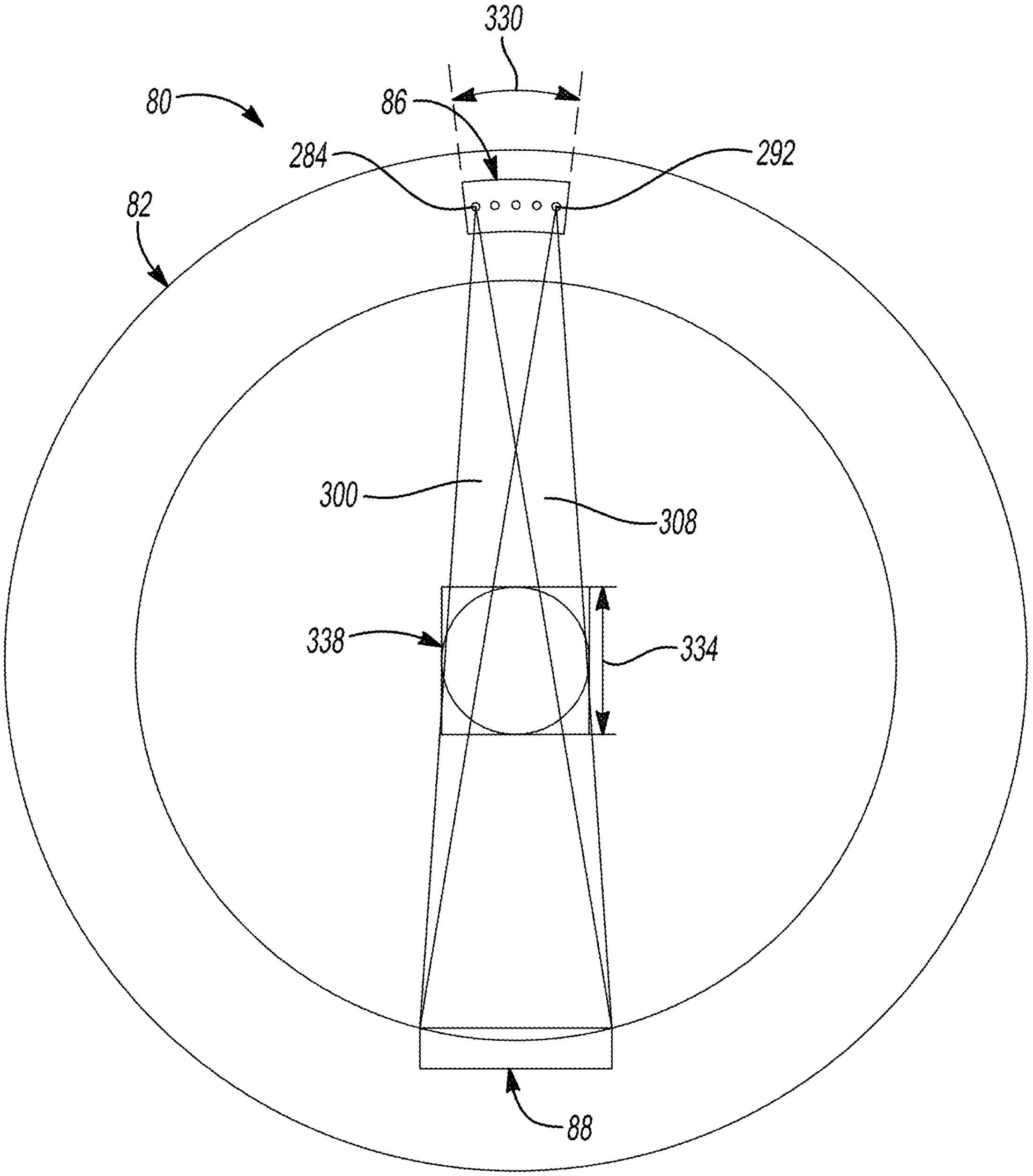
FIGS. 4A-4C are schematic illustrations of an imaging system having an imaging source with various numbers of source portions and respective possible beams and imaging volumes, according to various embodiments.
Figure 4B:
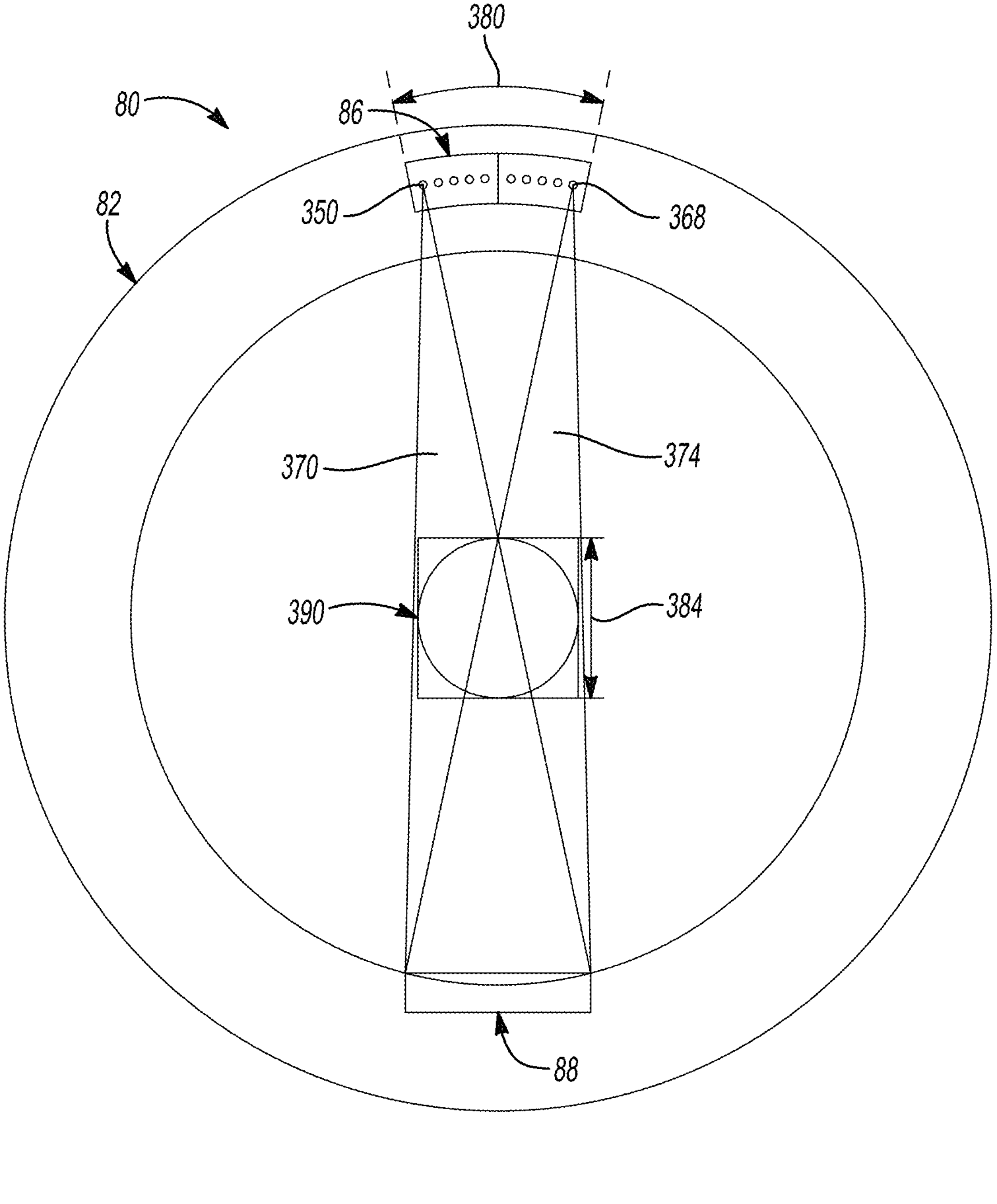
Figure 4C:
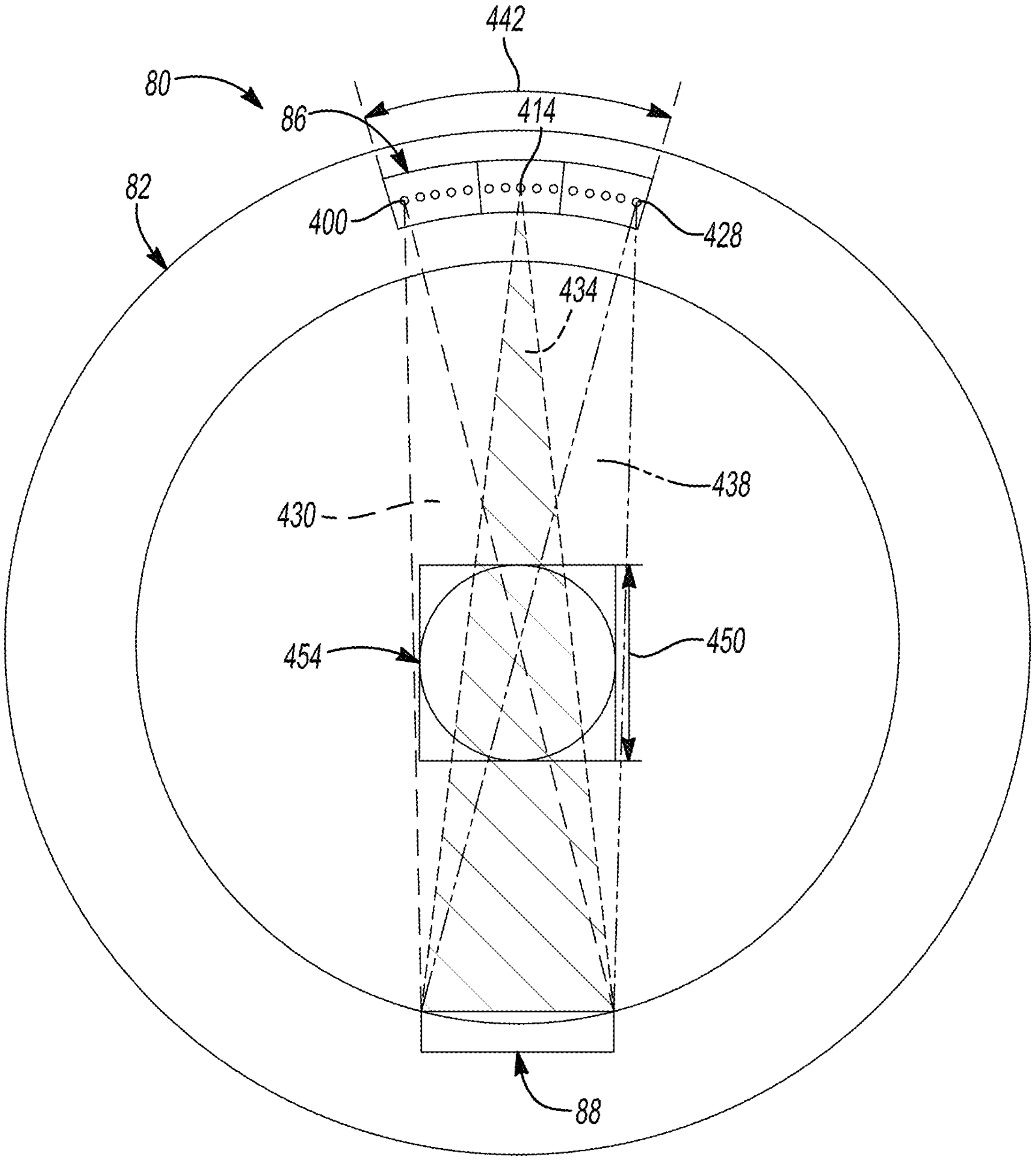

With reference to FIGS. 4A, 4B, and 4C, the imaging system 80 may include the gantry 82, or any appropriate support structure, for operation or movement of the imaging source assembly 86 and the detector 88. With initial reference to FIG. 4A, the imaging system 80 may include the source assembly 86 to have the five source portions or points 284-292, as discussed above. The source points may span a selected distance, such as an arc 330. The arc 330 may have an angular distance of about 10 degrees, including about 8 degrees to about 12 degrees. The angular distance 330 may allow the source assembly 86 including the sources 284-292, to image a volume having an edge dimension 334 of about 210 millimeters, including about 200 millimeters to about 220 millimeters. Accordingly, an imageable volume may be about 9 liter, including about 8 liters to about 11 liters.

The volume of imaging may be generated or allowed due to a conical emission or a cone emission of the beams 300-308, as illustrated and discussed above. The angular span 330 of the sources 284-292, therefore, allows for imaging of a selected volume 338. The volume imaged by the source assembly 86 may allow generation of image data of the entire volume 338 due to the passage of the cones 300-308 through the entire volume 338. In various embodiments, for example, the cones may pass through the volume and image a portion having at least a two-dimensional area of about the edge dimension 334 per side. Thus, including the sources at the angular dimension 330 can allow for imaging of the volume 338 greater than the dimension or volume of the source assembly 86.

Turing reference to FIG. 4B, the imaging system 80 may include the gantry or other appropriate support structure including the imaging assembly 86. The imaging assembly 86 may include a plurality of source portions or source points that may be numbered 350, 352, 354, 356, 358, 360, 362, 364, 366, and 368. The ten sources 350-368 may each emit a selected cone or beam of x-rays exemplary illustrated as a first beam 370 from the first source 350 and a second beam 374 form the tenth source 368. It is understood that each of the sources 350-368 may emit a selected beam and only the first and last 370, 374 is illustrated for the current discussion. The sources 350-368 may be positioned to span an angular distance or arc 380 of about 20 degrees, including about 18 degrees to about 22 degrees. Accordingly, the angular distance 380 may be about twice as great as the angular distance 330.

The angular distance 380 and the increased number of the ten sources 350-368, may allow for imaging of a region of interest or area having a side dimension 384 of about 260 millimeters, including about 258 millimeters to about 262 millimeters. The dimension 384 may be a dimension of a square area and/or a dimension of a side of a cubic volume. A cubic volume may include a volume 390 that may be imaged by the ten sources 350-368 at a selected position due to a geometry of the respective beams 370-374. As discussed above, the beams may be substantially conical and, therefore, image through the volume 390 to the detector 88 to image the volume 390. The volume 390, therefore, may include a volume of about 17.6 liters, including about 16 liters to about 19 liters. Accordingly, the angular dimension 380 of the ten sources 350-368 may allow for imaging of the volume 390 that is greater than the volume 338, as discussed above, by about 1.8 to about 2.2 times.

Again, as discussed above, the imaging system including the source assembly 86 and the detector assembly 88 may be moved relative to the volume 390. The volume 390 may include or be positioned relative to the subject 30 for imaging at least a portion of the subject 30. Thus the volume 390 may include or define a region of interest to be imaged of the subject 30. Further, as discussed above, the various cones, such as the first cone 370 and the last cone 374 may overlap to image the same portion of a volume 390 at a different perspective relative to the volume 390 and the detector 88 to ensure acquisition of image data of the entire volume 390 and/or at different perspectives, as discussed further herein.

Turning reference to FIG. 4C, the imaging system 80 may include the source assembly 86. In various embodiments, the source assembly 86 may include a fifteen point or multiple sourced emitter including individual emitters 400, 402, 404, 406, 408, 410, 412, 414, 416, 418, 420, 422, 424, 426, and 428. Each of the fifteen sources 400-428 may emit a beam of energy, such as x-rays, similar to that as discussed above (e.g. cone shaped). With reference to FIG. 4C, three cones are illustrated for simplicity of the current discussion. Accordingly, a first cone beam 430 may be emitted from the first emitter 400, a second cone beam 434 may be emitted from the eighth source 414, and a third cone beam 438 may be emitted by the fifteenth source 428.

With continuing reference to FIG. 4C, in various embodiments, therefore, each of the sources 400-428 may be equally spaced from each other within a selected angular span 442. The angular span 442 may be about 30 degrees, including about 28 degrees to about 32 degrees. The angular span 482 may allow for separation of the fifteen sources 400-428 with a center source 414 being equal distance from the two end sources 400-428, respectively. The angular span 442 may allow the respective beams 430, 434, 438 to be emitted from the source assembly 860 and pass through a region of interest and be detected by the detector 88.

The angular span 442 may allow for the beams, such as the two end beams 430, 438 to pass through a region having a dimension 450 on a side. The dimension 450 may be the dimension of a side of a square area and/or a side of a cubic volume. The dimension 450 may be about 310 mm, including about 308 mm to about 312 mm. Therefore, the dimension 450 may allow for an imaging of a volume 454 of about 29.8 liters, including about 28 to about 31 liters. The volume 454 may, therefore, define a region of interest or be used to image a region of interest of the subject 30. The volume 454, generated by the angular span 442 of the fifteen sources 400-428, may generally be about 320% greater, including about 300% greater to about 340% greater than the volume 338 defined by the angular dimension 330, as discussed above.

Thus, the angular dimension 442 (i.e. about 15 degrees) may allow for imaging of the volume 454 that may be significantly larger than a smaller angular dimension. Further, the multiple sources, including the fifteen sources 400-428, allow for imaging of the entire volume 454, as illustrated in FIG. 4C, with emissions from each of the individual sources or selected ones of the sources 400-428 to be detected at the detector 88. As illustrated in FIG. 4C, the three sources 400, 414, 428 may image the entire volume 454 including overlapping emission regions therein. Thus, the fifteen sources 400-428 may image the volume 454 and/or an area defined by the dimension 450 to acquire image data of the subject 30, as discussed further herein.

Figure 5:
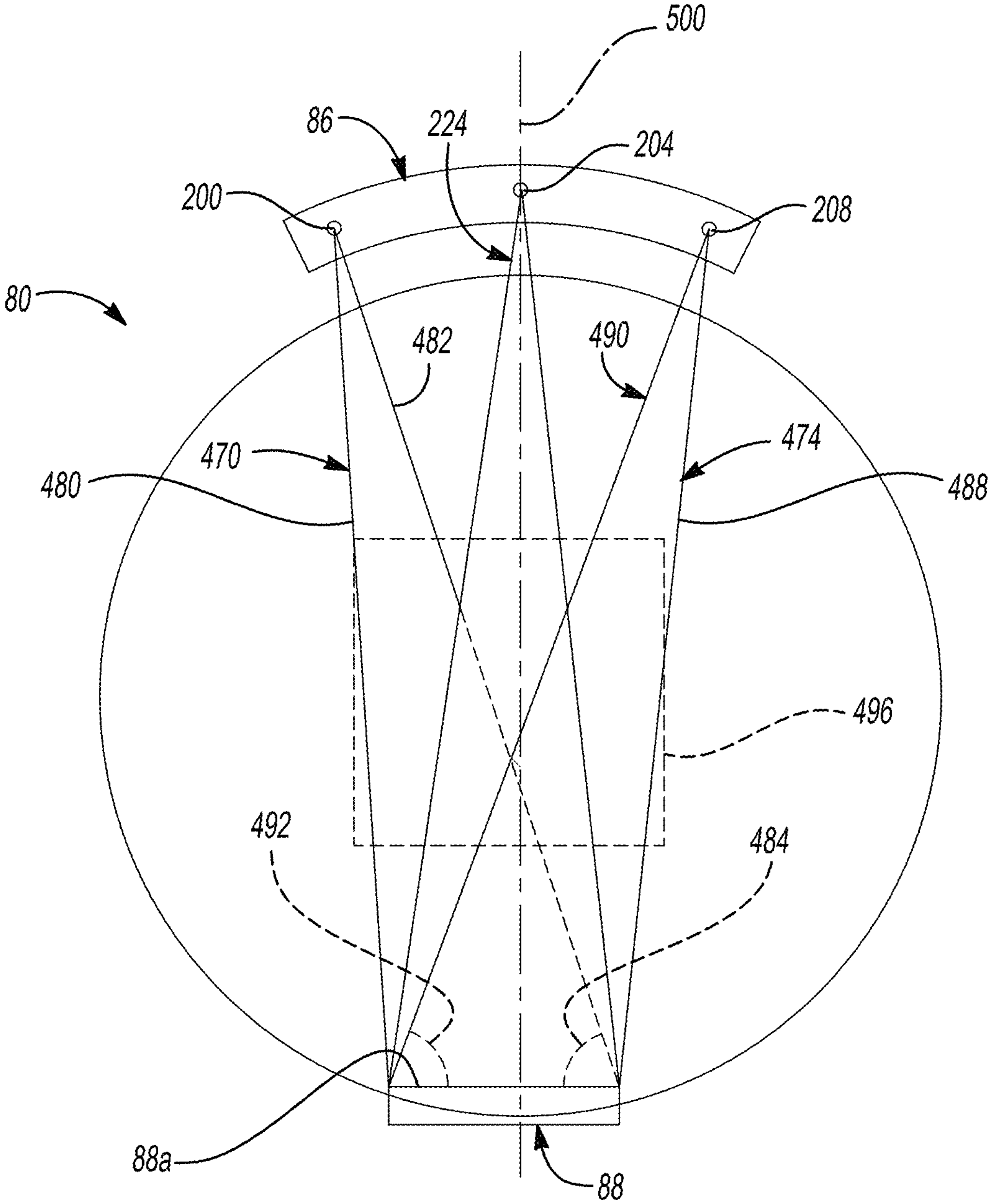
FIG. 5 is a schematic view of an imaging system with a source assembly having a plurality of source portions, according to various embodiments.

Turning reference to FIG. 5, the imaging system 80 is illustrated, according to various embodiments. The imaging system 80 may include the source assembly 86 and the detector 88. As discussed above, the source assembly may include any appropriate number of source portions, such as three source portions as illustrated in FIG. 2, or more source portions, for example as illustrated in FIG. 4C. With reference to FIG. 5, however, the source assembly 86 may include the three-source portions 200, 204, 208 for the current discussion. The source portions, may emit a fan or cone of energy, such as x-rays, in an appropriate shape or geometry. As discussed above, the geometry may include a shape that is substantially conical such as the cone 224. The geometry of the emission or beam, however, may be altered in an appropriate manner, such as with beam forming systems including filters, directors, and the like. Accordingly, in various embodiments, the emitted beam may include a beam shape such as the beam 470 from the first source portion and the beam 474 such as from the third source portion 208.

The beam shapes may include general triangular fans, such as right triangular fans, or other frustoconical shapes. For example, the first cone 470 may be a general right or nearly right frustoconical shape including a first leg 480 that may be substantially perpendicular to a surface 88*a* of the detector and a second leg 482 that may extend at an acute angle 484 relative to the detector surface 88*a*. It is understood, however, that the two legs 480, 482 may not perfectly define certain angles, as discussed above, and the shape may be a generally non-conical shape. Similarly, the second beam 474 may include a first leg 488 that may be generally perpendicular to the surface 88*a* and a second leg 490 that may extend at an acute angle 492 relative to the surface 88*a* of the detector. The beam 224 of the second emitter 204 may be substantially conical, as discussed above.

Accordingly, as illustrated in FIG. 5, the three cones or beams 470, 224, 474 may generally cover an entire region of interest 496. The shaping of the beams 470, 224, 474 from the discrete emission portion 200-208 may allow for imaging of the region of interest 496, as illustrated in FIG. 5. Further, as discussed above, the source assembly 86 may generally move around a center such as an iso-center, relative to the region of interest 496, as discussed above. Accordingly, the source assembly 86 and the detector assembly 88 may move to acquire image data at different positions relative to the region of interest 496. Thus, the volume or area of acquisition being that of the region of interest 496 may be greater than that acquired with the single source point.

Further, the source assembly 86 may be generally positioned symmetrically about a center through the region of interest 496 relative to the detector 88. For example, a perpendicular line or axis 500 extending from the surface 88*a* of the detector 88 may generally extend through the center surf point 204. Each of the two end or edge source portions 200, 208 may be substantially equal distant, such as along an arc, from the center source point 204. The source assembly 86, including the multiple sources 200, 204, 208 may be formed or positioned substantially symmetrically relative to the detector 88. Including the source assembly 86 being positioned symmetrically relative to the detector 88 may allow for acquisition of image data of the region of interest 496.

Figure 6A:
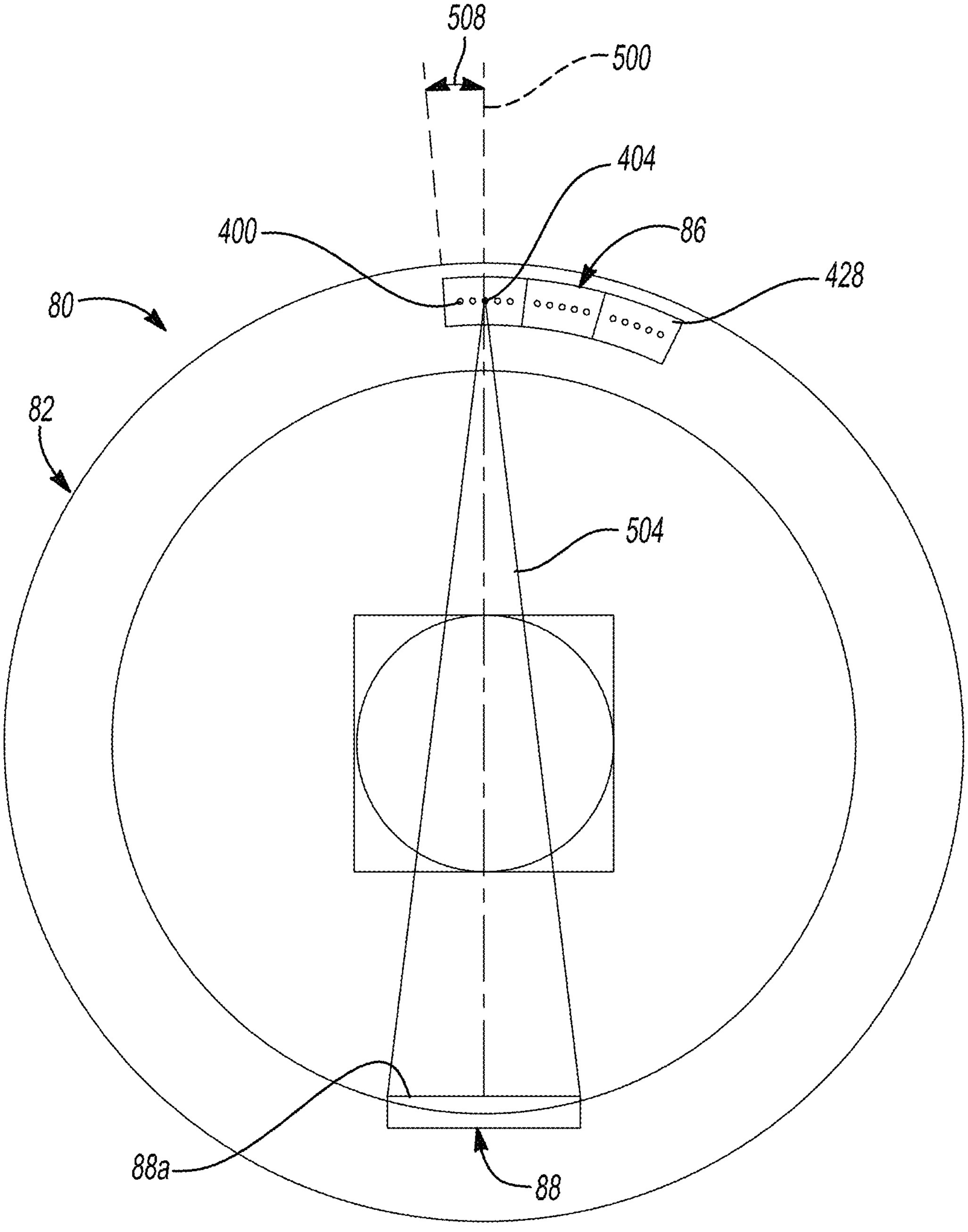
FIGS. 6A and 6B are schematic illustrations of imaging systems with source assemblies having a plurality of source portions, and illustrative projections from selected source portions relative to an imaging volume.
Figure 6B:
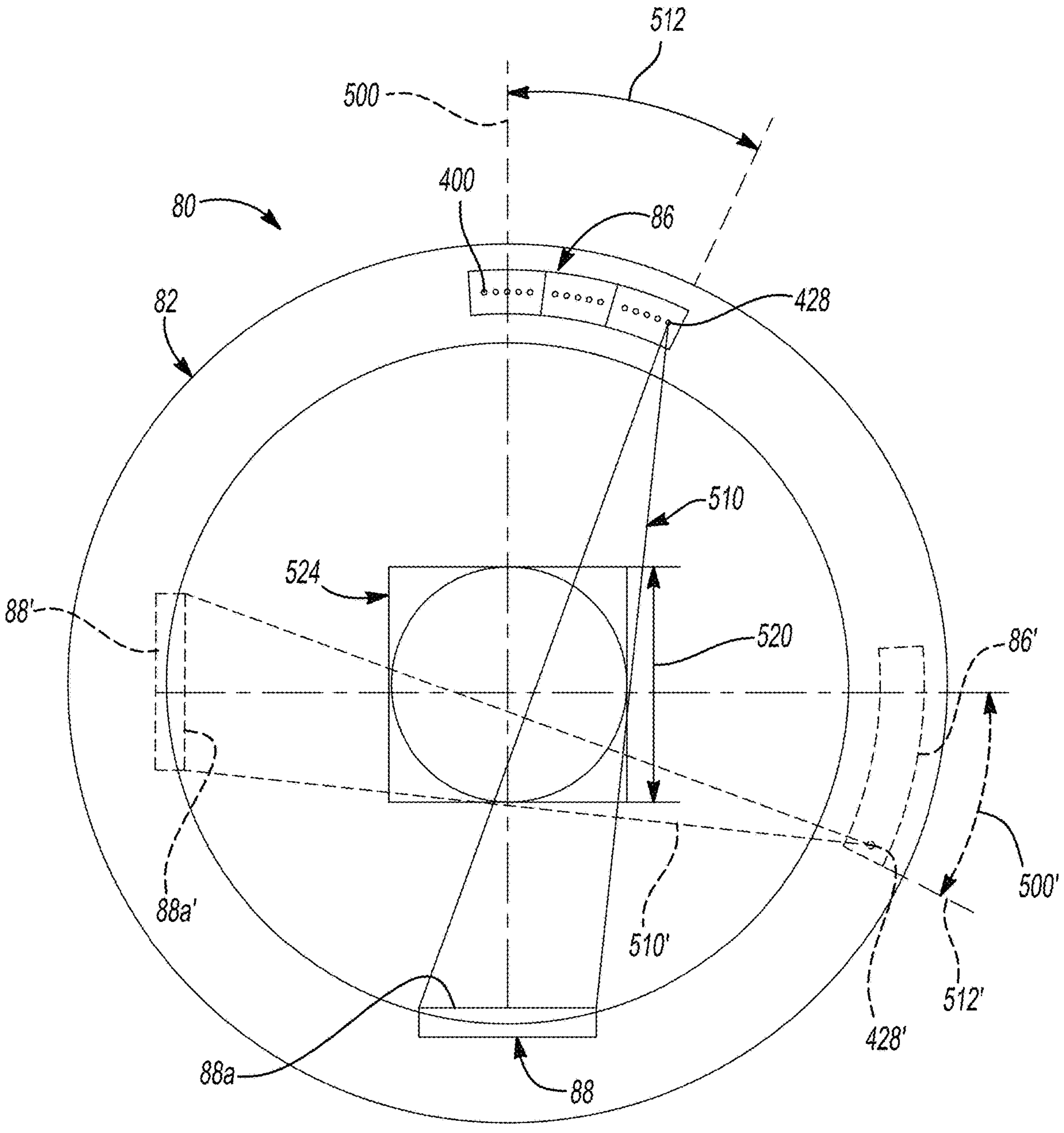

Turning reference to FIGS. 6A and 6B, the imaging source assembly 86 is illustrated in the imaging system 80 relative to the detector 88. As discussed above, the detector 88 may include an upper detecting surface 88*a*. The detector surface 88 may generally be planar or substantially planar such that a normal line or axis 500 may be defined relative thereto. Generally, the axis 500 may extend from the center of the detector surface 88*a*. Accordingly, a ray or beam may project from a source substantially along the axis 500 and be detected by the detector 88.

The source assembly 86 may be positioned relative to the detector, for example, as illustrated in FIG. 5 where the sources 200-208 are substantially symmetrical around the axis 500. In various embodiments, however, as illustrated in FIGS. 6A and 6B, the detector assembly 86 may include the 15 source portions 400-428 that are positioned substantially non- or anti-symmetrically relative to the detector 88 and the axis 500. Generally, the anti-symmetrical source assembly includes the source portions such that a first number of the plurality of source portions are positioned on a first side of a line or plane extending from the detector and a second number of the plurality of source portions are positioned on a second side of the line extending from the detector such that the second number is greater than the first number.

For example, as illustrated in FIG. 6A, the third source point 404 maybe positioned substantially on the axis 500. Therefore, the source point 404 may generally be positioned on the axis 500 and emit radiation generally perpendicular to the detector surface 88*a*. A beam 504 emitted by the source 404 may be substantially conical, as discussed above. The first source 400 may be offset from the axis 500 a selected angle, such as an angle 508 of about 5 degrees. The first source 400, therefore, may emit a beam that may not be in a shape of a regular cone or at least include a regular cone that contacts the surface 88*a*. Thus, the first source 400 may be positioned at an angular displacement from the central access 500 that is perpendicular to the surface 88*a*.

With continuing reference to FIG. 6A and additional reference to FIG. 6B, the fifteenth source 428 may emit a beam 510. The beam 510 may be different or include different geometry from the beam 438, as discussed above in FIG. 4C. Various beams emitted by the sources may include non-regular conical geometries. The non-regular conical geometries may be formed due to selected filters or beam shaping components associated with the source assembly 86. Further, the beam 510 may include the beam portion that is substantially regularly conical but includes a frustoconical shaped portion that contacts or is detected by the detector 88.

Accordingly, the detector 88 that includes the detector surface 88*a* may have the central axis 500 that extends there from. The fifteenth source 428 may be about an angle 512 relative to the central axis 500. The source assembly 86, therefore, may be substantially anti-symmetrical as the first source 400 is about 5 degrees off the central axis 500 and the fifteenth source 528 is about 25 degrees off the central axis 500. Therefore, the 15 sources are not symmetrically placed relative to the central or perpendicular axis 500 but are, rather, offset relative thereto. Thus, the beam 510 emitted by the fifteenth source 428 may be a generally non-conical or a frustoconical shape that is detected or emitted toward the detector surface 88*a*.

As illustrated in FIGS. 6A and 6B, the volume or area through which the beam may be emitted at a selected new position, therefore, may be a dimension 520. The dimension 520 may be a side dimension of a generally regular shaped square area or cubic volume. It is understood, however, that the dimension 520 may be of an appropriate edge dimension. Nevertheless, the dimension 520 may be of a volume 524 that maybe defined or operated in as a region of interest of the imaging system 800. The volume 524, therefore, maybe about 64 liters, including about 62 liters to about 66 liters. Thus the dimension 520 that maybe about 400 millimeters, including about 380 millimeters to about 410 millimeters, may allow for imaging for a selected volume 524 within the imaging system 80.

The imaging system 80, as discussed above, may also be operated to image the subject 30 within the volume 524 through movement of selected portions of the imaging system 80. For example, the anti-symmetrical source assembly 86 may be rotated around the volume 524, such as substantially annually within the gantry 82, to ensure that beams from the source points 400-428 pass through the volume 524 to be detected by the detector 88. The source assembly 86, therefore, may also be moved in the various configurations or shapes, as discussed above, to allow for image data acquisition of the volume 524. The subject 30 may be positioned entirely within or at least partly within the imageable volume 524 to allow for acquisition of image data of the subject 30 by operation of the imaging system 80.

With continuing reference to FIG. 6B, for example, the source assembly 86' and the detector assembly 88' may be rotated approximately 90 degrees (as shown in phantom) relative to the initial position illustrated in FIG. 6B (in solid). The fifteenth source 428' may emit the beam 510' to include a substantially similar geometry as the beam 510, as discussed above. The beam 510' may be emitted by the fifteenth source 428' and be detected at the detector surface 88*a*. The axis 500 extends substantially from the middle and perpendicular to the detector surface 88'*a* and pass through or relative to a portion of the source assembly 86'. The fifteenth source 428' may be positioned at the angular distance 512 relative to the axis 500. Accordingly, the fifteenth source 428' may be able to be positioned relative to the detector 88 even when rotated relative to a first position, as illustrated in FIG. 6B. The source assembly 86', therefore, may acquire image data of the volume 524 at selected positions relative to the volume 524, including a substantially orthogonal positions and/or other appropriate angular displacements of this source assembly 86' from an initial or first position.

Figure 7A:
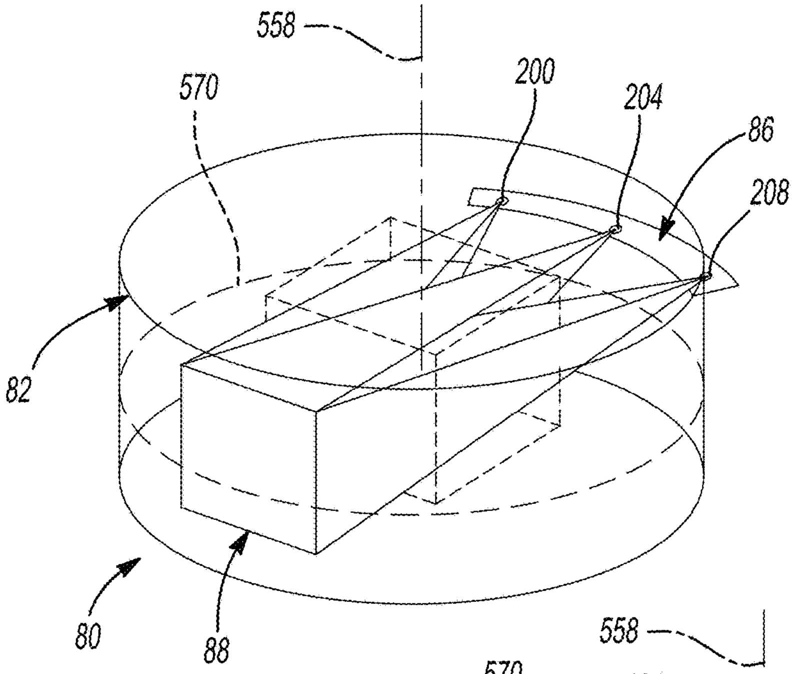
FIGS. 7A-7C illustrate imaging beams emitted by a source assembly having a plurality of source portions at selected positions of the source assembly relative to an imaging volume.
Figure 7B:
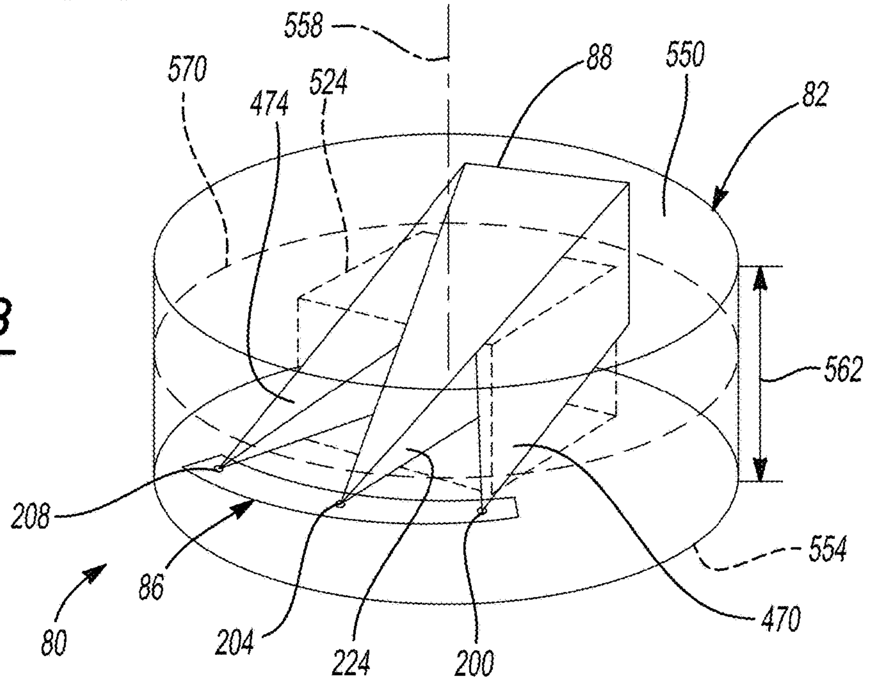
Figure 7C:
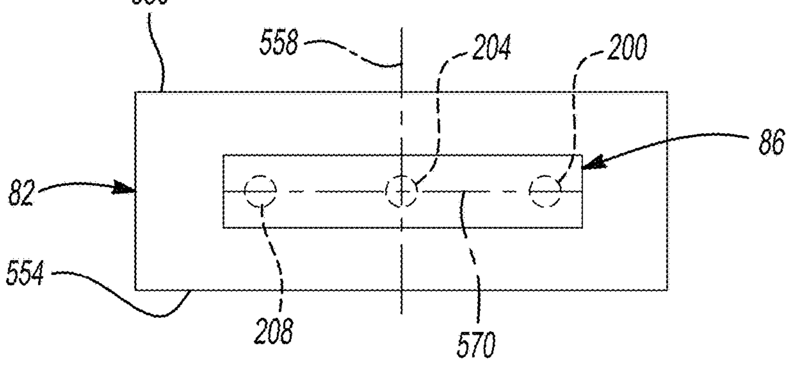

Turning reference to FIG. 7A, 7B, and 7C, the imaging system 80 may include the source assembly 86, as discussed above, including a plurality or multiple source portions. As exemplary illustrated in FIGS. 7A and 7B, the source assembly 86 may include the three source portions 200-208. Each of the respective source portions 200-208 may generate conical and/or frustoconical beams, as discussed above. Accordingly, for example, the sources 200-208 may emit the beams 470-474, as discussed above. The beams 470-474 may be shaped with appropriate filters or beam forming portions, according to various embodiments. The source assembly 86, therefore, may also be moved within the gantry 82, as discussed above.

In various embodiments, the source assembly 86 may be substantially centered or positioned in a middle between a first edge or end 550 of the gantry 82 and a second end 554 of the gantry 82. The gantry 82 may define a volume, such as a substantially total volume, between the two ends 550-554. The two ends may be generally spaced along a central or long axis 558 that may extend through the gantry 82. The axis 558 may be a generally Z direction or movement of the gantry 82 and may be generally be aligned or parallel with the long axis 234 of the subject. The gantry 82, therefore, may generally include or have a depth 562 of a selected dimension, such as about 0.5 meters to about 2 meters. The depth may allow for positioning of various components, such as the source assembly 86 and the detector assembly 88 within the gantry 82. Various electronics and other mechanisms may also be provided within the gantry depth 562.

With further reference to FIG. 7C, the sources 200-208 may be aligned in a plane that may be parallel with one or both of the sides 550-554 of the gantry 82 and/or substantially perpendicular to the axis 558 through the gantry 82. The sources 200-208, therefore, may lay on a plane and along an arc or an arc that is a portion of a circle that is on a plane within the gantry 82. Each of the sources emit the respective beams 470-474 from the respective sources 200-208 to the detector 88 from the same plane within the gantry 82 and substantially perpendicular to the central axis 558. Thus the sources 200-208 may vie on a circle 570 that has a center at the central axis 558.

Again, the source assembly 86 and the detector assembly 88 may rotate around the axis 558 to acquire image data of a region of interest or volume, such as the volume 524 within the gantry 82. This may allow the source assembly 86 and the detector assembly 88 to be moved within the gantry 82. Further, as discussed above, the gantry 82 may move relative to the subject 30, such as by movement relative to the cart 103 relative to the subject 30.

In various embodiments, the source assembly 86 may rotate within the gantry 82, or with any other appropriate holding or mounting system, to acquire images of the volume 524. The volume 524 may, therefore, be imaged with one or more of the beams emitted by one or more of the sources within the source assembly 86. The beams may encompass or cover the volume 524 due to rotation of the source assembly 86 and the related detector 88 within the gantry 82. As illustrated in the figures, such as in FIG. 7A and 7B, the beams may cover a certain portion of the volume 524 with a greater density than other portions of the volume 524. For example, if the beams are x-ray emissions the density or amount of radiation within the volume 524 may affect image quality of the subject 30 being imaged.

Figure 8A:
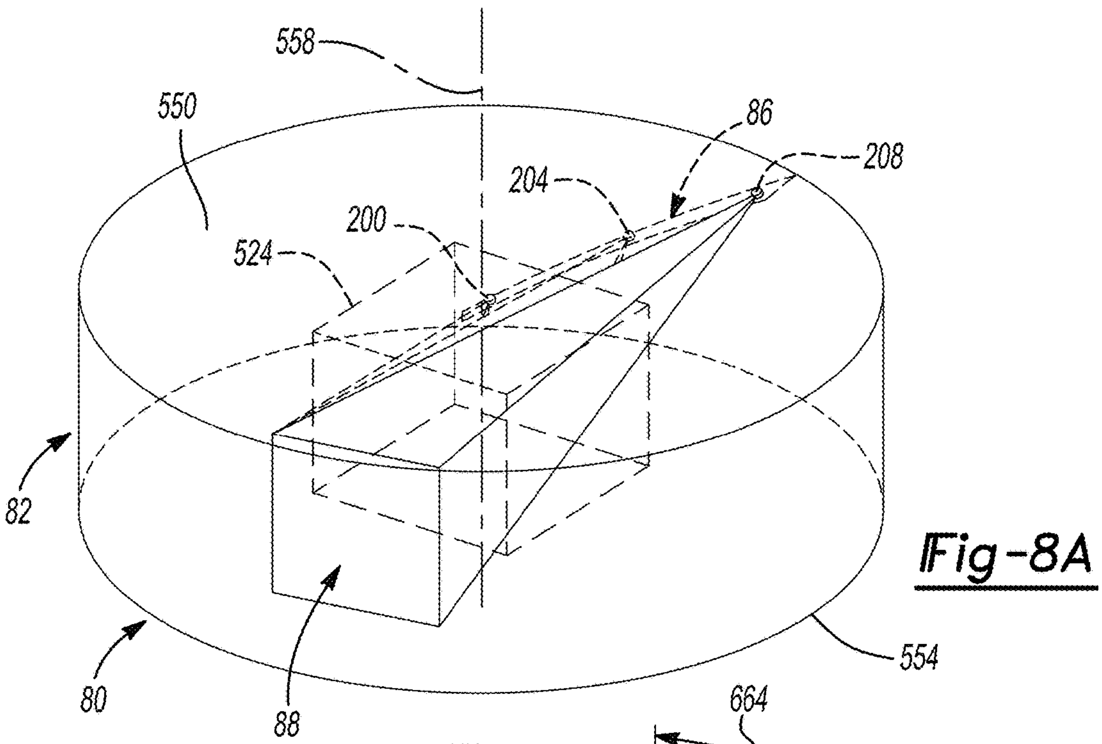
FIGS. 8A-8C are views of an imaging system having a source assembly with a plurality of source portions, positioned anti-symmetrical relative to a plane or line of the imaging system and at a plurality of positions relative to an imaging volume, according to various embodiments.
Figure 8B:
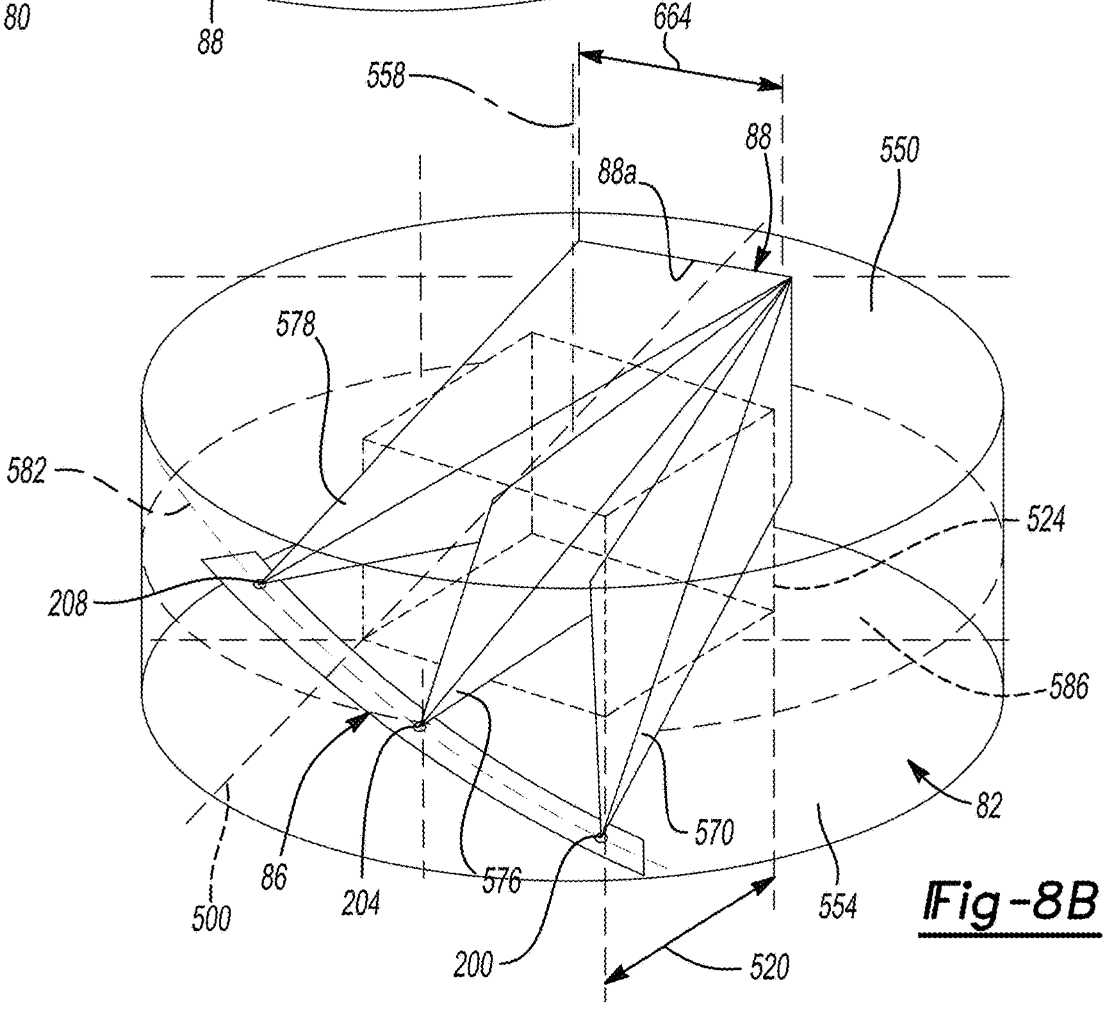
Figure 8C:
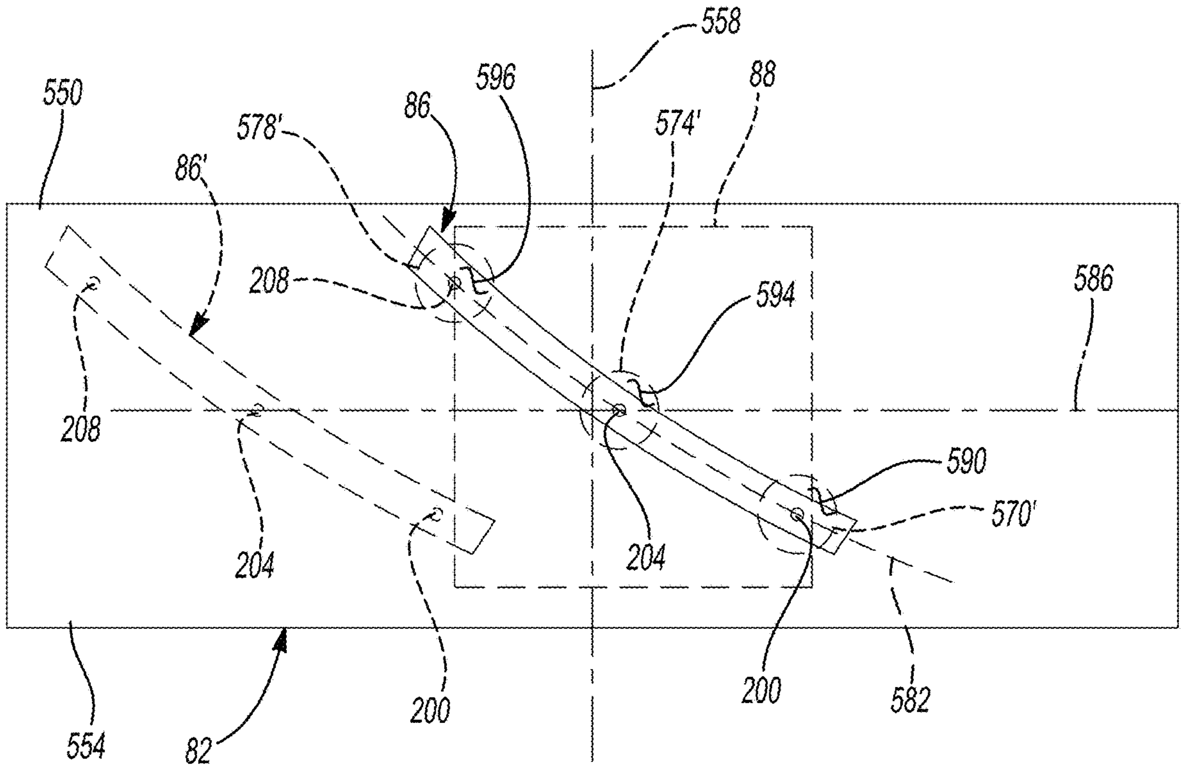

Turning reference to FIGS. 8A, 8B, and 8C, the imaging system 80 may include the gantry 82, as discussed above. As further discussed above, the imaging system 80 may include the detector 88 and the source assembly 86. The source assembly may include any appropriate number of sources, such as the three sources 200-208, as discussed above. It is understood, however, that the source assembly 86 may further include any appropriate number of sources including the 15 sources 400-428, as discussed above. The discussion and illustration of the three sources 200, 204, 208, is for ease and clarity of the current discussion. Accordingly, as illustrated in FIG. 8A, the source assembly 86 may include the three discrete or individual sources 200-208 that may emit the three beams including a first beam 570 from the first source 200, a second beam 574 from the second source 204, and a third beam 578 from the third source 208. The three beams 570-578 may be directed toward the detector 88, such as the detector surface 880 thereof. As discussed above, the detector 88 may have the detector surface **88*a* that is substantially planar and may define an axis or line 500** that extends substantially perpendicular thereto.

The source assembly 86 may be positioned within the gantry 82 and relative to the detector 88 such that the source assembly 86 and/or at least a line or arc 582 extending through the sources 200-208 is not parallel with a plane perpendicular to the axis 558 extending through the gantry 82 and/or a direction or path of rotation of the source assembly 86 within the gantry 82. As discussed above, the source assembly 86 may move in an annular path or circular path in the imaging system 80. In various embodiments, the gantry 82 may include a rail or other system to allow or direct the path of the source assembly 86 within the gantry 82. The path of the source assembly 86 may generally be substantially circular, such as generally along a circular path 586. The line or arc 582 may intersect the path or circle 586 within the gantry 82. Further, as illustrated in FIG. 8C, the line 582 through the source assembly 86, including through the sources 200-208, may extend through or intersect the outer surfaces or planes of the gantry 82.

In various embodiments, the first source 200 may be nearer to a side, such as a second side 554, than either or both of the second source 204 and the third source 208. The third source 208 may be nearer the opposite side, such as the first side 550 of the gantry 82, than either or both of the first and second sources 200, 204. The second source 204 may be between the distance of either of the first and third sources 200, 208 relative to either of the two sides 550, 554 of the gantry 82. Accordingly, as illustrated in FIGS. 8A-8C, the sources 200-208 may be positioned to extend out of a circular path or path that defines a plane within the gantry 82. Thus, a certain number of the sources may be nearer one side than certain other sources relative to a second side of the gantry. As illustrated in FIG. 8A, therefore, the beams emitted by each of the sources may include a different portion or part that may intersect the volume 524 that may be imaged with the source assembly 86 of the detector 88.

With continuing reference to FIGS. 8A-8C, but with particular reference to FIG. 8C, the off-axis or tilted orientation of the sources 200-208, such as along the line 582, may position the sources to image, such as with greater intensity, different portions of the volume 524 relative to the detector 88. As illustrated in FIG. 8C, for example, the source 200 that may emit the beam 570 may have a central or highest intensity portion 570' that may pass through and be detected by the detector 88 in a first region 590. The second source 204 that emits the beam 574 may include a higher density or central region 574' that may strike or reach the detector 88 at the region 594. Finally, the third source 208 that emits the beam 578, may include a higher density or central region 578' that may reach the detector 88 at the region 598. Accordingly, the various beams from the respective sources may reach the detector with the beam that are concentrated at different regions on the detector 88. Thus, as the source assembly 86 sweeps or moves in the path within the gantry 82, more or a greater region of the imageable volume, such as the volume 524, may be impacted or able to attenuate a region of high intensity or high density of the beam from one or more of the sources 200-208.

The source assembly 86, when angled, may move to a second source position 86' (phantom) as illustrated in FIG. 8C. Thus, the source assembly 86 may include the sources 200-208 along the line 582 that is substantially along a line or plane that is not parallel with a path of motion or circle 586 within the gantry 82.

With continuing reference to FIGS. 7A-7C and 8A-8C, the imaging system 80 may further manipulate or move the source assembly 86, in various embodiments. It is understood, as discussed above, that the source assembly 86 may be fixed in a single selected position, such as generally aligned with an axis or plane of rotation, such as within the gantry 82, or angled relative thereto. It is further understood that the source assembly 86 may be positioned in any appropriate position, such as substantially orthogonal to the movement or position plane 586, rather than simply aligned with or at a selected acute angle relative thereto.

In various embodiments, with reference to FIGS. 9A-9D, the source assembly 86 may also be selectively moved relative to the gantry 82 of the image assembly 80. As discussed above, the gantry 82 may be provided in various formats, and may generally have a first or front surface 550 and the second or back surface 554. It is understood that the gantry 82 may be a selected shape, such as a C-shape, an O-shape, or other appropriate shapes. Further, the gantry may include an openable or breakable gantry such as of an O-arm® Imaging System, as discussed above. Nevertheless, the source assembly 86 may be positioned within the gantry 82 on a selected structure, such as a rail 600. The rail 600 may carry one or more components, such as the source assembly 86. The source assembly 86, as discussed above, may extend between two ends such as a first end 610 and a second end 614. The sources, such as the three sources 200, 204, and 208, may be positioned within or held with the source assembly 86. It is understood that the source assembly 86 may include any number of the sources, including those discussed above.

The source assembly 86 may be moved on or with the rotor or rail 600 such as around the subject 30, as discussed above. The source assembly 86 may generally move in an arc such as in an arcuate or angular motion 586. The motion or path 586 allows for the source assembly 86 to be rotated or moved around the subject 30, such as for acquisition of image data at various locations relative to the subject 30, as discussed above. The source assembly 86, however, may also be movable relative to the rotor or rail portion 600.

In various embodiments, for example, the source assembly 86 may rotate about an axis 620. The axis 620 may extend through the source assembly 86, and such as through an axle or pin 624. The axle 624 may mount or hold the source assembly 86 relative to a drive assembly or system 628. The drive assembly 628 may include various portions or systems, such as an electrically powered motor, which may include a separate motor or selected separate motor for moving the source assembly 86.

The drive assembly 628 may be powered and controlled to rotate the source assembly 86 around the axis 620, such as generally in the direction of the double headed arrow 632. The source assembly, therefore, is understood to be able to rotate in either or both directions relative to or around the axis 620. The source assembly 86, therefore, may be rotated from a position that is substantially aligned between the two ends 610, 614 with the path or plane of movement 586, as illustrated in FIG. 9B.

The drive assembly 628 may be operated or controlled with the control assembly 96 to move or control movement of the source assembly 86. As discussed above, the imaging system may move relative to the subject 30, including movement of the gantry 82 along or relative to a Z or long axis 234 and/or a vertical axis 238 relative to the subject 30 and may also be rotated or tilted relative to the selected axes and/or the cart 103, such as in the direction of the double headed arrow 242. The source assembly 86, therefore, may also be moved in concert with movement (e.g. simultaneously and/or at a selected time delay relative to) of other portions of the imaging system 80, such as the gantry 82 and/or the rotor 600. The source assembly 86, therefore, may be positioned to a selected position and/or rotated around the axis 620 while the rotor 600 rotates around the subject 30, such as generally in the direction of the plane or double headed arrow 586.

Figure 9A:
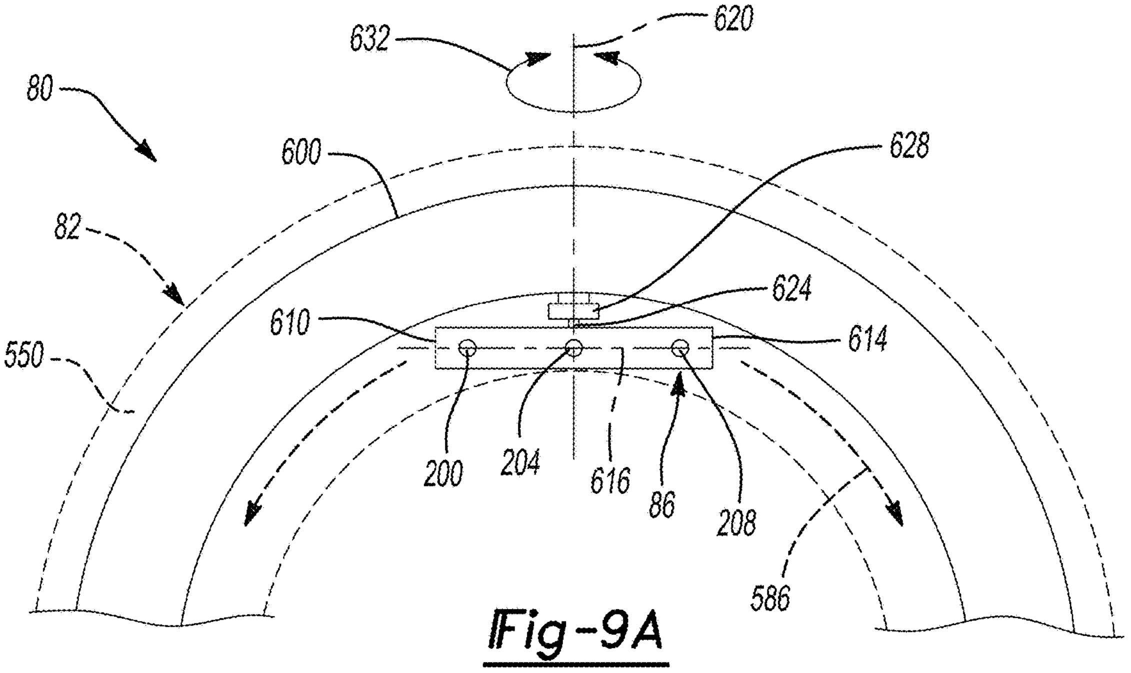
FIGS. 9A-9D are schematic views of an imaging system having a source assembly movable relative to a gantry, according to various embodiments.
Figure 9B:
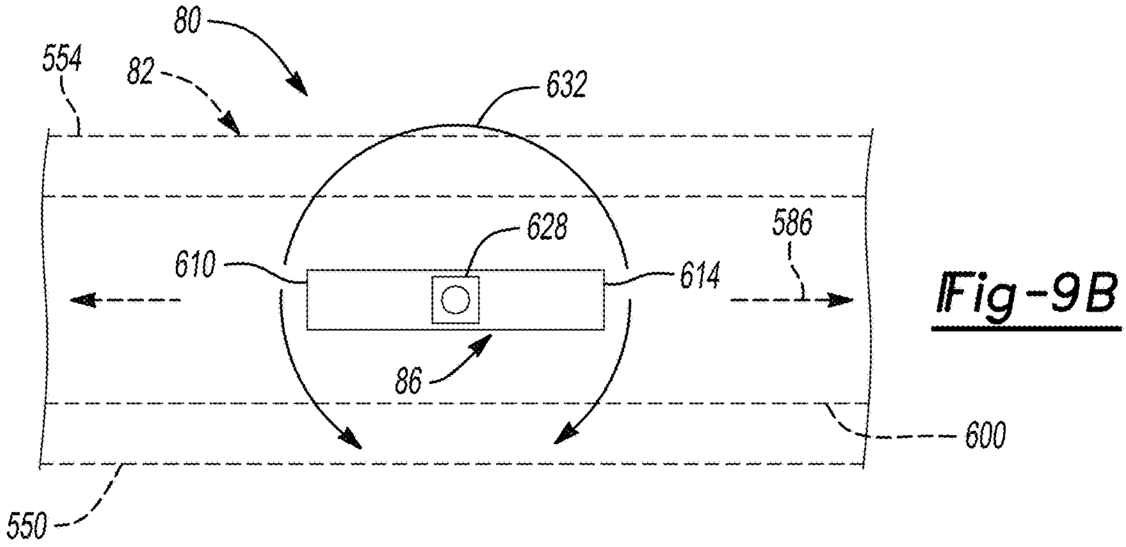
Figure 9C:
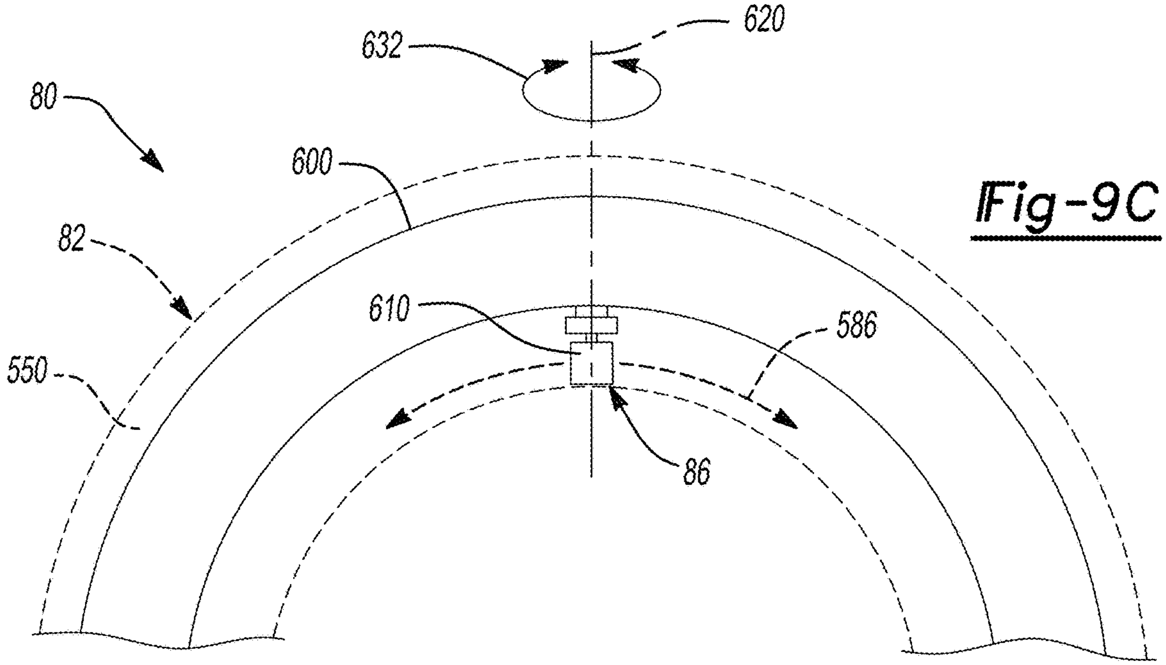
Figure 9D:
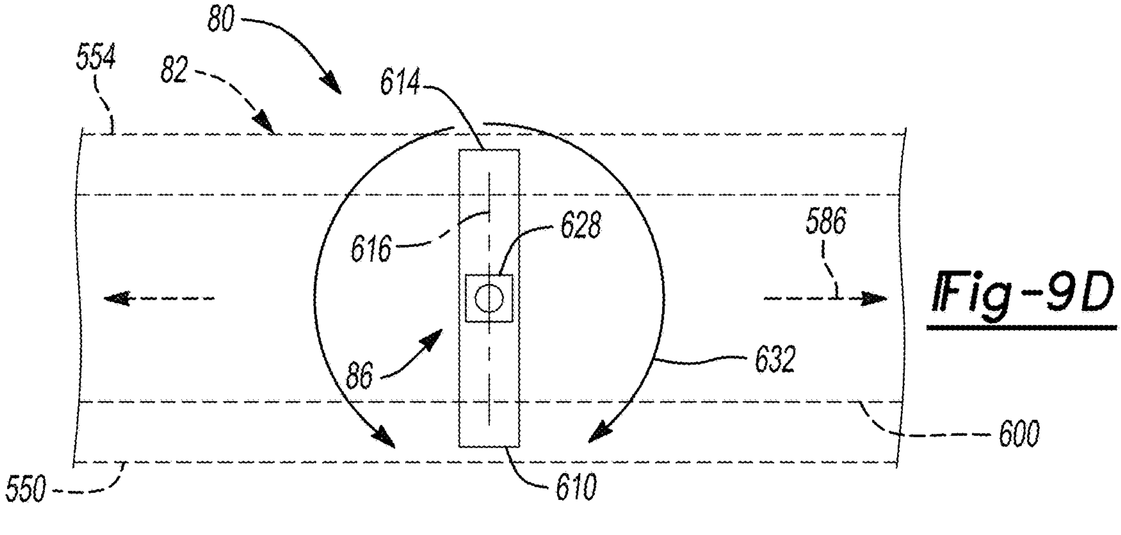

With continuing reference to FIGS. 9A and 9B, and additional reference to FIGS. 9C and 9D, the source assembly 86 may be rotated such that it is substantially perpendicular to the direction or movement plane 586. As discussed above, the source assembly 86 may extend between the ends 610, 614, such as generally along a long axis 616. The long axis 616 of the source assembly 86 may be in line or parallel to the movement axis or plane 586. As illustrated in FIGS. 9C and 9D, however, the long axis 616 of the source assembly 86 may also be substantially perpendicular or orthogonal to the axis or plane 586. Accordingly, the source assembly 86 may move around the axis 620 in the direction of the double headed arrow 632 to position or move the source assembly 86 to a position that is substantially orthogonal to the movement plane or axis 586. It is understood that the source assembly 86 may be positioned at any position between the aligned position and the orthogonal position, as illustrated in FIGS. 9A and 9C. The source assembly 86 may also be rotated around the subject 30 and/or during rotation of the source assembly 86 around the subject 30. Thus the illustration of the aligned or the orthogonal positions, as illustrated in FIGS. 9A and 9C, respectively, is merely exemplary of two possible positions of the source assembly 86.

As the source assembly 86 may be moved by the drive system 628, the source assembly 86 may be automatically moved according to selected instructions, such as those executed by the control assembly 96. The user 72 may select one or more imaging features or characteristics. The imaging system 80 may then be operated to collect subject image data for generation, such as reconstruction, of images, such as the image 130, for display on the display device 84 or other appropriate display devices.

Figure 10A:
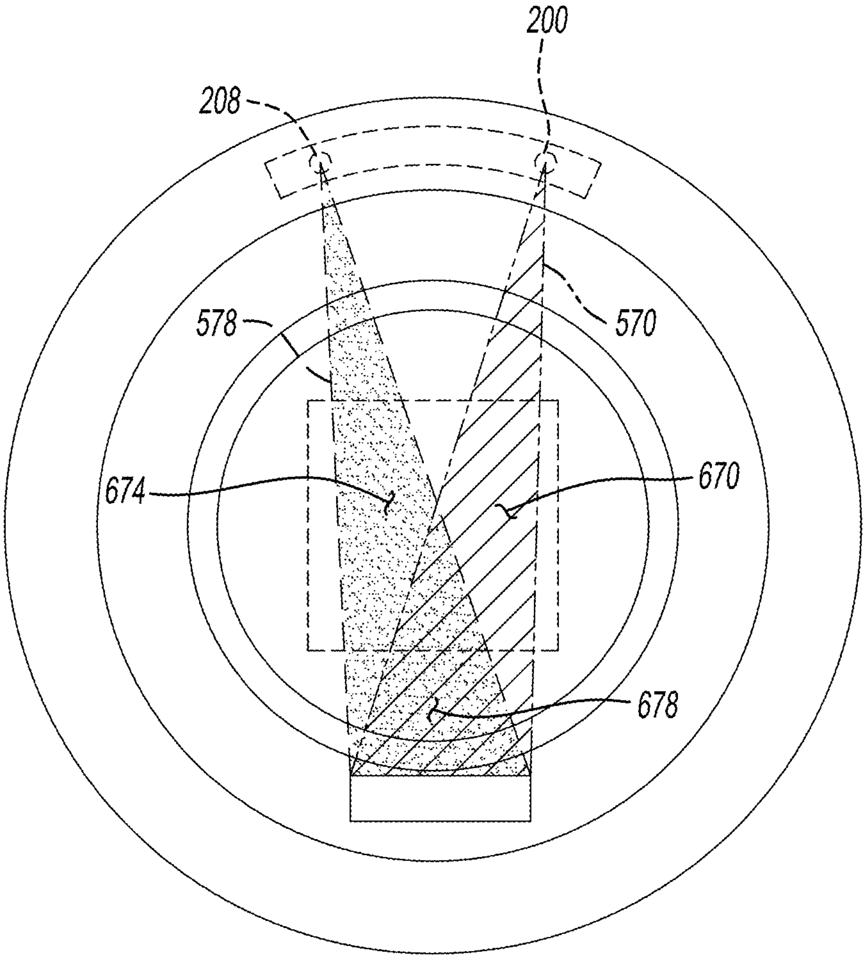
FIGS. 10A and 10B illustrate and imaging system having a source assembly with a plurality of source portions and selected overlap of selected beams, according to various embodiments.
Figure 10B:
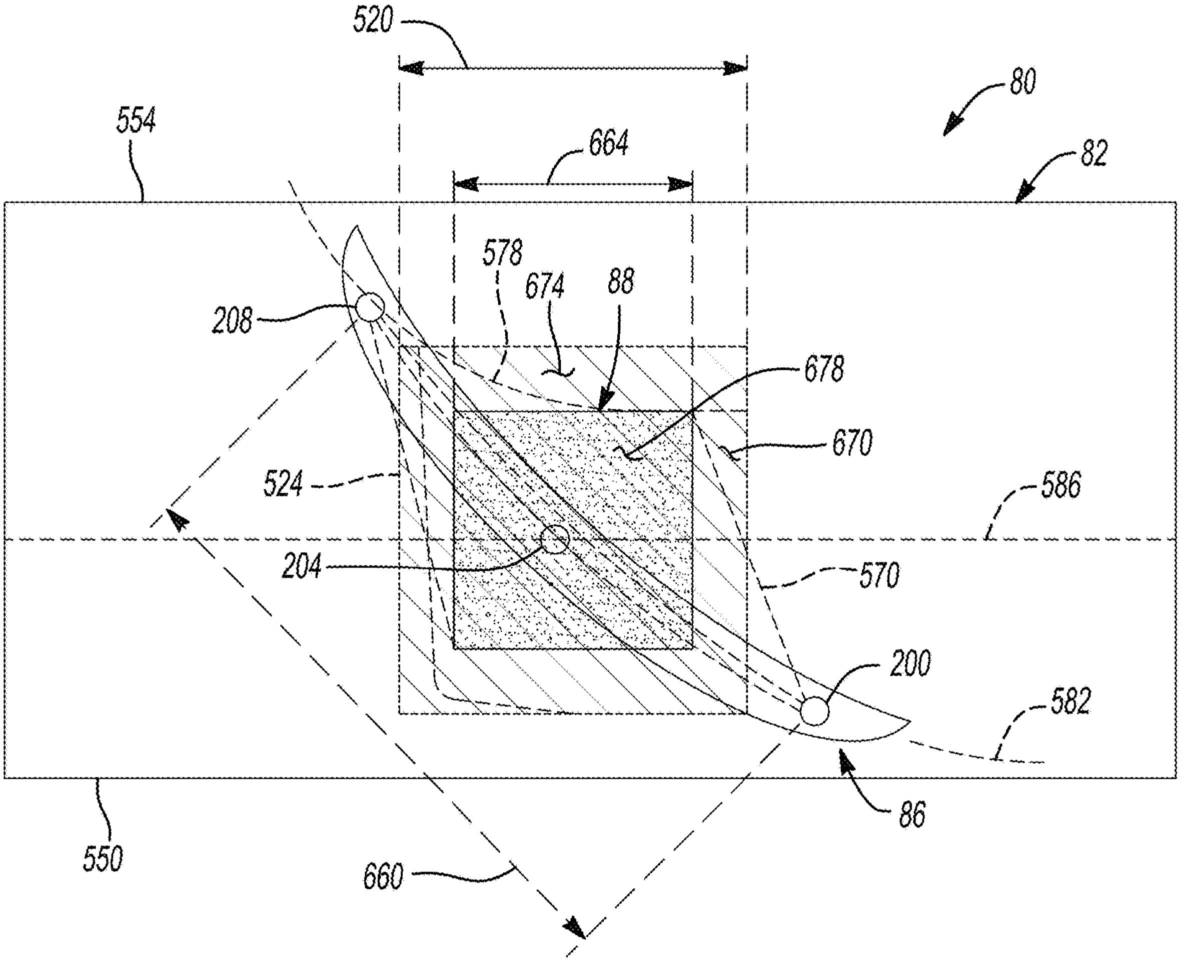

With continuing reference to FIGS. 8A-8C, and additional reference to FIG. 10, the imaging system 80 may include the source assembly 86 that includes one or more sources, such as the three sources 200, 204, 208. It is understood, however, that any appropriate number of sources may be provided in the source assembly 86, including such as that discussed above.

As illustrated in FIG. 10, the source assembly 86 may be positioned such that the sources 200-208 are aligned along a line or arch that has a long axis 582. The source assembly 86 may move in a path 586, such as within the gantry 82. The path 586 may generally be an angular path, such as within the gantry 82 that is angular. It is understood, however, that the path or plane 586 may be any appropriate path and generally may be defined by the geometry of the imaging system 80. Nevertheless, as illustrated in FIGS. 8B and 10, the source assembly 86 may be positioned to cross or extend through the plane 586 between the two surfaces or sides 550, 554 of the gantry 82.

Accordingly, as illustrated in FIG. 10, the image assembly may include the first source 200 near the first side 550 and the third source 208 near the second side 554. The second source 204 may be positioned between the first and third source 200, 208, as illustrated in FIG. 10. Generally, a dimension 630 may be defined between the first source 200 and the third source 208 the dimensions 660 may be a generally linear dimension however, it is understood, that the sources may be positioned along an arc or a curve that has a center positioned outside or defined outside of the source assembly 86. Nevertheless, the dimension 660 may define a linear dimension between centers or edges of the two sources 200, 208 that may or may not extend through any other sources, such as the second source 204.

The dimension 660 may be a dimension that is greater than other dimensions, such as an edge dimension 664 of the detector 88 and/or the dimension 520 of the region of interest 524. As discussed above, the region of interest 524 may be a region of interest or an imageable region or volume. Accordingly, the dimension 520 may be one side of a cube that defines the region or image of interest or imageable volume 524. Nevertheless, the dimension 660 between the sources 200, 208 may be greater than either of the dimensions 664 and/or 520.

The respective sources may each emit respective beams, such as the first source 200 emitting the first beam 570 and the third source 208 emitting the third beam 578. As illustrated in FIG. 8B the two respective beams 570, 578 may be emitted from the respective sources 200, 208 and pass through selected portions of the imageable volume 524 and contact the detector 88. The beams 570, 578 may be selectively emitted and/or shaped from the source assembly 86 to pass through the volume 524 and contact or be detected by the detector 88. It is understood that the other sources may also emit different beams, however, discussion of the two beams 570, 578 is for clarity of the current discussion and the other sources may also emit other beams to pass through other portions of the volume 524.

As illustrated in FIG. 8B and FIG. 10, the first beam 570 may emit from the source 200 pass through the volume 524 and be detected by the detector 88. The beam 570 may pass through a first portion 670 of the volume 524 and be detected at the detector 88. The third beam 578 may pass through a second volume 674 of the volume and be detected by the detector 88. Accordingly, the two beams 570, 578 may extend or pass through different portions of the volume 524 and/or may overlap or both pass through a selected overlap region 678. Various imaging reconstruction techniques may be used to generate or acquire an image of a length 520, such as an axial length along the axis 234 of the subject 30. The dimension 520 may be greater than the dimension 664 of the detector 88. Therefore, a length greater than a length of the detector 88 may be imaged with the source assembly 86 positioned as illustrated in FIG. 10. Similarly, the volume 524 may be imaged with the source assembly 86 that is greater than a volume that includes the dimension 664 of the detector 88.

Accordingly, the image assembly 80 may acquire image data of a subject, such as the subject 30, greater than dimensions of the detector 88. For example, a single pass or projection through the volume 524 may collect image data of a length or along a length of about 20 centimeters (cm) to about 30 cm, including about 25 cm. This dimension may be greater than a dimension that may be imaged in a single projection with the source assembly aligned with the path 586 is illustrated in FIG. 7C, which may be about 10 cm to about 20 cm, including about 15 cm. Both of the projections may be acquired on the detector 88 having a dimension 664 (e.g. side dimension) that is about 30 cm. Accordingly, the alignment or positioning of the source assembly 86 including the sources 200-208 positioned relative to the path or plane 586, may allow for acquisition of projections that include a dimension greater than one allowed due to the alignment of the source assembly 86 in line with the path or plane 586.

Figure 11:
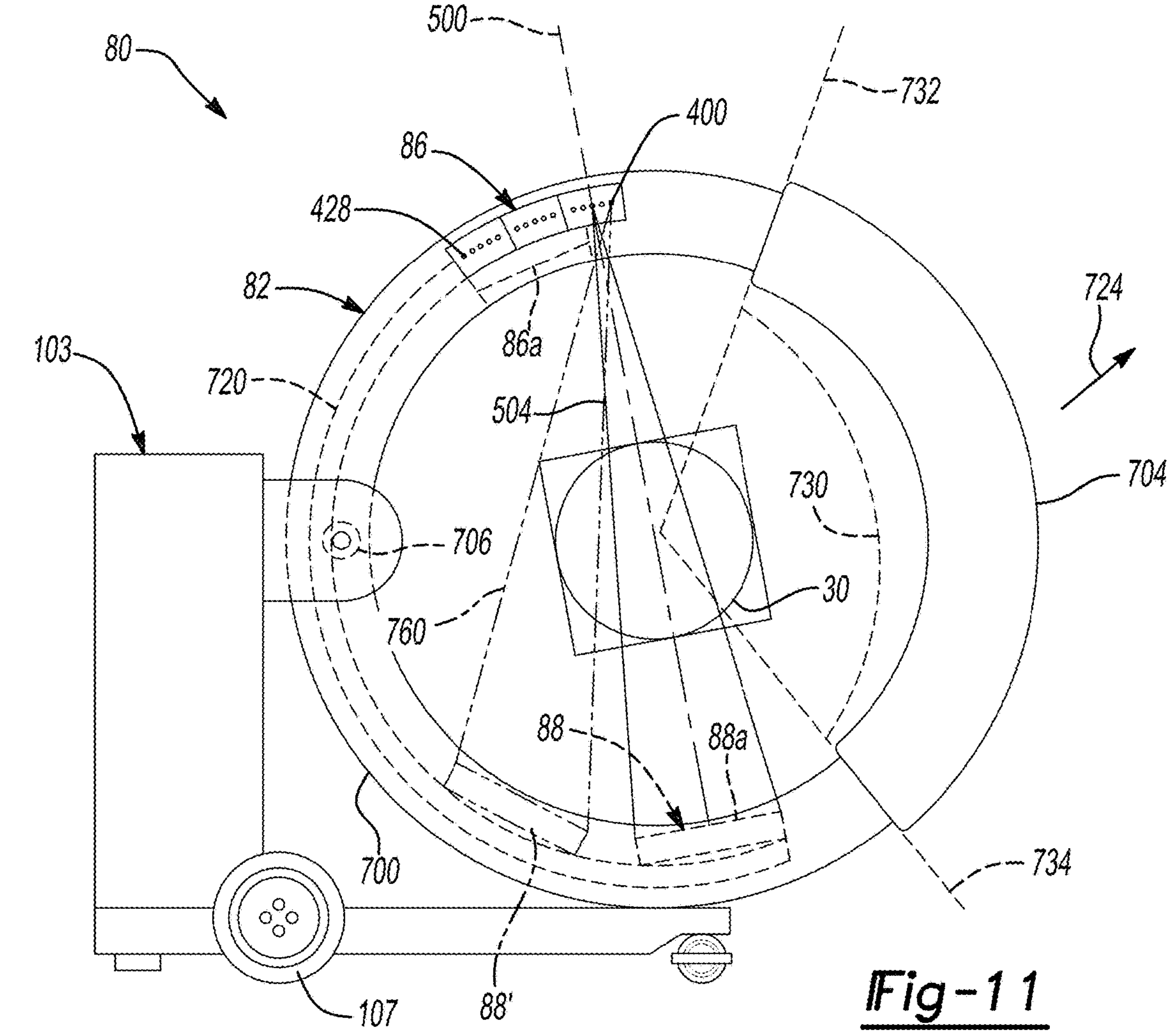
FIG. 11 is a schematic view of an imaging system having a source assembly and a plurality of source portions with a geometry of imaging an imaging volume, according to various embodiments.

Turning reference to FIG. 11, the imaging system 80 may include various geometries, as discussed further herein. As discussed above the imaging system 80 may include the gantry 82 that may be positioned in a generally annular or "O" shaped configuration. The gantry 82 may be connected to the cart 103 that may allow for movement of the imaging system 80 in two various locations and during the selected procedures. In various embodiments, as discussed above, the imaging system 80 may include one or more mobile portions, such as the wheel 107 or a plurality of wheels to support the cart 103 and move the imaging system 80, as selected. The gantry 82, as is understood, may include a fixed or main portion 700 and an open or breakable portion 704. The fixed portion 700 may be fixed to the cart 103 in a selected position and/or at a selected fixed point 706. The fixed portion 700, therefore, may generally define a minimum extent or size for the imaging system 80. The imaging system 80, as discussed above, may include the source assembly 86 and the detector assembly 88.

As schematically illustrated in FIG. 11, the source assembly 86 and the detector assembly 88 may be fixed or positioned to a rotor 720. The rotor 720 may be movable within the gantry 82 to various positions. As discussed above, the imaging system 80 may allow for movement of the source assembly 86 and/or the detector 88 relative to imageable volume or subject 30. The source assembly 86 and the detector 88 may be fixed to the rotor 72 at a selected position and/or a selected geometry. As illustrated in FIG. 11, the source assembly 86 may be asymmetrically or anti-symmetrically positioned relative to the detector 88. In other words, the detector 88 may include the detector surface or face 88*a* from which extends an axis or line 500. The axis 500 may be substantially perpendicular to the surface 88*a*. The source assembly 86, however, may be positioned such that a majority, such as a first portion 86*a* is positioned to one side or a selected side, such as an internal arc relative to the detector 88, with the rotor 720. Accordingly, a large or open area may be provided for access of the subject 30 within the gantry 82.

The breakable portion or open portion 704 may be moved relative to the fixed portion 700. For example, the door 704 may move generally in the direction of arrow 724 to allow access to an interior or within the gantry 82. The position of the source assembly 86 relative to the detector 88 with the rotor 720 may allow for a large opening such that it may be defined by an angle 730 between two lines or planes 734 and 738. The angular or arcuate dimension 730 may be a selected dimension, such as about 60 degrees to about 300 degrees, including about 90 degrees to about 180 degrees. The rotor 720 and the associated source assembly 86 and detector assembly 88 may allow for the open area of the gantry 82 to allow for efficient or ease of access to an area within the gantry 82 for positioning a subject 30. The imaging system 80, however, may be able to move the rotor 720 relative to the subject 30 for acquiring selected image data relative to the subject 30, as discussed above, and further herein.

The positioning of the source assembly 86, including the plurality of source portions, such as the 15 source portions 400-428, may allow for the gantry 82 to include various portions, such as the door 740 that allows for the opening arc 730. The opening or open arc 730 may be usable during an acquisition of image data of the subject 30, such as during a selected procedure, in an efficient manner. The imaging system 80, in various embodiments, is moveable relative to the subject 30 with the cart assembly 103 and the rotor 720 may be used to move the selected source assembly 86 and the detector assembly 88 relative to the subject 30 for acquiring image data of the subject 30.

The imaging system 80, as discussed above, may include the source assembly 86 and the detector 88. The source assembly 86 and the detector 88 may be fixed in a respective position with the rotor 720. The rotor 720 may then be moved within the gantry 82, as discussed above, for example as illustrated in FIG. 11. In addition, the detector assembly 88 and/or the source assembly 86 may move relative to the rotor 720. For example, a rail and a motor system may be provided to move one or both of the source assembly 86 and/or the detector assembly 88 relative to the rotor 720 and/or relative to each other. In various embodiments the detector 88 may move from a first position, as illustrated in FIG. 11, to a second position 88' (phantom), as also illustrated in FIG. 11. The detector 88' may detect x-rays emitted by one or more of the sources, such as the source 400 that may emit a beam (e.g. cone beam) 760 to be detected by the detector 88'. The imaging assembly 80, therefore, may be provided to move various portions therein relative to one another for imaging of a selected subject, such as the subject 30.

Further the source assembly, as discussed above, may include a plurality of individual sources. In various embodiments, the source assembly 86 may include the 15 source portions or points 400-428. The various source points may be operated in a selected manner for various imaging techniques of the subject 30. In other words, different source portions of the multiple source portions may be operated differently in the single source assembly, according to various embodiments.

Figure 12:
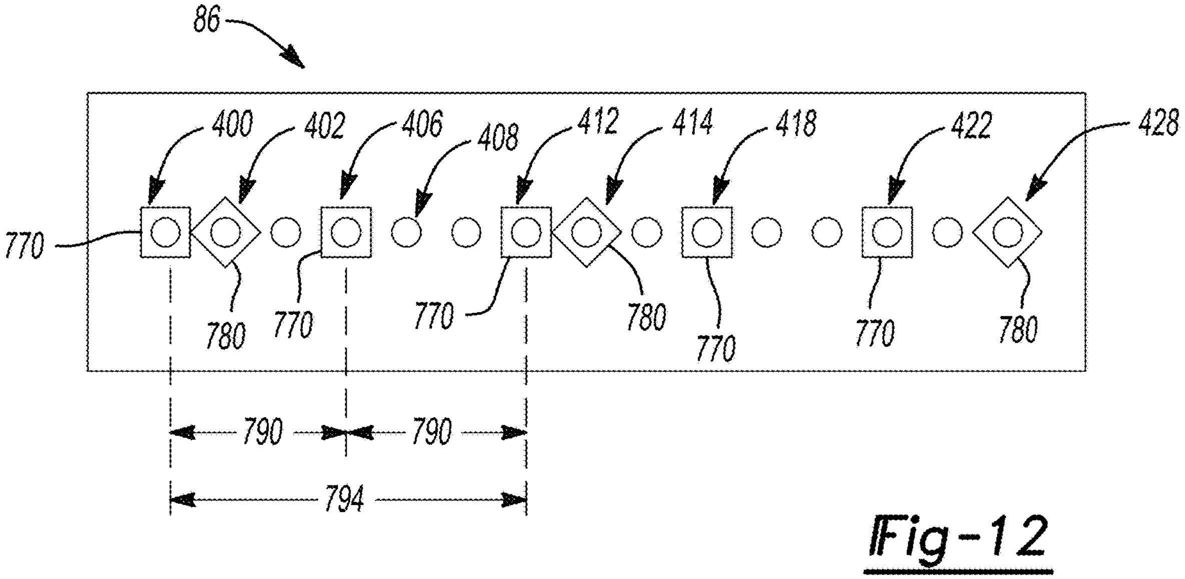
FIG. 12 is a schematic illustration of a source assembly having a plurality of source portions with selected characteristics of one or more of the source portions, according to various embodiments.

In various embodiments, with reference to FIG. 12, the source assembly 86, including the 15 sources 400-428, may be provided for imaging the subject 30 with various filters or filter assemblies. For example, as exemplary and schematically illustrated in FIG. 12, selected ones of the sources, such as the source point or portion 400, 406, 412, 418 and 422, may all have a selected filter 770. The filter 770 may be provided or have selected features or characteristics to use or enhance a selected imaging modality. For example, the filter portions 770 may be operable to assist in fluoroscopic imaging of a subject. Fluoroscopic imaging may be assisted by a filter assembly, including a selected material such as aluminum or copper and/or collimator to focus the x-ray beam to a particular region of interest. Accordingly, the filter assembly 770 may be provided in a fixed manner and/or movable manner relative to the selected source portions 400, 406, 412, 418, 422 to assist in fluoroscopic imaging of the subject 30. The filter assembly 770, therefore, may be used to enhance or operable to enhance selected imaging modalities relative to the subject 30 to assist in imaging the subject 30. The other source points of the source assembly 86 need not have the filter portion 770 and may provide a selected beam, such as a broad or broad spectrum beam.

Moreover, it is understood that of the plurality of the sources 400-428, other selected sources may include individual or different filter portions. For example, a filter portion 780 may be provided on selected ones of the sources such as the source 402, 414, and 428. The source portion 780 may assist in a selected imaging modality, such as in a dual energy imaging modality of the imaging system 80. In various embodiments, for example, the filter assembly 780 may assist in selecting or limiting the emission from the source 402 to a selected spectrum. The emission from another one of the sources, such as the source 408, may be of a different energy. Accordingly, the two sources 402, 408 may be used in the single source assembly 86 to assist in generating or collecting dual energy images of the subject 30.

As discussed above, the source assembly 86 may be positioned relative to the subject 30 for imaging the subject 30. Thus, the two source portions 402, 408 may be powered or used to emit x-rays in close time to ensure or assist in collecting dual energy image data with substantially little (e.g. less than about 0.1 seconds) time between acquisition of image data at two different energies. The source assembly 86, therefore, may be operated to acquire dual energy images of the subject 30.

It is understood that the various filter portions 770, 780 are illustrated schematically and may be understood to include any selected type of filtering mechanism or material. Further, the filter portions 770, 780 may assist in collimating or directing the beam from any of the selected sources. In various embodiments, the filter portions 770, 780 may include selected materials such as lead, copper, or other materials. Further, the source portions may include selected shapes, such as narrow slits, pin holes, or the like to assist in selecting or generating a selected beam shape.

Further, the source assembly 86 may be operated to collect or emit from any one of the selected sources in a selected sequence. As discussed further herein, the source assembly 86 may be operated to emit from any one or more of the source portions simultaneously, sequentially, or in a selected pattern. In various embodiments, for example, while the rotor 720 rotates about the subject 30, the sources including the filter portions 770 may be operated in sequence such that a selected number of projections are acquired of the subject 30 while only using selected one or more of the source portions at any one emission/projection.

Alternatively, or in addition thereto, at substantially any and/or each position of the source assembly 86 relative to the subject 30 (e.g. such as in a rotation of the source assembly relative to the subject 30), a plurality of the sources having substantially similar characteristics may be operated. By acquiring image data of the subject with two or more of the sources at a single position of the source assembly 86, a stereoscopic or perspective acquisition of the subject may be made as the sources are offset from one another by a selected distance. For example, the source 400 is a distance 790 from the source 406 although both of the sources 400 and 406 may include substantially similar characteristics emission or imaging characteristics. Further the source 406 may be the distance 790 from the source 712. The source 400 may be a distance 794 from the source 412. The distance 794 may be twice the distance, either linearly or angularly, between source 412 and the source 400. Accordingly different perspectives relative to the subject 30 may be acquired with imaging characteristics that are substantially similar, but at different positions or perspectives, in a single image projection.

In various embodiment, each of the sources may be powered substantially simultaneously at each selected position of the source assembly 86 relative to the subject 30. As discussed herein such simultaneous acquisition may allow for a dual perspective image or image data acquisition of the subject 30 at a single position of the source assembly 86. The duel perspective may allow for registration to additional or other image data of the subject 30.

With continuing reference to FIGS. 1-12, and additional reference to FIGS. 13A, 13B, 13C, and 13D, the imaging system 80 is illustrated. With specific reference to FIGS. 13A-13D, the imaging system 80 is schematically illustrated to include the source assembly 86 that is movable around a gantry 82. The gantry 82 is illustrated schematically as including only the inner annular portion, but is understood to include an annular portion that may encompass or define the volume through which the source assembly 86 may be moved along with the detector assembly 88. The detector assembly 88 and the source assembly 86 may be connected to a rotor, as discussed above. Further, the gantry assembly 82 may include any selected configuration, such as a “C” and/or an “O” configuration or the like. Further, the imaging system 80 may include the various portions and features, as discussed above, including the cart 102, a breakable or opening portion of the gantry 82, or other selected portions. Nevertheless, the discussion relating to FIGS. 13A-13D include the schematic illustration of the imaging system 80 for clarity of the current discussion.

The imaging system 80 including the source assembly 86 may include, for example, the 15 source point assembly including the sources 400-428. During operation of the imaging system 80, the source assembly 86 may move around the gantry 82 generally in the path 586, as discussed above, and in either or both directions of the double-headed arrow 810. Various portions of the imaging system 80 may also move relative to the subject 30 and/or the cart 103, and therefore the direction of the double headed arrow 810 is to illustrate only one possible movement of the source assembly 86 during an imaging procedure. Again, the source assembly 86 may move along a selected path, such as that understood by one skilled in the art, to acquire image data of the subject 30. Further, the detector 88 may also move relative to the source assembly 86 and/or with the source assembly 86 and the gantry 82 to acquire the image data. The selected movement in the direction of the double-headed arrow 810, again is for clarity of the current discussion.

Figure 13A:
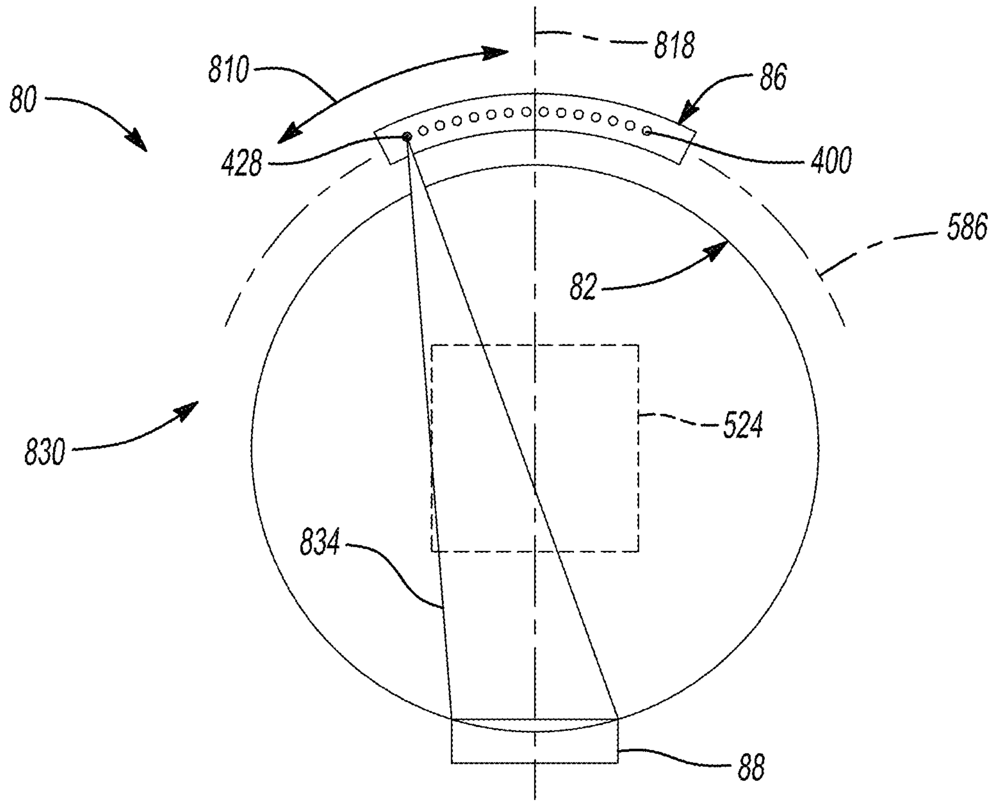
FIGS. 13A-13D are schematic illustrations of an imaging system with a source assembly having a plurality of source portions and movement of the source assembly relative to an imaging volume, according to various embodiments.

In various embodiments, therefore, for example as illustrated in FIG. 13A, the source assembly 86 may be at a first position relative to the region of interest or imageable volume 524 such as generally along a reference or central axis 818. It is understood, for example, that the gantry 82 may be positioned relative to a surface and the reference axis 818 is merely for discussion purposes here. As discussed above, therefore, the source assembly 86 may move in the direction of the double-headed arrow 810 along the path 586 relative to the reference axis 818. In a first image data acquisition position 830, as illustrated in FIG. 13A, the source assembly 86 may be positioned relative to the detector assembly 88 and the source portion 428 may be operated to emit x-rays to be detected by the detector 88. As illustrated in FIG. 13A, the x-rays may pass through a selected path or shape, such as a selected cone or cone beam 834 through the region 524 to be detected with the detector 88.

Figure 13B:
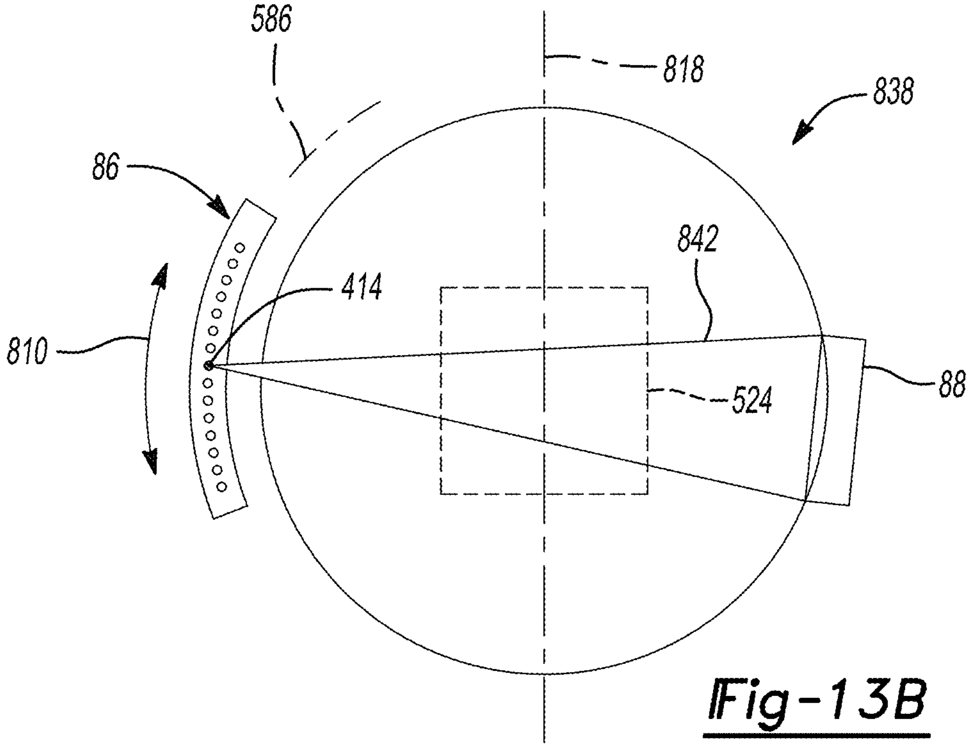

Turning reference to FIG. 13B, the source assembly 86 may move to a second or alternative position relative to the reference axis 818 as also may the detector 88. The source assembly 86 may move in the direction of the double headed arrow 810 along the path 586 to the second position or one of a selected alternative plurality of positions as illustrated in position 834 as illustrated in FIG. 13B. The source assembly 86 may move any appropriate amount and the illustrated position is merely for the current discussion. Nevertheless, at the second or alternative position 834, the source point 414 may be operated to emit a beam of x-rays and a beam 842 through the volume 524 to be detected at the detector 88. The beam 842 may pass through a different portion of the volume 524 and/or may overlap a portion through which the beam 834 passes. Nevertheless, the second position 838 may allow x-rays in the beam 842 to be detected by the detector 88 from a different one of the sources, such as the source 414, of the source assembly 86.

Figure 13C:
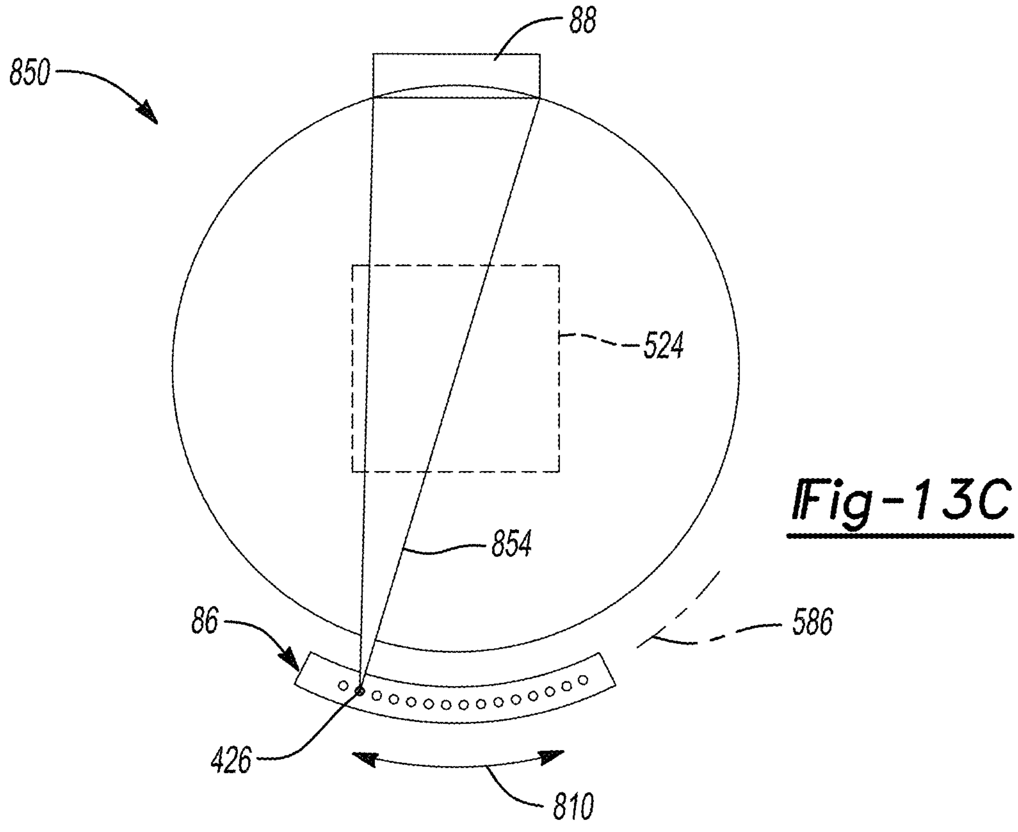

Turning reference to FIG. 13C, the source assembly 86 and the detector 88 may be positioned in a third position 850. The third position 850 may have the source point 426 emit a cone of x-rays 854 through the volume 524 to be detected at the detector 88. Again, the source assembly 86 may move in the direction of the double headed arrow 810 along the path 586 to the position 850, as illustrated in FIG. 13C, for acquisition of image data. In the position 854, the source point 426 may be powered or operated to emit x-rays for passing through the volume 524 to be detected at the detector 88. As illustrated in FIG. 13C, the beam 854 may pass through a different portion of the volume 524 and/or overlap at least a portion of any of the prior beams, such as the beams 834 and 842.

Figure 13D:
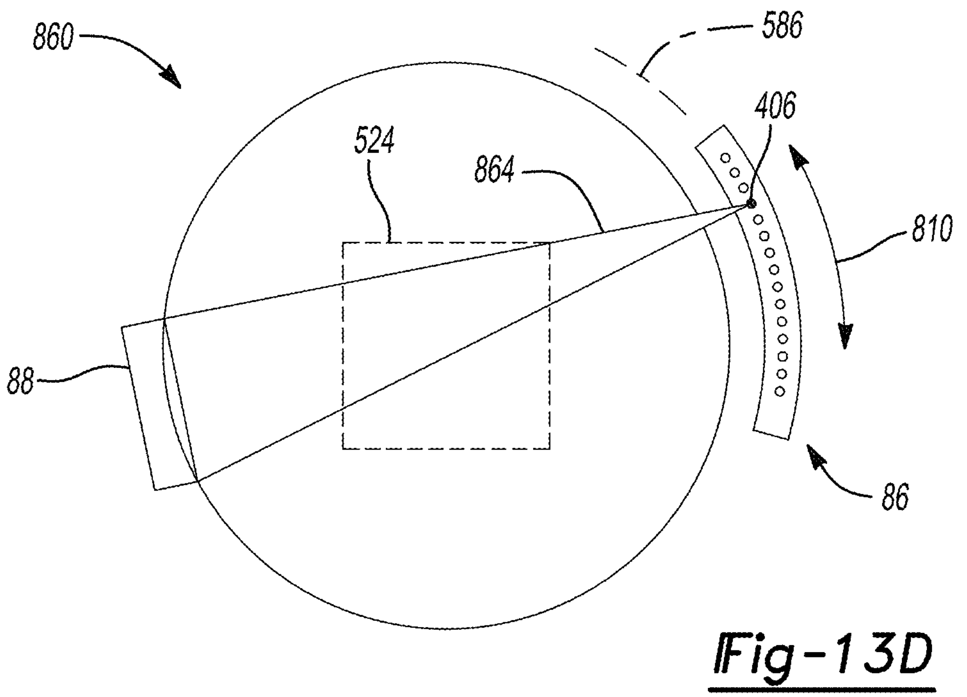

Turning reference to FIG. 13D, the source assembly 86 and the detector assembly 88 may move to a fourth position 860, as illustrated in FIG. 13D. In the position 860, the source assembly 86 may be positioned by moving the source assembly in the direction of the double headed arrow 810 along the path 586. At the position 860, the source point 406 may be operated or powered to emit a cone of x-rays 864 through the volume 524 to be detected by the detector 88. The beam 864 may pass through a portion of the volume 824 through which a portion of one of the prior beams is passed, and/or in a different portion.

Accordingly, as illustrated above, for example in FIGS. 13A-13D, the source assembly may move within or relative to the gantry 82 for acquisition of image data at a plurality of perspectives relative to the volume 524. As discussed above, the volume 524 may generally include a portion of and/or surround the subject 30 for acquiring image data of the subject 30. During movement of the source assembly 86, different ones of the source points may be operated or powered individually to pass the x-ray beam through the volume 524 to be detected by the detector 88. As exemplary illustrated in the various positions 830, 838, 850, and 860, each of the source points may be operated in a selected pattern which may be sequentially, every other one, a selected number of powered in a sequential and repeating pattern, or any other appropriate pattern, such as those discussed further herein.

Accordingly, as the source assembly 86 moves relative to the volume 524, different ones of the source points, such as the 15 source points 400-428, may be powered to emit x-rays through the volume 524. Each of the source points may include a selected characteristics, such as different powers or selected filters, as discussed above. Further, the source assembly 86 may be moved relative to the subject to acquire image data at different perspectives relative to the volume 524 and/or different ones of the source points may be powered at any particular location of the source assembly 86 to acquire image data at different perspectives at a single one position of the source assembly 86. For example, the position 838 may power both the source 414 and the source points 400 and 428. Similarly at any one particular position of the source assembly any selected number of the sources may be powered in a selected pattern, such as simultaneously, sequentially, or the like to acquire image data of the subject 30 such as within or through the volume 524.

Figure 14:
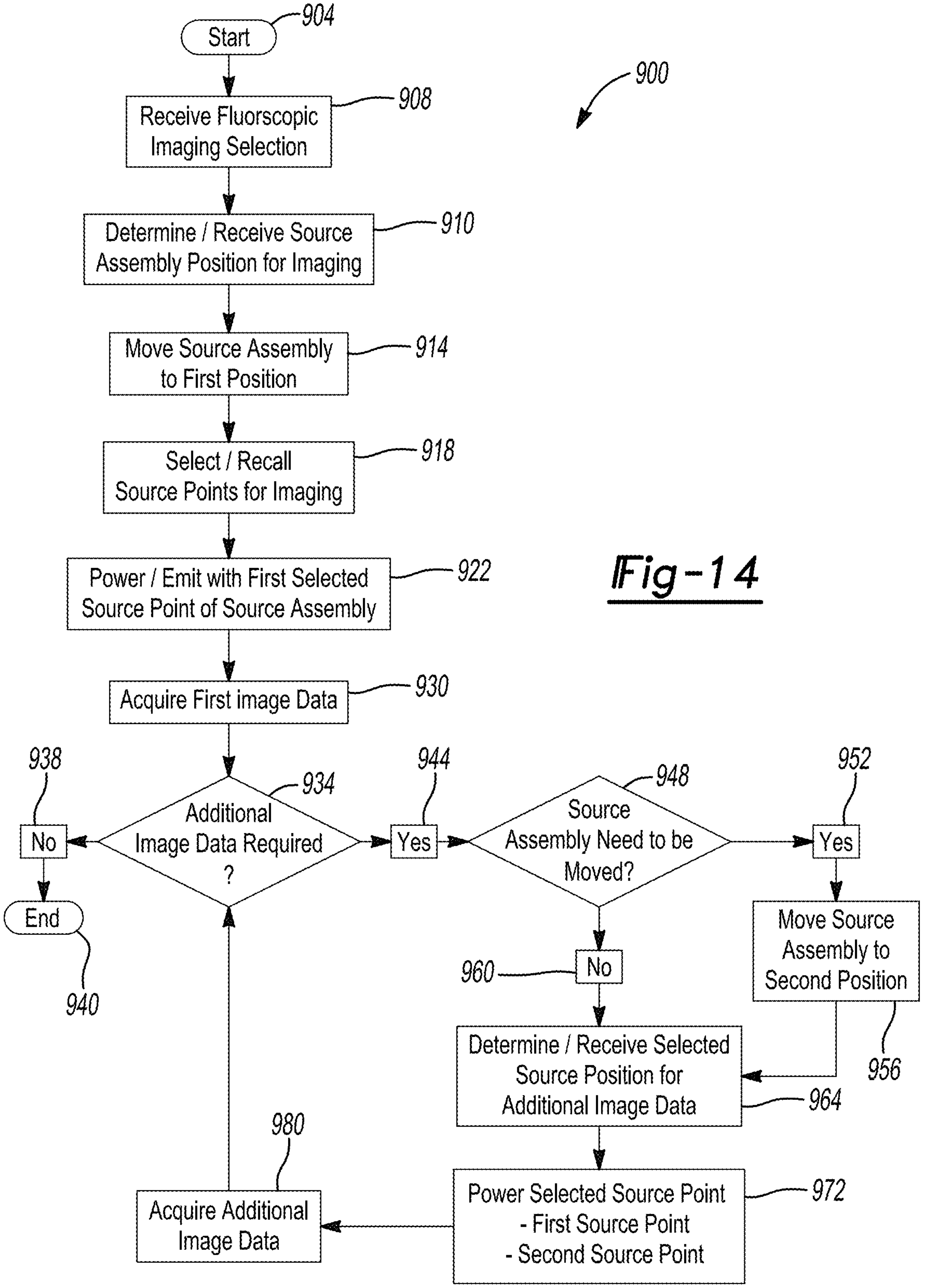
FIG. 14 is a flow chart for operation of an imaging system, according to various embodiments.
Figure 15:
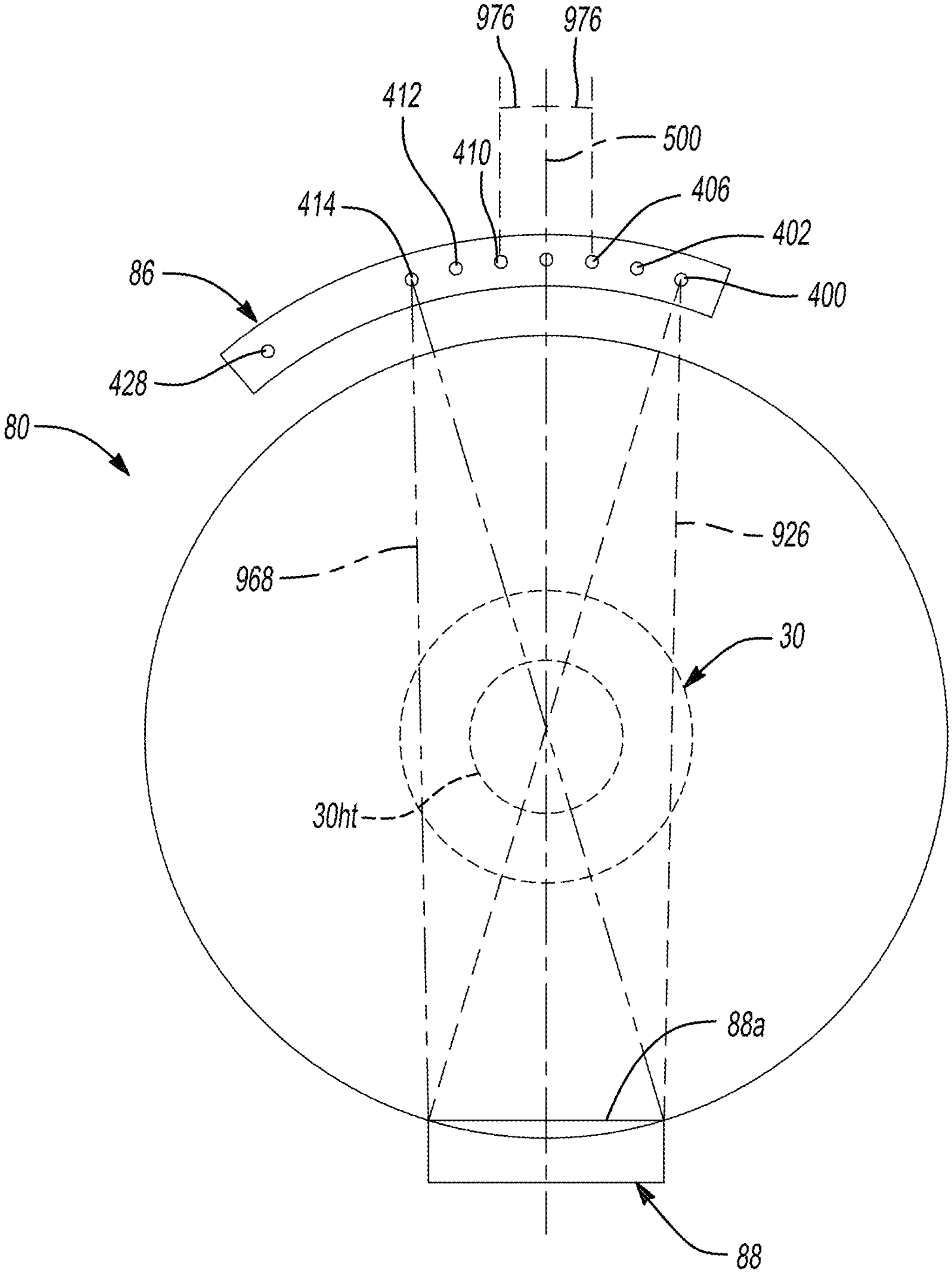
FIG. 15 is a schematic illustration of an imaging system operated according to the flow chart of FIG. 14.

With continuing reference to FIG. 12, and additional reference to FIG. 14 and FIG. 15, the imaging system 80 may be operated as a selected type of imaging system, such as a fluoroscopic imaging system. During fluoroscopic imaging, a continuous beam of x-rays may be emitted by one or more source points in the source assembly 86 for acquisition of image data of the subject 30 over a selected period of time. Accordingly, with reference to FIG. 14, a process 900 is illustrated for fluoroscopic imaging with the imaging system 80, according to various embodiments as discussed above.

Generally, the method 900 may begin in at start block 904. A signal or instruction to start fluoroscopic imaging may then be received in block 908. The received signal may be made from the user 72, such as with the imaging control system 96, or through any other appropriate input or receiving system. After receiving the fluoroscopic imaging selection in block 908, a determination of a position or location of the source assembly may be made in block 910. The determination of a position of the source assembly of block 910 may be made based upon the appropriate or selected type of fluoroscopy. In various embodiments, the imaging system 80 may be used to assist in performing a catheterization, a digestive or intestinal tract study, or other appropriate studies. Accordingly, a determination of one or more positions of the source assembly 86 may be made in block 910. Further, various studies may include selected or predetermined positions of the source assembly 86, therefore, a determination or receiving of the source assembly position block 910 may be recalling from a memory of a selected source assembly position.

Once the determination of a position of the source assembly is made in block 910, if movement is required the source assembly may be moved block 914. Turning to reference FIG. 15, a schematic illustration of the imaging system 80 is illustrated including the source assembly 86 and the detector 88. As discussed above, the detector 88 may include the detector surface 88*a* and a plane or axis 500 may extend from the detector surface 88*a*. In the determining a position and/or moving the source assembly 86 to a selected position, the position may be relative to the subject 30, as illustrated in FIG. 15, such that the axis 500 extends through the subject 30 such as in a selected position, including relative to a heart 30*ht* or other selected portion of the subject 30.

A selection or recalling of which source points of the source assembly 86 may be made in block 918. For imagining with the fluoroscopic technique, it may be selected to include or power a plurality of the x-rays points or portions, such as one or more of the 15 portions 400-428 of the source assembly 86. It is understood b tone skilled in the art, while the following discussion is directed to the source assembly with 15 source portions, any appropriate number of source portions may be included as discussed above.

The selection or recall of which source portions may include a selection of substantially symmetrical source portions relative to the axis 500. Accordingly, two or more of the source portions may be selected that are substantially symmetrical to the axis 500 for acquiring projections (e.g. image data) of the subject 30, such as the heart 30*ht*. For example, the source point 400 may be selected and the source point 414 may be selected for acquisition of the fluoroscopic image data. In various embodiments, the fluoroscopic image data may be acquired with both of the source portions 400, 414, such as in an alternating pattern. It is understood that additional source portions may also be used to acquire the fluoroscopic image data, such as the source portions 402 and 410. It is further understood, as discussed above, that selected source portions that may be a subset or selected subset of the source portions of the 15 source portions 400-428 and may include selected filters for use during a fluoroscopic imaging procedure. Accordingly, the selection or recall of source points for imaging in block 918 may include a selection of the subset of source portions that may be symmetrically positioned relative to the axis 500 and/or those that include the selected filtering or shaping features. Additionally, source portions for fluoroscopy may be operated at selected factors or parameters, such as a selected energy and/or a rate including a selected average power and/or voltage.

Once the selection is made in block 918, a powering or emission of a beam (e.g. a x-ray beam) from a first selected source point or portion of the source assembly is made in block 922. The emission may be, for example, from the source point 400 as illustrated in FIG. 15. The first portion may be the source portion 400 that emits a first beam 926. The beam 926 may pass through the subject 30 including a portion of the heart 30*ht* and be detected at the detector 88. Accordingly, acquisition of a first image data is made in block 930. The first image may be viewed with the display device 84, as discussed above. Further, the image data may be saved for various analysis and/or additional procedures, as is understood by one skilled in the art.

After the acquisition of the first image data of the block 920 a determination of whether additional image data is required or is to be acquired in block 934. The determination of whether additional image data is needed may be made during an initial planning, such as with the receiving or included with the receiving of the fluoroscopic imaging in block 908. Further additional instructions may also be received from the user 72 or based upon the user 72 for the acquisition of additional image data.

If no additional image data, is required a NO path 938 may be followed to an end block 940. The end block 940 may include various procedures, such as any acquisition of image data with the imaging system 80. Also, the procedure on the subject 30 may continue such as analyzing the image data, preforming a procedure on the subject 30 with the image data, viewing the image data, altering the image data, or other appropriate procedures. Accordingly, the end block 940 may simply be ending the fluoroscopic image acquisition with the imaging system 80.

If additional image data is required, a YES path 944 may be followed. The YES path 944 may proceed to a determination of whether the source assembly needs to be moved to block 948. If a determination that the source assembly does need to be moved is made, a YES path 952 may be followed to move the source assembly in block 956. In various embodiments, however, as illustrated in FIG. 15, the source assembly 86 need not be moved to acquire additional fluoroscopic image data. It is understood, however, that the source assembly 86 (either alone or in combination with the detector 88) may move relative to the subject 30 for the acquisition of fluoroscopic image data. The determination of whether the source assembly needs to move in block 948 may, therefore, also follow a NO path 946.

After determining that the source assembly is moved in block 956 or that it does not need to be moved in block 960, a determination of a selected source portion for additional image data is made in block 964. he additional source portion may be the initial or first source portion, such as the source portion 400. In various embodiments, for example, the source portion 400 may be used to acquire additional image data, such as with a further beam and/or after moving the source assembly 86 to a different position. It is further understood, however, that an additional or different source portion may be used to acquire additional image data, such as the source portion 414.

The source portion 414, therefore, may emit x-rays in a second beam 968 that may pass through and/or be attenuated by the heart 30*ht* of the subject 30 and detected at the detector 88. As discussed above, the second source portion 414 is symmetrical relative to the axis 500 from the first source portion 400. Accordingly, the image data acquired with the second source portion 414 may relate to the image data acquired with the first source portion 400, such as being offset relative to the axis 500. In various embodiments it is understood, however, that the source portions that acquire fluoroscopic image data maybe those that are as close to the axis 500 as possible while being symmetrical relative thereto. Accordingly, the source portion 406 and 410 may be the two source portions, including the first source portion powered in block 922 and a second source portion powered in block 972 after selection is made in block 964.

In various embodiments, for example, the fluoroscopy of the subject 30 may be selected to include image data that is substantially continuous or continuously viewable of the subject 30, such as during a cardiac catheterization. The position of the source portions relative to the axis 500 may be known or determined, such as being a selected angular or distance offset from the axis 500, which may be identical for both of the source portions used during the selected fluoroscopy imaging procedure. The imaging system 80, and/or the associated control system 96, may know or determine the position of the source portions relative to the axis 500 and generates images for viewing with the display device 84 that account for the known and selected offset such that the displayed image appears to be taken from a substantially single position relative to the subjection or portion of the subject, such as the heart 30*ht*. For example, both of the sources 406, 410 may be offset a similar or identical distance 976 relative to the axis 500. The offset 976 may be an angular offset or a translational distance offset and may be used to determine images for display on the display device 84. Accordingly, the process 900 made used to acquire image data that may be displayed with the display device 84 for a selected procedure.

After powering the second source in block 972, the acquisition of additional image data is made in block 980. The additional image data, as discussed above, may be displayed on the display device 84 for a selected procedures, such as a fluoroscopy procedure. After the acquisition of the additional image data block 980, again a determination may be made of whether additional image data is required in block 934. The process 900, therefore, may then proceed as discussed above based upon whether additional image data is required for a selected procedure. Accordingly, a fluoroscopy procedure may be performed with the imaging system 80 using a plurality of the source portions of a source assembly 86.

In various embodiments, the multiple source portions may be used to ensure an appropriate cooling of one or more of the source portions between different data acquisitions to acquire image data of the subject 30. For example, the single or first source portion 400 may require a cool down period after a selected emission timing (e.g. after 1 or 2 milliseconds). Therefore, switching to an alternative or second source portion may be used to allow for a continuous fluoroscopic imaging procedure while allowing the first or other source portions to have a cool down or relaxation period prior to the repowering of the same source portion of the source assembly 86.

As discussed above, the imaging system may be operated in the fluoroscopic manner, according to the method as illustrated in FIG. 14. During the acquisition of the image data, either in the first image data block 930 and/or in the additional image data block 964, various additional features may be used. For example, the imaging system 80 including the source assembly 86 may include a specific ones of the source portion, such as source portion 406 and 410 that may be operated as fluoroscopic imaging or source portions. These source portions may be dedicated to fluoroscopic imaging and may not be used during other types of imaging with the imaging systems 80, according to various embodiments. It is understood, therefore, that certain source portions may be dedicated to specific types of imaging, such as fluoroscopic imaging.

Further, these sources may be positioned relative to one another, as discussed above, such that they are spaced away from one another. Thus during a fluoroscopic imaging technique the two sources may be used to image sequentially and/or substantially simultaneously to identify or determine a perspective that may be similar to a substantially three-dimensional (3D) perspective. As the two sources may be offset from one another, such as over an angular distance, the image acquired may be at two different perspectives relative to the axis 500. Further, images acquired with the two sources may be at a perspective distance relative to one another. Thus, the fluoroscopic imaging system may be used to acquire perspective, such as 3D perspective, image data of the subject 30 during a fluoroscopic imaging process. In various embodiments, for example, the two sources, such as the source 406 and the source 410, may be sequentially operated to acquire two different perspectives of the subject 30. The two different perspectives may be acquired with the source assembly 86 and the subject 30 and the detector 88 all at the same position. The perspective images may be generated by using two of the source portions without moving any portion of the imaging system, such as the source assembly 86 and/or the detector assembly 88.

Further, different imaging source portions may be used to acquire image data according to different characteristics. For example, two different energies may be used. For example, the first source portion 406 may be used to acquire x-ray projections with a first x-ray energy such as about 80 kilovoltage peak (kvp), including about 70-90 kvp. The second source portion 410 may be used to acquire the x-ray projections with a second energy such as about 140 kvp, including about 130-150 kvp. Accordingly, the fluoroscopic images may be acquired at different energies that may be generated with two different source portions.

Further, the fluoroscopy images may be acquired along a long axis, such as the axis 234 of the subject. The source assembly 86 may be positioned within the gantry 82 such as generally along the axis 582, as illustrated in FIG. 8C. Accordingly, the image data may be acquired along a long axis of the subject which may also be the axis 558 of the imaging system 80. Further, as discussed above, the source assembly 86 may rotate as illustrated in FIGS. 9A and 9C. The source assembly, therefore, may be positioned within the gantry 82 to acquire the image data along the long axis of the subject 30. Accordingly, the fluoroscopic image data of the subject may be acquired at a selected perspective, such as relative to the long axis 234 of the subject 30 which may be generally in a Z direction or axis to the imaging system 80.

Further the fluoroscopic imaging, as discussed above, may be used to acquire a substantially real time image or data acquisition of the subject 30. Such real time acquisition may be used for various purposes, such as for performing selected catheterization or real time tracking in images of the subject or relative to the subject 30. Further, the images may be acquired to assist in directing selected surgical systems, such as for guiding a catheter, guiding a deep brain stimulation device, or other appropriate systems or implants. Thus, selected surgical systems, such as robotic systems, may receive the fluoroscopic image data as an input to assist in directing or performing a procedure. For example, selected robotic systems may include the Mazor X robotic system, such as that sold by Medtronic, Inc., may be operated in an autonomous or semi-autonomous manner to perform a procedure on the subject 30 with the image data acquired with the imaging system 80.

In addition to the operation, as discussed above, the imaging system 80 may be operated as the fluoroscopic imaging system where different ones of the sources 400-428 operate at different exposure rates. In various embodiments, during operation of the imaging system 80 as a fluoroscope, the source assembly 86 may move relative to the subject 30. As the source assembly 86 moves the different ones of the sources may be operated to generate the image data or the x-rays detected at the detector. Accordingly, different ones of the sources may be operated at different exposure rates to acquire appropriate image data. For example, as the source assembly 86 moves relative to the subject the source portion 400 may be operated at a selected rate, such as at a rate as half, a quarter, or other appropriate fraction relative to other source portions in exposure speed, energy, etc. For example, the source 400 may be positioned relative to the subject in an appropriate position to acquire image data at only selected portions of movement relative to the subject of the source assembly 86. Accordingly, the source portion 400 may only be operated at selected times, rather than constantly or continuously during movement of the source assembly 86 relative to the subject 30. Accordingly, different ones of the source portions may be operated at different rates or exposure times or amounts to acquire image data of the subject 30 in an appropriate manner, such as for fluoroscopic imaging.

Figure 16:
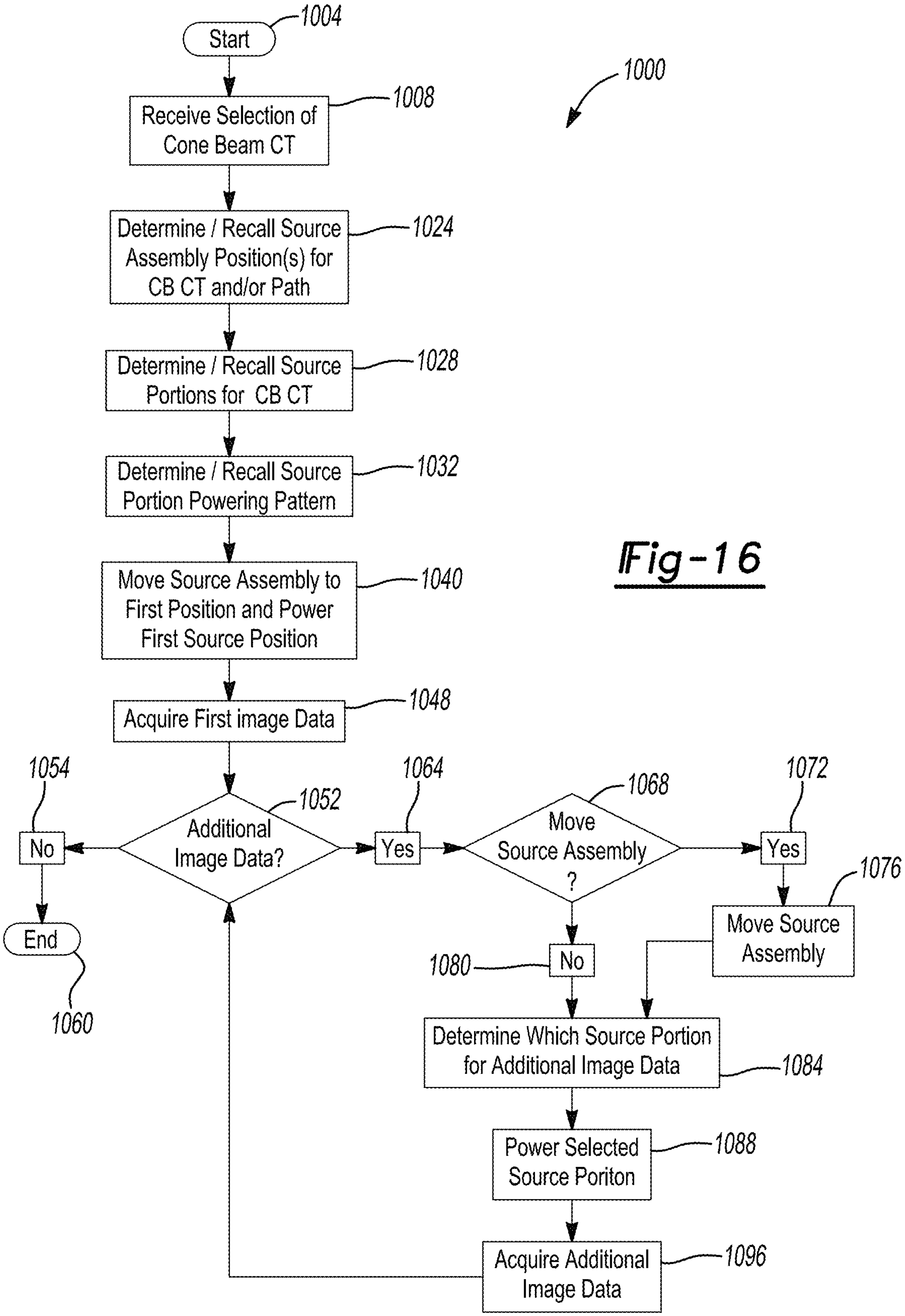
FIG. 16 is a flow chart illustrating operation of an imaging system, according to various embodiments.
Figure 17A:
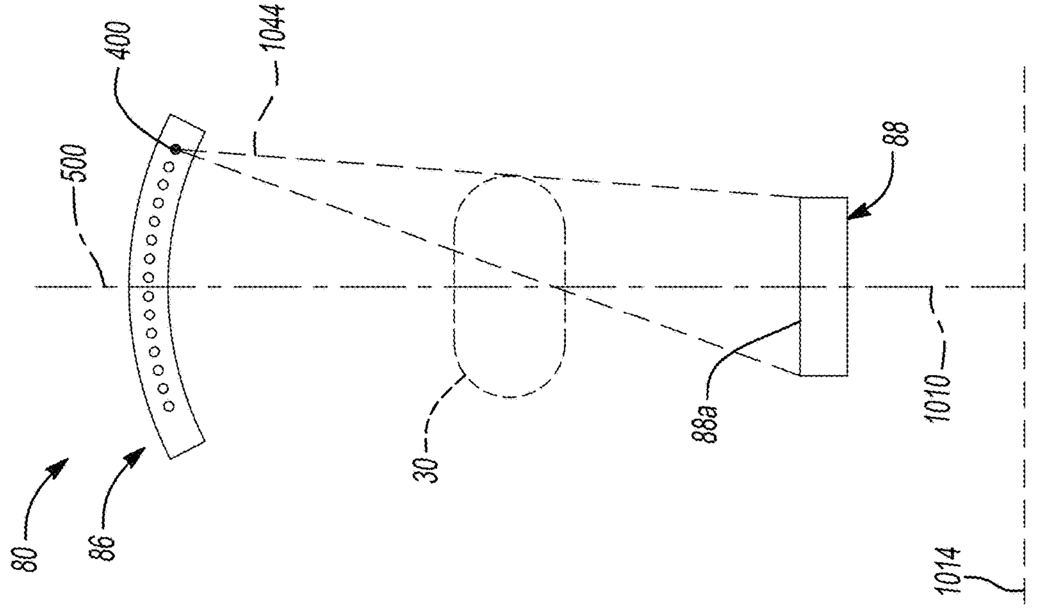
FIGS. 17A and 17B are schematic illustrations of an imaging system operated according to the flow chart of FIG. 16.
Figure 17B:
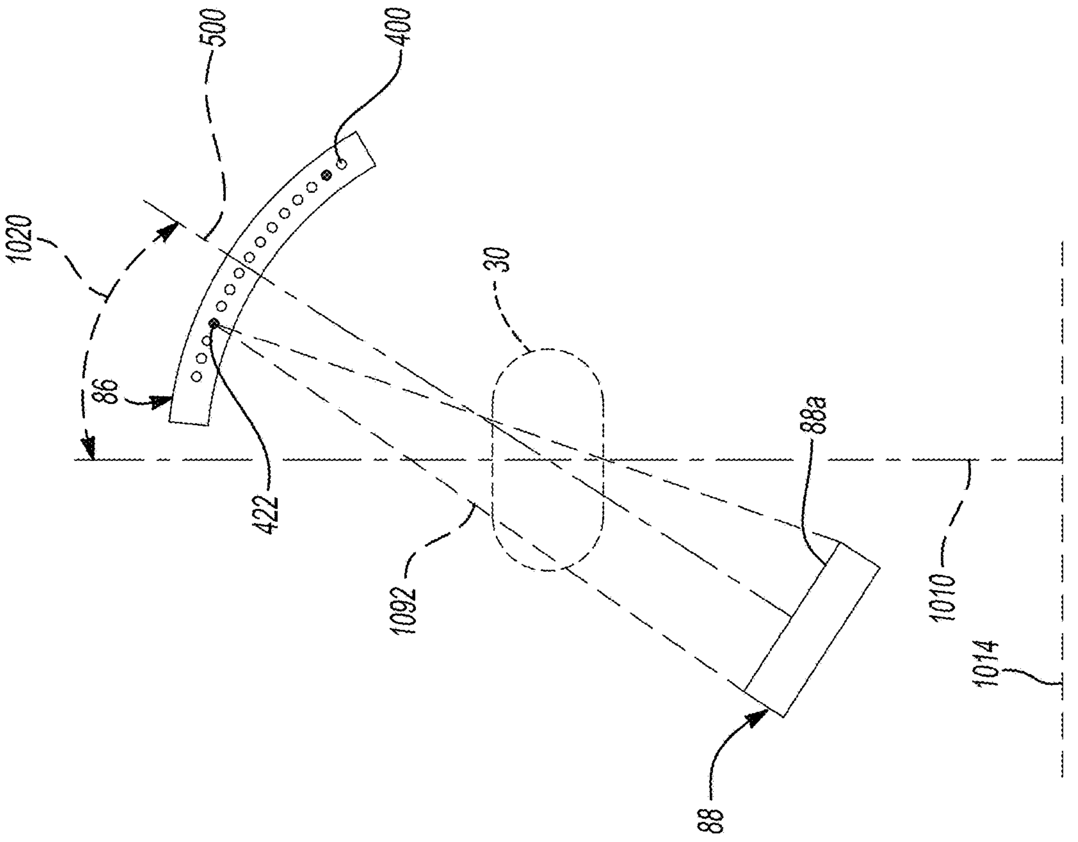

Turing reference to FIG. 16 and FIGS. 17A and 17B, the imaging system 80 may also be operated in a selected manner, such as in a cone beam computed tomography (CBCT) system. The imaging system 80 may be operated as the cone beam imaging system in a manner that may be similar to operating in the fluoroscopic system, or include differences as discussed herein. Accordingly, it is understood that the imaging system 80 may be operated in a selected manner to acquire image data of the subject 30.

With initial reference to FIG. 16, a method or process 1000 is illustrated. The process 1000 may begin in start block 1004. The start block 1004 may include appropriate starting procedures, such as similar to the start block 904, as discussed above. For example, the imaging system 80 may be moved relative to the subject 30 from a selected location, such as from a different room and/or being repositioned within the single room. As discussed above, the imaging system 80 may include various features, such as the gantry 82 that includes the fixed portion and the movable portion. Thus, during a selected procedure, for example a selected DBS placement, prosthetic placement, or the like, the imaging system 80 may be moved from a first position near the subject to image the subject, then moved away from the subject, and may be returned to image the subject again. Accordingly, the start in block 1004 may include various techniques or features such as moving the imaging system relative to the subject 30, powering the imaging system, or the like.

After beginning in start block 104, receiving an imaging request or technique for cone beam CT is made in block 108. To operate the imaging system 80 as a cone beam CT, the source assembly 86 may move relative to the subject 30 to image a volume in which the subject 30 may be placed. The imaging system 80, therefore, may be operated as a cone beam imaging system to acquire image data of the subject 30. In various embodiments, the image data collected during CBCT may be reconstructed to generate a three dimensional model reconstruction of the subject based upon the acquired image data. The image data may be acquired of the subject 30 in a selected manner, such as moving the source assembly 86 and/or operating one or more of the source assemblies, such as one or more of the 15 source assemblies 400-428, as discussed further herein.

The image system 80, including the source assembly 86, as illustrated in FIG. 17A (schematically) may be operated to acquire or operate in the cone beam CT manner. The imaging system 80 may be operated as a cone beam CT by imaging the subject 30 with the source assembly 86 along with the detector 88. As discussed above, the detector 88 may include the surface 88*a* that may extend through the source assembly 86 and the source assembly 86 may be provided symmetrically or anti-symmetrically relative thereto. Further, and axis 1010 may extend through the subject 30 and relative to a surface, such as floor or support surface 1014. The axis 1010 may be understood to be any selected axis through the subject 30, as provided for reference herein.

With brief reference to FIG. 17B, and continuing reference to FIG. 16, the source assembly 86 may move relative to the subject 30 along with the detector 88. The axis 500 extending from the surface 88*a* of the detector 88 may be at an angle or position relative to the reference axis 1010 relative to a surface 1014 and/or the subject 30 at a selected time, such as after a period of movement of the source assembly 86. In one example, the axis 500 may be at a position 1020 relative to the patient axis 1010. When at the position 1020 a different one of the source portions, such as the source portion 422, may be powered to emit x-rays through the subject 30 and to be detected at the detector 88.

As the source assembly 86 may move, the method 1000 may include determining or recalling a source assembly position or positions for imaging in block 1024. As discussed above, the source assembly 86 may be moved relative to the subject 30 during the imaging of the subject 30. Accordingly, the recalled determined positions may include a path for acquiring image data of the subject 30. It is understood that the source assembly 86, therefore, may be moved during the imaging of the subject 30. The source assembly 86 and, therefore, other portions of the imaging system 80, may then move or be moved relative to the subject 30 for the acquisition of the image data.

Further, the method 1000 may include determining or recalling which source portions or points will be powered for the CBCT imaging in block 1028. Further a determination or recall of a pattern for powering the recalled source portions is made in block 1032. As discussed above, each of the source portions may be powered in a selected manner, such as for a selected time period, a selected power parameter, a selected filter or shape, or the like. Further, as discussed above, the source assembly 86 may include the plurality of source portions, such as the 15 source portions 400-428, a certain selected number or subset of the source portions may be operated for CBCT imaging entirely. Accordingly, selected filters may be associated with the source portion and then may be operated to acquire the CBCT image data. The determination and recall of which source portions and which parameters to operate them may be based upon the selected subset of the source portions and/or the path to acquire the image data of the subject. Further, the path and which portions and the parameters therefore may be based upon the type of subject to be imaged and/or portion thereof (e.g. soft tissue relative to hard tissue, a joint replacement, a soft tissue implant (e.g. catheterization)).

Once a determination of a path, which source portion to power, and the patter for powering the source portions is made, the source assembly may be moved to the first position and the first source portion may be powered in block 1040. As briefly discussed above, as illustrated in FIG. 17A, the source assembly 86 may be positioned such that the axis 500 is aligned with the axis 1010 of the subject 30. The source portion 400 may emit a beam, such as a cone beam 1044, and it may be detected at the detector 88. The detector 88 may, therefore, acquire image data when the source assembly 86 is at the first position, as illustrated in FIG. 17A. This allows an acquisition of first image data may be made in block 1048. The first image data may be used for various purposes, such as a reconstruction, as discussed further herein, assisting and determining a further path for imaging, or the like.

A determination of whether additional image data is requested and/or needed is made in block 1052. If no additional image data is needed, a NO path 1054 may be followed to an end block 1060. The end block 1060 may be a finishing of the procedure 1000. It is understood, that additional features or purposes may occur. For example, as discussed above, the image data may be reconstructed to generate a selected model (e.g. a three-dimensional image) of the subject 30 based upon the acquired image data. Further, the user 72 may use the generated image and/or generated image data to assist in selected procedures, such as performing a procedure on the subject 30. Also as discussed above, the image may be displayed for selected navigation, such as surgical navigation procedures, on the subject. Accordingly, ending the process 1000 at block 1060 may not necessarily mean the ending of a selected procedure, and/or use of an image generated with the imaging system 80, but may generally be simply the end of the CBCT imaging process.

If, however, a determination that additional image data is requested or required in determination block 1052, a YES path 1064 may be followed. When following the YES path 1064, additional image data may be acquired. After the determination is made in block 1052 that additional data is acquired in the YES path 1064 as followed. The source assembly may be moved as determined in block 1068. If a determination that the source assembly needs to be moved, such as based upon the path as determined in block 1028, a YES path 1072 may be followed. The source assembly may then be moved in block 1076 as discussed above movement of the source assembly block 1076 may be based upon the determined or recalled path in block 1024. Further, as discussed above, the source assembly 86 may also rotate or move relative to the detector 88. Thus, movement of the source assembly may include any selected movement of the source assembly. Further, a determination that the source assembly may not be moved and a NO path 1080 may be followed.

Regardless, when the source assembly is at a selected position for the acquisition of additional image data, a determination of which source portion or points per additional image data is made in block 1084. The determination of which source portion for additional image data may be based upon the determined recall which source portions for CBCT in block 1028 and/or the source portion powering pattern in block 1032. As discussed above, the determined or recalled path, the determined or recalled source portions for CBCT, and/or the determined or recalled powering pattern, may be used to determine the acquisition of additional image data after the acquisition of the first image data in block 1048. Accordingly, the determination of which source portion in block 1084 may include following the previously determined or recalled path, source portions, or source powering pattern in blocks 1024, 1028, 1032, respectively.

After the determination of which source portion is to be powered and what pattern for additional image data in block 1084, the selected source portion may be powered in block 1088. The selected source portion powered in block 1088 that is determined in block 1084 may include or be the first source portion used to acquire the first image data in block 1048. The first source portion may be powered in a selected manner, such as with a selected voltage, amperage, shape, or the like to acquire selected image data. Accordingly, the additional image data may be acquired with the same source portion used to acquire the first image data, but in a different manner and/or a different position of the source assembly 86. Further, the selected source portion determined in block 1084 may be a different one of the source portions from the source assembly 86, such as the source portion 422, as illustrated in FIG. 17B. It is understood, however, that additional image data may be collected in substantially the same manner as initial or previous image data, such as for confirmation or additional data collection.

The source portion 422 powered in block 1088 may emit a beam of x-ray 1092 that is detected at the detector 88. The detector 88 may be positioned at a position 1020 from the axis 1010. The source portion 422, therefore, may pass through a selected portion of the subject 30 when acquiring the additional image data in block 1096. The additional image data may be used to assist in forming a selected image of the subject 30, such as a three dimensional reconstruction, of selected portions of the subject 30.

Further, the additional image data may be acquired at a different perspective, as illustrated in FIG. 17B, and/or different translated position and/or different time then the acquisition of the first image data in block 1048. Accordingly, a passage of time may happen between the acquisition of the first image data block 1048 and the additional image data block 1096. In various embodiments, the different image data acquisitions may be registered for reconstruction of the image and/or may be used to illustrate sequential changes of the subject 30. Nevertheless, the source assembly 86 may move relative to the subject 30 to acquire image data at various and different perspective and/or positions for acquisition of image data of the subject 30 to perform a reconstruction thereof.

The acquisition of additional image data may occur in block 1096. After acquisition of additional image data block 1096, a determination of whether further additional image data is needed in block 1052. As discussed above, the determination of whether additional image data is needed may be based upon the type of imaging such as the CBCT plan or path that may be determined or recalled. Accordingly the process 1000 may be used to continuously or loop determine the position of the source assembly 86, the selection of the source portion to emit the beam of x-rays acquisition of image data, and/or the amount of image data and positions required for the selected image data acquisition. Accordingly, as discussed above, the determination of whether additional image data is required to follow the YES path 1064 or the NO path 1054.

The process 1000, therefore, may be for the acquisition of the CBCT image data. Accordingly, in the end block 1060 and/or following the end block 1060 the acquired image data that may include a plurality of image data acquisitions or projections of the subject 30. The plurality of image data acquisitions may be used, as discussed above, to perform a reconstruction of an image, such as a three dimensional image or model, of the subject 30. Reconstruction of the three dimensional image may be based upon generally known reconstruction techniques such as Filtered Back Projection or Iterative Reconstruction methods. Thus, the image data acquired with the imaging system 80 with one or more of the source portions of the source assembly 86 may be used to reconstruct a selected image of the subject 30. The image may then be displayed on a selected display device, such as the display device 84, as discussed above. The reconstructed image may therefore be used in various procedures such as a navigated procedure relative to the subject 30 and/or planning or diagnostic procedures of the subject 30.

Figure 18:
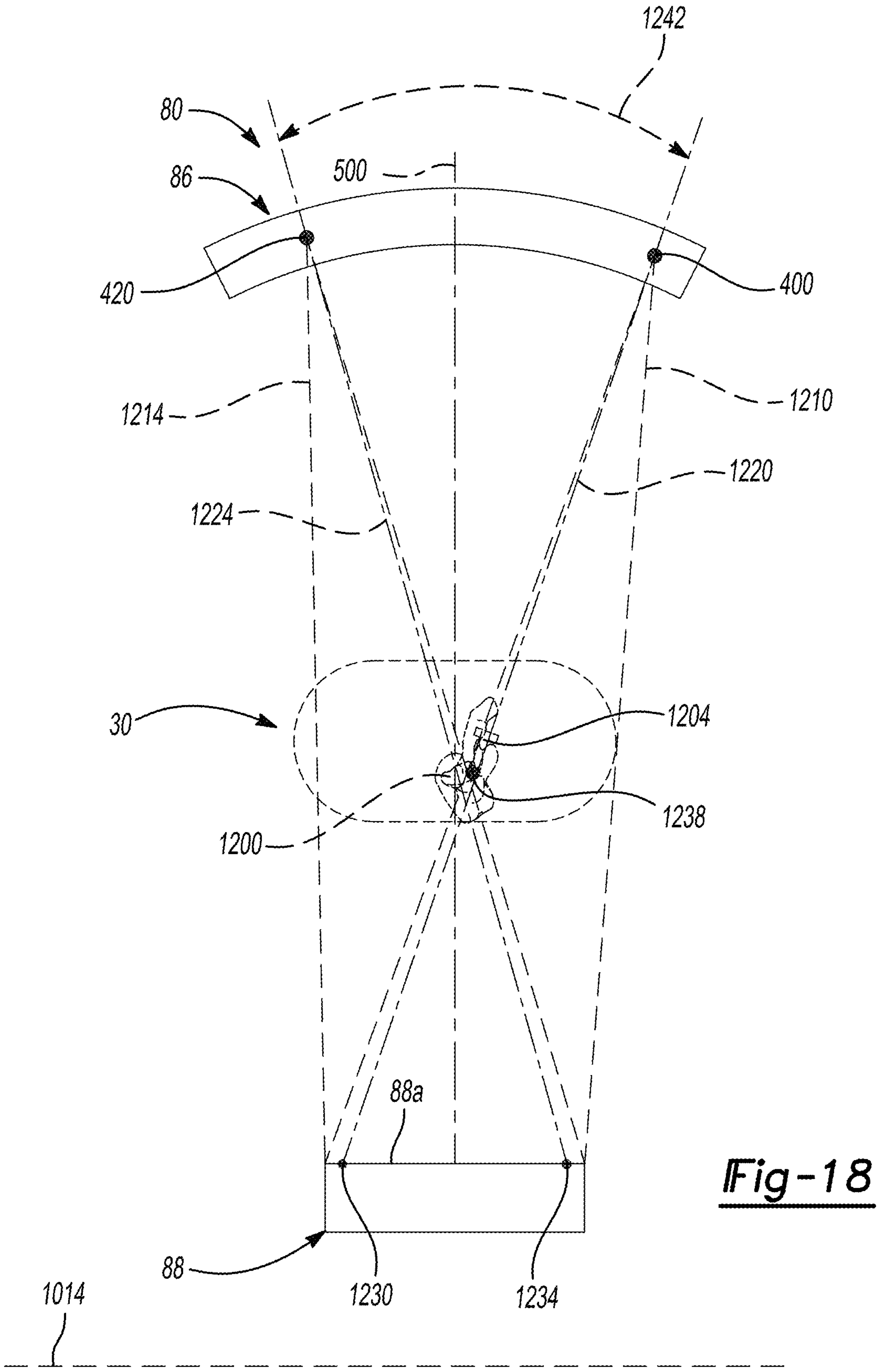
FIG. 18 is a schematic illustration of an imaging system having a plurality of source portions operated simultaneously, according to various embodiments.

In various embodiments, the imaging system 80, including the source assembly 86 and the detector assembly 88, as schematically illustrated in FIG. 18, may also or alternatively be used to acquire image data of the subject 30 with two or more of the source portions, such as the source portion 400 and the source portion 420, substantially simultaneously. As discussed further herein, a plurality of source portions may be used to acquire image data substantially simultaneously for acquiring image data of selected portions of the subject 30 simultaneously. The different source portions may acquire image data at different perspectives relative to the subject 30 with a single image acquisition or a detector acquisition for various purposes, such as registration, as discussed further herein.

With continuing reference to FIG. 18, and reference to above described figures including FIG. 1, FIG. 6A, and FIG. 12, the imaging system 80 may be positioned relative to the subject 30. The subject 30, as discussed above, may include any appropriate subject such as a human subject. In various embodiments, for example, a portion of the subject 30, such as a vertebrae 1200 may be within the subject 30. Relative to the vertebrae 1200 may be positioned an implant, such as a pedicle screw 1204 or other appropriate implantation prosthetic members or implantable members. It is understood that the pedicle screw 1204 is merely exemplary, and other appropriate portions may be positioned within the subject. Further, as is understood as one skilled in the art, various portions such as the vertebrae itself 1200 may be imaged for various purposes, such as those discussed further therein.

Nevertheless, the subject 30, such as including the vertebral screw 1204 and/or vertebrae 1200 may be imaged with the imaging system 80. The source assembly 86 including the plurality of the source portions, such as the source portions 400 and 420, may be used to acquire a substantially simultaneous image data acquisition of the subject 30. For example, the source portion 400 may emit a beam of x-rays 1210. The source portion 420 may emit a beam of x-rays 1214. Both of the beam of x-rays 1210, 1214 may pass through the subject 30 and/or a portion of the subject 30, such as the vertebrae 1200 and/or the pedicle screw 1204. The beams may have selected portions, such as a ray 1220, 1224 respectively, that may pass through a selected intersecting portion of the subject, such as for example, the vertebrae 1200 and/or the pedicle screw 1204. The x-rays along the respective rays 1220, 1224 may then be detected at the detector 88, such as at the surface 88*a* at different positions. For example the ray 1220 may impact or extend to the detector at the point 1230. The ray 1224 may extend to the detector surface 88*a* at point 1234. Accordingly, the two rays 1220, 1224 may pass through or intersect the subject or volume or area within the subject, such as an intersection point 1238. The single point 1238 can be projected on the detector surface 88*a* at two different and generally spaced apart points. The difference in contact or projection points 1230, 1234 is due to the offset position (i.e. distance between) of the respective source portions 400, 420 relative to the imaged portion or point 1238.

The source portion 400 may be offset relative to the source portion 420 a selected distance or amount 1242. The offset may include an angular offset including about 5 degrees to about 20 degrees, and further including about 10 degrees. Further, the source portions 400, 420 may be offset a selected amount relative to the axis 500 extending from the detector surface 88*a*.

The imaging system 80 may include a selected controller, such as the controller 96 that may have determined offset or position of the respective source portions, such as the offset 1242 being known or predetermined. The offset 1242 may be predetermined and stored for later recall, such as by the controller including a processor portion or model. Further the position of the source assembly 86 (e.g. relative to the subject) may be known due to controlling of the imaging system 80, such as movement of the source assembly within the gantry 82 and/or tracking of the gantry 82 (e.g. with the imaging tracking device 62), or other appropriate position or pose determinations.

Figure 19:
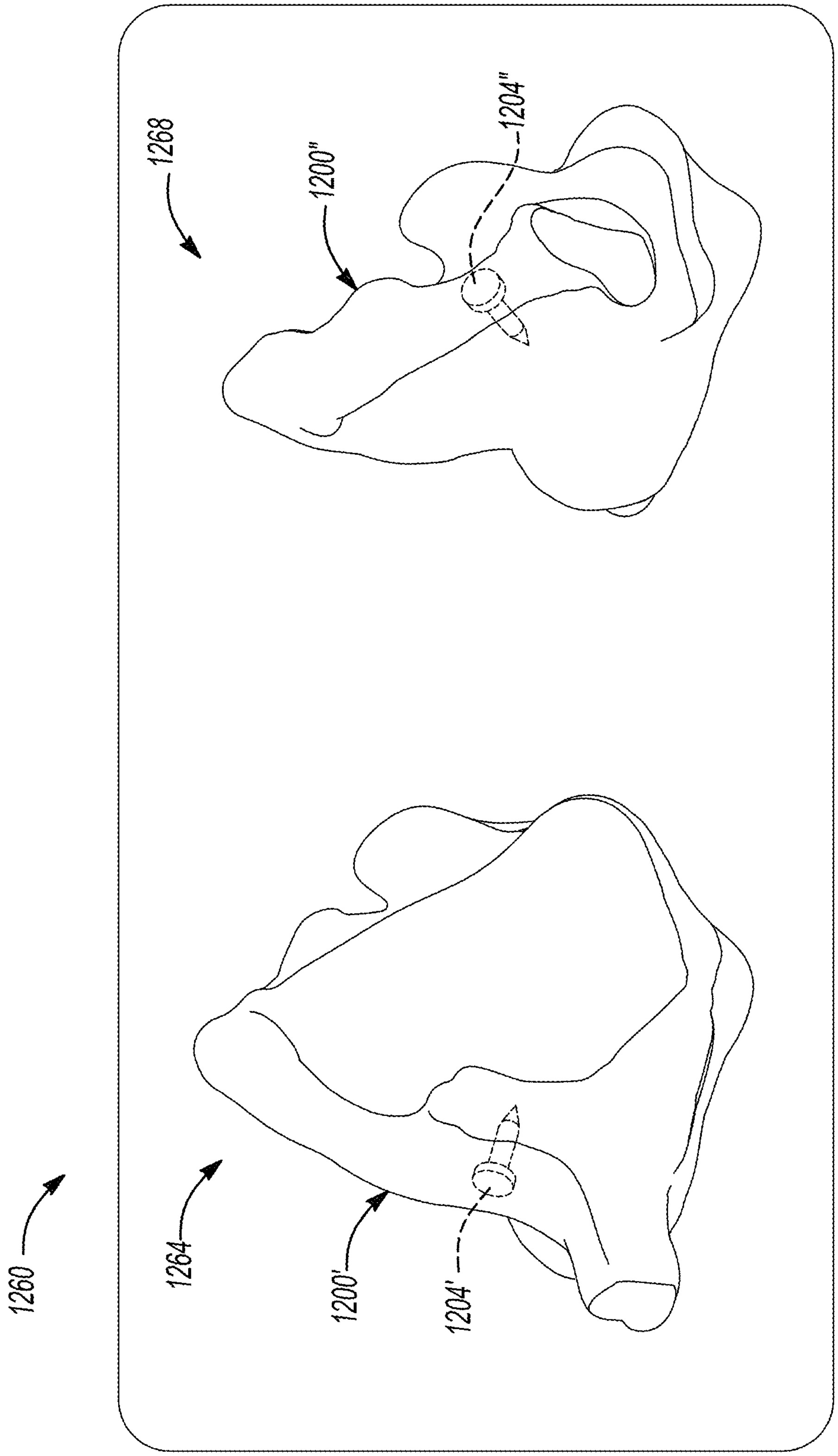
FIG. 19 is a schematic illustration of an image generated with the system as illustrated in FIG. 18, according to various embodiments.

The two contact points 1230, 1234 allows for a generation of the image of a selected portion, such as the vertebrae 1200 and/or the pedicle screw 1204 at two different perspectives substantially simultaneously. With continuing reference to FIG. 18 and addition to reference FIG. 19, a single projection 1260 is illustrated. The single projection 1260 may include two projections at two different perspectives of a single portion of the subject 30, such as the vertebrae 1200 and/or the pedicle screw 1204. The single projection 1260 may include a first projection portion 1264 that relates to the beam 1210 from the source portion 400. The single projection 1260 may include a second projection portion 1268 that relates to the second beam 1214 of the source portion 4200. The two projection portions 1264, 1268 may be generated due to the two beams 1210, 1214 from the two perspective source portions 400, 420 that are offset from one another by the offset 1242. Each of the projections may include the same portion, such as the vertebra projection portion 1200' at the first perspective and the vertebral position 1200" at the second perspective. Similarly each may include a pedicle screw projection such as the pedicle screw at the first projection 1204' and a pedicle screw at the second projection 1204". The single projection 1260, therefore, may include two perspectives of any one single portion (e.g. the vertebrae 1200 and/or the pedicle screw 1204).

The dual perspectives of the single portion may allow for a registration to a prior acquired image. For example, a prior acquired image may include a magnetic resonance image (MRA), a cone beam reconstruction, a computer tomography (CT), or other appropriate image of the subject 30. The prior acquired image may be acquired at any appropriate time and acquired with any appropriate imaging modality. Nevertheless, the prior acquired image may include a three-dimensional image of a selected portion of the subject, such as the vertebrae 1200 and/or the pedicle screw 1204. Selected or known techniques, such as back projection techniques, may be used to register the prior acquired image to the presently or later acquired image, such as the single projection 1260. Accordingly, at a selected time, such as during a selected procedure, the imaging system 80 may be used to acquire a single projection with two or more of the source portions. The single projection may include two or more perspectives of a single portion of the subject 30 and the two or more perspectives may allow for registration to a prior acquired image.

Accordingly, registration to a prior acquired image may be used for planning and/or confirming a selected procedure. The registration may be determined with the single projection 1260 generated with the imaging system 80. Further, the registration to the prior acquired image may allow for navigation relative to a selected plan or other appropriate techniques. Nevertheless, the imaging system 80 including the two or more source portions of the source assembly 86 may allow for registration to a prior acquired image with a single projection image, such as a single projection image 1260.

It is understood that all of the exemplary use of the vertebrae 1200 and/or the pedicle screw 1204 as illustrated that registration appropriate subject portion is possible. Further, while a human subject is discussed as an example, various inanimate or non-human subjects may also be used.

The imaging system, according to various embodiments, may also be operated to generate or acquire a limited-angle tomography. A limited-angle tomography may include a limited or less than 180 or 360 image data acquisition of the subject. In various embodiments, the limited-angle tomography may include moving the gantry through a limited angle, exciting the source array over a limited angle, and/or a combination of both.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, graphic processing units (GPUs), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An imaging system for acquiring image data of a subject, comprising:

a source assembly configured to be positioned relative to an imaging region relative to the subject, wherein the source assembly includes at least a first source portion and a second source portion, wherein the first source portion is spaced a source distance away from the second source portion;

a detector configured to be positioned relative to the imaging region, wherein the detector is configured to be positioned to detect image data from both the first source portion and the second source portion substantially simultaneously; and a controller configured to execute instructions to:

generate image data based on the substantially simultaneous detection at the detector; and register the generated image data to prior acquired image data.

2. The system of claim 1, further comprising:

a gantry, wherein the gantry is configured to encompass at least a portion of the source assembly and the detector and position the source assembly and the detector relative to the imaging region.

3. The system of claim 2, further comprising:

a mobile cart configured to move the gantry from a first position to a second position.

4. The system of claim 2, wherein the controller is configured to further execute instructions to operate the first source portion and the second source portion to selectively emit x-rays through the imaging region to be detected at the detector to generate the image data.

5. The system of claim 1, wherein the prior acquired image data is 3D image data.

6. The system of claim 5, wherein the source assembly defines an axis extending through the imaging region;

wherein the first source portion is angularly offset from the second source portion with the source assembly.

7. The system of claim 6, wherein the first source portion is fixed at the angularly offset position relative to the second source portion;

wherein the first source portion is configured to acquire a first perspective image and the second source portion is configured to acquire a second perspective image.

8. The system of claim 7, wherein the angularly offset position between the first source portion and the second source portion is configured to generate a first perspective and a second perspective at the detector of an object within the imaging region while the source assembly is at a single position.

9. The system of claim 8, wherein the first source portion is configured to emit a first beam of x-rays along a first ray toward the detector through the imaging region and the second source portion is configured to emit a second beam of x-rays along a second ray toward the detector through the imaging region;

wherein the subject is operable to attenuate x-rays detected at the detector.

10. The system of claim 7, wherein the first source portion is configured to emit a first beam of x-rays toward the detector through the imaging region and the second source portion is configured to emit a second beam of x-rays toward the detector through the imaging region.

11. The system of claim 2, wherein the gantry includes a fixed gantry portion and a moveable gantry portion;

wherein the moveable gantry portion is configured to move relative to the fixed gantry portion to allow access to the imaging region defined by the gantry;

wherein the gantry in a closed configuration is configured to at least partially surround the imaging region;

wherein the source assembly is operable to move within at least one of the fixed gantry portion or the moveable gantry portion.

12. The system of claim 2, wherein the source assembly includes a plurality of first source portions and a plurality of second source portions;

wherein each of the plurality of first source portions is angularly spaced from each of the plurality of second source portions.

13. A method of acquiring image data of a subject with an imaging system, comprising:

positioning a source assembly relative to an imaging region including at least a portion of the subject;

providing the source assembly with a first source portion spaced a source distance away from a second source portion;

detecting at a detector a first emission from the first source portion and a second emission from the second source portion substantially simultaneously;

generating image data based on the substantially simultaneous detection at the detector; and registering the generated image data to prior acquired image data.

14. The method of claim 13, further comprising:

operating both the first source portion to emit a first beam as the first emission and the second source portion to emit a second beam as the second emission; and collecting a single projection at the detector generated with both the first beam and the second beam;

wherein generating the image data includes generating a single image data based on the single projection.

15. The method of claim 13, further comprising:

providing a gantry to encompass at least a portion of the source assembly and the detector and position the source assembly and the detector relative to the imaging region.

16. The method of claim 13, further comprising:

providing the source assembly to define an axis extending through the imaging region; and providing the first source portion to be angularly offset from the second source portion with the source assembly.

17. The method of claim 16, further comprising:

providing the first source portion fixed at the angularly offset position relative to the second source portion; and acquiring with the first source portion a first perspective image and with the second source portion a second perspective image.

18. The method of claim 17, further comprising:

based on the angularly offset position between the first source portion and the second source portion, generating a first perspective and a second perspective at the detector of the subject within the imaging region while the source assembly is at a single position.

19. The method of claim 13, further comprising:

acquiring with the first source portion a first perspective image and with the second source portion a second perspective image; and acquiring the prior acquired image data separate from the generated image data.

20. The method of claim 19, wherein registering the generated image data to the prior acquired image data includes:

forming a back-projection image through the prior acquired image data; and comparing the back-projection image to the first perspective image and the second perspective image.

* * * * *